United States Patent
Maynard

(10) Patent No.: US 10,662,295 B2
(45) Date of Patent: May 26, 2020

(54) TREHALOSE HYDROGELS FOR STABILIZATION AND DELIVERY OF PROTEINS

(71) Applicant: THE REGENTS OF THE UNIVERSITY OF CALIFORNIA, Oakland, CA (US)

(72) Inventor: Heather D. Maynard, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/503,348

(22) PCT Filed: Aug. 12, 2015

(86) PCT No.: PCT/US2015/044771
§ 371 (c)(1),
(2) Date: Feb. 10, 2017

(87) PCT Pub. No.: WO2016/025551
PCT Pub. Date: Feb. 18, 2016

(65) Prior Publication Data
US 2017/0240711 A1 Aug. 24, 2017

Related U.S. Application Data

(60) Provisional application No. 62/036,431, filed on Aug. 12, 2014, provisional application No. 62/138,110, filed on Mar. 25, 2015.

(51) Int. Cl.
| | |
|---|---|
| C08J 3/075 | (2006.01) |
| C08F 12/32 | (2006.01) |
| A61K 9/06 | (2006.01) |
| A61K 38/28 | (2006.01) |
| A61K 9/00 | (2006.01) |
| A61K 47/36 | (2006.01) |
| C08F 12/22 | (2006.01) |
| C08F 212/14 | (2006.01) |
| A23K 20/163 | (2016.01) |
| A61K 47/32 | (2006.01) |
| C12N 9/16 | (2006.01) |
| C12N 9/96 | (2006.01) |

(52) U.S. Cl.
CPC ............ *C08J 3/075* (2013.01); *A23K 20/163* (2016.05); *A61K 9/0019* (2013.01); *A61K 9/06* (2013.01); *A61K 38/28* (2013.01); *A61K 47/32* (2013.01); *A61K 47/36* (2013.01); *C08F 12/22* (2013.01); *C08F 12/32* (2013.01); *C08F 212/14* (2013.01); *C12N 9/16* (2013.01); *C12N 9/96* (2013.01); *C12Y 301/03026* (2013.01); *C08J 2325/18* (2013.01)

(58) Field of Classification Search
None
See application file for complete search history.

(56) References Cited

U.S. PATENT DOCUMENTS

| | | | |
|---|---|---|---|
| 7,718,193 B2 | 5/2010 | Stayton | |
| 8,201,170 B2 | 6/2012 | Lescout | |
| 8,501,478 B2 | 8/2013 | Reineke | |
| 9,572,910 B2 | 2/2017 | Messersmith | |
| 9,901,648 B2 | 2/2018 | Maynard | |
| 9,962,437 B2 | 5/2018 | Wang | |
| 9,994,615 B2 | 6/2018 | Langer | |
| 2003/0027965 A1 | 2/2003 | Solomon | |
| 2007/0224241 A1* | 9/2007 | Stayton | B82Y 5/00 424/423 |
| 2012/0135017 A1 | 5/2012 | Harel | |
| 2013/0157926 A1 | 6/2013 | Engbersen | |
| 2014/0372189 A1 | 12/2014 | Amouris | |
| 2017/0129999 A1 | 5/2017 | Messersmith | |

FOREIGN PATENT DOCUMENTS

| | | |
|---|---|---|
| WO | 2002050143 | 6/2002 |
| WO | 2013123491 | 8/2013 |
| WO | WO 2013112987 A1 * 8/2013 | ......... G06Q 30/0251 |

OTHER PUBLICATIONS

Teramoto, Naozumi, and Mitsuhiro Shibata. "Trehalose-based thermosetting resins. I. Synthesis and thermal properties of trehalose vinylbenzyl ether." Journal of applied polymer science 91.1 (2004): 46-51.*
Petrusic, Stojanka, et al. "Synthesis, characterization and drug release properties of thermosensitive poly (N-isopropylacrylamide) microgels." Journal of Polymer Research19.10 (2012): 9979. (Year: 2012).*
Omidian, Hussein, et al. "Swelling and crosslink density measurements for hydrogels." Iranian J. of Polymer Science and Technology vol. 3.2 (1994). (Year: 1994).*
Akiyoshi, K., et al., "Molecular chaperone-like activity of hydrogel nanoparticles of hydrophobized pullulan: thermal stabilization with refolding of carbonic anhydrase B." Bioconjugate Chemistry 103 (1999): 321-324.
Bajpai, A. K., et al. "Responsive polymers in controlled drug delivery." Progress in Polymer Science 33 (2008): 1088-1118.
Besheer, A., et al. "Loading and mobility of spin-labeled insulin in physiologically responsive complexation hydrogels Intended for oral administration." Journal of controlled release 111.1-2 (2006): 73-80.
Cambre, J., et al., "Biomedical applications of boronic acid polymers." Polymer 52.21 (2011): 4631-4643.
Grover, G., et al. "Biocompatible hydrogels by oxime click chemistry." Biomacromolecules 13.10 (2012): 3013-3017.
Gupta, P. et al., "Hydrogels: from controlled release to pH-responsive drug delivery." Drug discovery today 7.10 (2002): 569-579.

(Continued)

Primary Examiner — Nissa M Westerberg
(74) Attorney, Agent, or Firm — Quarles & Brady LLP

(57) ABSTRACT

Trehalose-based hydrogels and methods of making such hydrogels are disclosed. Specifically, a method of creating a trehalose-based hydrogel, comprising the steps of: a) forming a trehalose homopolymer or co-polymer; b) preparing a cross-linker; and c) reacting the trehalose homopolymer or co-polymer with the cross-linker to form the trehalose-based hydrogel.

12 Claims, 24 Drawing Sheets

(56) References Cited

OTHER PUBLICATIONS

Kaushik, J. et al., "Why is trehalose an exceptional protein stabilizer? An analysis of the thermal stability of proteins in the presence of the compatible osmolyte trehalose." Journal of Biological Chemistry 278.29 (2003): 26458-26465.

Lee, J., et al. "Trehalose glycopolymers as excipients for protein stabilization." Biomacromolecules 14.8 (2013): 2561-2569.

Lee, J., et al. "Trehalose hydrogels for stabilization of enzymes to heat." Polymer chemistry 6.18 (2015): 3443-3448.

Lee, J. et al., "Glucose-Responsive Trehalose Hydrogel for Insulin Stabilization and Delivery." Macromolecular bioscience 18.5 (2018): 1700372.

Lei Y. et al."The spreading, migration and proliferation of mouse mesenchymal stem cells cultured inside hyaluronic acid hydrogels." Biomaterials 32.1 (2011): 39.

Li, R. C. et al., "Well-defined polymers with acetal side chains as reactive scaffolds synthesized by atom transfer radical polymerization." Journal of Polymer Science Part A: Polymer Chemistry 44.17 (2006): 5004-5013.

Lippert K., et al., "Enzyme stabilization be ectoine-type compatible solutes: protection against heating, freezing and drying." Applied microbiology and biotechnology 37.1 (1992): 61-65.

Lowman, A. M., et al. "Oral delivery of insulin using pH-responsive complexation gels." Journal of pharmaceutical sciences 88.9 (1999): 933-937.

Mancini, R.J., et al., "Trehalose glycopolymers for stabilization of protein conjugates to environmental stressors." Journal of the American Chemical Society 134.20 (2012): 8474-8479.

Matsumoto, A., et al. "A synthetic approach toward a self-regulated insulin delivery system." Angewandte Chemie International Edition 51.9 (2012): 2124-2128.

Murthy, N., et al. "A novel strategy for encapsulation and release of proteins: hydrogels and microgels with acid-labile acetal cross-linkers." Journal of the American Chemical Society 124.42 (2002): 12398-12399.

PCT International Search Report and Written Opinion for PCT/US15/44771 dated Nov. 10, 2015, 12 pages.

Piluso S. et al."Hyaluronic acid-based hydrogels crosslinked by copper-catalyzed azide-alkyne cycloaddition with tailorable mechanical properties." The International journal of artificial organs 34.2 (2011): 192-197.

Qiu, Y., et al., "Environment-sensitive hydrogels for drug delivery." Advanced drug delivery reviews 53.3 (2001): 321-339.

Ravaine, V. et al. "Chemically controlled closed-loop insulin delivery." Journal of Controlled Release 132.1 (2008): 2-11.

Teramoto, N., et al., "Trehalose and trehalose-based polymers for environmentally benign, biocompatible and bioactive materials." Molecules 13.8 (2008): 1773-1816.

Xu, X., et al. "Hyaluronic acid-based hydrogels: from a natural polysaccharide to complex networks." Soft matter 8.12 (2012): 3280-3294.

Yang, T., et al. "Glucose-responsive hydrogels based on dynamic covalent chemistry and inclusion complexation." Soft Matter 10 (2014): 2671-2678.

* cited by examiner

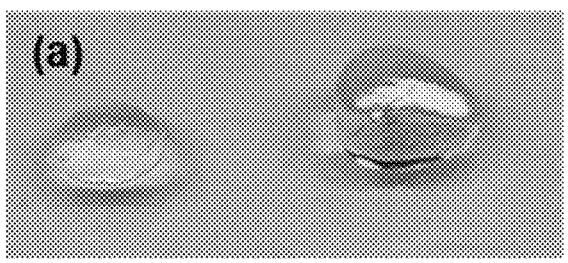 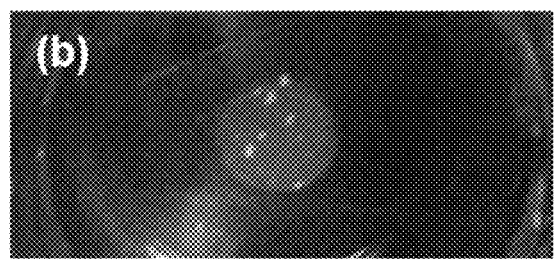
Figure 2(a and b)

Figure 11(a-e)

Figure 14 (a and b)

TREHALOSE HYDROGELS FOR STABILIZATION AND DELIVERY OF PROTEINS

CROSS-REFERENCE TO RELATED APPLICATION(S)

This application represents the national stage entry of PCT International Application PCT/US2015/044771 filed Aug. 12, 2015 and claims priority U.S. Provisional Patent Applications 62/036,431 filed Aug. 12, 2014 and 62/138,110 filed Mar. 25, 2015. The contents of this application are hereby incorporated by reference as if set forth in their entirety herein.

STATEMENT REGARDING FEDERALLY SPONSORED RESEARCH OR DEVELOPMENT

This invention was made with Government support under CHE1112550, awarded by the National Science Foundation. The Government has certain rights in the invention.

FIELD OF THE INVENTION

Compositions and methods for making trehalose hydrogels for stabilization and delivery of proteins are disclosed. Specifically, the compositions include novel trehalose-based homopolymers or copolymers with addition of cross-linkers, wherein the homopolymers or copolymers form trehalose hydrogels to stabilization and delivery of proteins.

BACKGROUND OF THE INVENTION

Enzymes have well-defined three-dimensional structures formed by multiple noncovalent interactions such as hydrogen bonds, salt bridges, and hydrophobic interactions (Somero, 1995). At high temperatures, enzymes lose their original structure and denature to form insoluble aggregates that are no longer active (Somero, 1995; Rader et al., 2002; Fágáin, 1995). Because of their high efficiency and selectivity in catalyzing biological processes, enzymes are used for numerous industrial purposes (Rader et al., 2002; Ravindran and Son, 2011; Samejima et al., 1980; Schmid et al., 2001). However, this thermal instability of the proteins has negative impact on their applications in the pharmaceutical, food, and biotechnology industries. Many techniques such as chemical modification (DeSantis and Jones, 1999; Ryan et al., 1994) and protein engineering (Frosst et al., 1995; Matthews et al., 1987; Kumar et al., 2000; Imanaka et al., 1986) have been developed to address this problem. Additionally, polymers have been used as conjugates or excipients to enhance thermostability of enzymes (Gaertner and Puigserver, 1992; Longo and Combes, 1999; Yang et al., 1996; Kazan and Erarslan, 1997; Tomita et al., 2012). Yet some of these approaches are too expensive for certain industrial and agricultural applications.

For industrial applications, polymeric hydrogels are especially attractive materials for enzyme stabilization. Enzyme immobilization by hydrogels has been extensively studied in the context of industrial enzyme stabilization, especially to organic solvents (Sheldon, 2007). Enzymes can be loaded onto hydrogels without the need of a conjugation reaction, which simplifies the synthesis and stabilization process. And unlike polymer excipients that are difficult to remove from the enzyme solution, the macroscopic hydrogels can be easily separated by filtration or centrifugation. Due to these advantages, hydrogels have been frequently used for stabilization of enzymes as well as other proteins (Leobandung, 2002; Akiyoshi et al., 1999; Wang et al., 2008). Herein, we propose a novel hydrogel system based on trehalose as an effective excipient for enhancing the stability of enzymes at elevated temperatures.

Trehalose is a non-reducing disaccharide that has been shown to stabilize proteins and cells against stresses such as heat (Lippert and Galinski, 1992; Kaushik and Bhat, 2003; Baptista et al., 2008), desiccation (Guo et al., 2000; Hengherr et al., 2008; Crowe et al., 1984), and freezing (Beattie et al., 1997; Sundaramurthi and Suryanarayanan, 2009; Duong et al., 2006). Some animals accumulate trehalose to significant levels in response to environmental stresses (Westh and Ramlov, 1991; Madin and J. H. Crowe, 1975), emphasizing the ability of trehalose to stabilize biological molecules. Moreover, trehalose is generally regarded as safe (GRAS) (Jain and Roy, 2009) and is used in several pharmaceutical drugs as stabilizers (Ohtake and Wang, 2011). Our group has previously utilized trehalose-based linear polymers as excipients (Lee et al., 2013) or conjugates (Mancini et al., 2012) to stabilize proteins and retain their activity against heat and lyophilization. We sought to develop trehalose-based material to stabilize enzymes against heat and focused on hydrogels for the advantages described above.

Hydrogels have been extensively used as drug delivery vehicles with biomedical applications (Roy and Gupta, 2003). "Smart hydrogels", which respond to specific triggers, can be synthesized to deliver and release guest drugs into a specifically targeted site (Bajpai et al., 2008; Gupta et al., 2002; Qiu and Park, 2001; Kiyonaka et al., 2002; Mano, 2008). In particular, pH responsive hydrogels are frequently used in drug delivery because different cell types and compartments of cells have discrete pHs, which allows for site specific release of a payload. For example, the pH of the extracelluar matrix (ECM) is typically around 7.4, while the cytosol has a lower pH and cancer cells are also more acidic than normal cells (Ingber et al., 1990; Wei et al., 2014). Moreover, the pH in the stomach is between pH 2 and 4 depending on whether the stomach is empty or food has been injested (Qiu and Park, 2001). Therefore research on pH responsive hydrogels is an important field of interest. Significant research has been reported toward the oral administration of therapeutics using pH responsive hydrogels. These hydrogels target the stomach for site-specific delivery of antibiotic, therapeutic proteins, and peptides (Lowman et al., 1999; Patel and Amiji, 1996; Besheer et al., 2006; Guo and Gao, 2007; Nho et al., 2005; Sajeesh and Sharma, 2006; Shantha and Harding, 2000). Since the target site is the stomach and stomach pH is 2-4 depending on empty or full, the hydrogels must only release their therapeutics in conditions more acidic than pH 4. This release occurs by changing the degree of swelling in the hydrogel or by cleaving the crosslinker.

Needed in the art are trehalose hydrogels for stabilization and delivery of proteins as animal feed stabilizers. Phytase is produced by bacteria found in the gut of ruminant animals (cattle, sheep) making it possible for them to use the phytic acid found in grains as a source of phosphorus. Non-ruminants (monogastric animals) like human beings, dogs, birds, etc. do not produce phytase. Research in the field of animal nutrition has put forth the idea of supplementing feed with phytase so as to make available to the animal phytate-bound nutrients like calcium, phosphorus, other minerals, carbohydrates and proteins.

This is a huge market with increasing importance for animal feed stabilizers (e.g., phytase). Needed in the art are trehalose-based hydrogels for stabilization and delivery of animal feed enzymes (e.g., phytase). These trehalose-based hydrogels should be responsive to the surrounded environments, e.g., pH values or the presence of glucose.

Insulin was the first Food and Drug Administration (FDA)-approved recombinant protein drug, and is widely used for the treatment of diabetes (Brown, 2005). However, one of the challenges associated with insulin therapy is the requirement of repeated injection or insertion of insulin bolus after each meal in the case of the insulin pump, which is problematic especially for children and young adults (Burdick et al., 2004). To address these challenges, phenylboronic acid that is non-toxic and durable has been widely used in materials for insulin release (Wu et al., 2011). Since boronic acid forms dynamic covalent complexes with 1,2- or 1,3-diols (Cambre and Sumerlin, 2011), its incorporation into hydrogels results in glucose-responsive materials. The two main mechanisms of insulin release from boronic acid hydrogels are swelling and competitive binding (Wu et al., 2011). The swelling mechanism is caused by the shift in the equilibrium of different boronic acid species toward the anionic tetrahedral form upon binding to diols such as those on sugars, which causes osmotic swelling of the hydrogels (Matsumoto et al., 2012). Alternatively, boronic acid-based polymers (Bapat et al., 2011) can form a hydrogel upon complexation with a diol-containing polymer in the presence of insulin, and later be competitively displaced by glucose to dissolve the hydrogel and release insulin (Wang et al., 2014).

In addition to controlled release of insulin, the instability of the protein is an important issue that needs to be addressed. Exposure of insulin to changes in temperature during storage may lead to inactivation of the protein resulting in health complications (Pryce, 2009). Instability also contributes to the medical costs of diabetes treatment because of protein that is discarded and wasted (Weiss et al., 2011). While insulin has been modified to increase its half-life in vivo (by covalent attachment of a polymer) (Hinds and Kim, 2002) and to prevent insulin hexamer formation (by mutation of the amino acid sequence) (Heise et al., 2007), only a few studies have reported stabilizing insulin to environmental heat exposure (Leobandung et al., 2002; Akiyoshi et al., 1998). Peppas has used nanospheres composed of poly(N-isopropylacrylamide) and poly(ethylene glycol) to enhance thermal and mechanical stability of insulin (Leobandung et al., 2002), but their system lacked a release mechanism. Akiyoshi et al. have used cholesterol-bearing pullulan nanogels to stabilize insulin against heat and enzymatic degradation, and the nanogel released insulin when exposed to physiological bovine serum albumin (BSA) level by association of BSA with pullulan (Akiyoshi et al., 1998). Although this system successfully stabilized insulin, it lacked glucose responsiveness, which is highly desirable in insulin delivery systems. To our knowledge, a hydrogel that is both glucose-responsive and insulin stabilizing has not yet been reported.

Needed in the art are trehalose hydrogels for stabilization and delivery of proteins. Needed in the art are trehalose-based hydrogels which are responsive to the surrounded environments, e.g., pH values or the presence of glucose.

SUMMARY OF THE INVENTION

In one aspect, the present invention relates to a method of creating a trehalose-based hydrogel. The method comprises the steps of a) forming a trehalose homopolymer or co-polymer; b) preparing a cross-linker; and c) reacting the trehalose homopolymer or co-polymer with the cross-linker to form the trehalose-based hydrogel.

In one embodiment, the trehalose homopolymers or co-polymers have the structure of $R_5$—$[R_1R_2C$—$CR_3R_4]_n$—$R_6$, wherein $R_1$-$R_4$ are independently selected from hydrogen or a side chain comprising at least one carbon atom, and wherein at least one of $R_1$-$R_4$ is a side chain comprising -L-trehalose, wherein L is a linker molecule that links trehalose to the monomer through at least one of the trehalose hydroxyl groups (—OH), and wherein $R_5$ and $R_6$ are independently selected from the group consisting of -Alkyl, -Alkenyl, -Alkynyl, -aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), and biomolecules.

In one embodiment, the trehalose homopolymers or co-polymers are either polyethylene glycols or polyethylene glycol (PEG) derivatives.

In one embodiment, the cross-linker is a boronic acid-based cross-linker.

In one embodiment, the cross-linker has the structure:

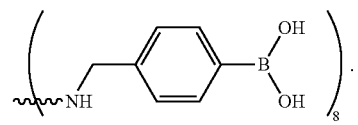

In one embodiment, the trehalose homopolymer or co-polymer is a polyethylene glycol (PEG) derivative.

In one embodiment, the ratio of the cross-linker to the trehalose homopolymer or co-polymer is 1:1.

In one embodiment, the reaction between the trehalose homopolymer or co-polymer and the cross-linker occurs at pH 7.4 and in Dulbecco phosphate buffered saline (D-PBS).

In one aspect, the present invention relates to a method of stabilizing and delivering a protein. The method comprises the steps of a) preparing a trehalose-based hydrogel according to any method from claims 1-8; b) adding a protein into the trehalose-based hydrogel either at the time of hydrogel formation or after the formation to form a complex of the protein and the trehalose-based hydrogel; and c) adding a sugar solution into the complex of the protein and the trehalose-based hydrogel or lowering the pH of the solution to release the protein from the complex.

In one embodiment, a protein is added during the preparation of trehalose-based hydrogel to form a complex of the protein and the trehalose-based hydrogel.

In one embodiment, the protein is an insulin.

In one embodiment, the sugar solution is a glucose solution.

In one aspect, the present invention relates to a method of creating a trehalose-based hydrogel, comprising the steps of a) preparing a trehalose cross-linker; b) preparing a trehalose-based monomer; and c) reacting the trehalose cross-linker with the trehalose-based monomer to form the trehalose-based hydrogel.

In one embodiment, the trehalose cross-linker is synthesized using identical chemistry as is used to prepare the trehalose-based monomer.

In one embodiment, the trehalose cross-linker is synthesized during the same step as that is used to prepare the trehalose-based monomer.

In one embodiment, the reaction in step b) is Free Radical Polymerization initiated by a Redox initiator.

In one embodiment, the trehalose cross-linker has the structure

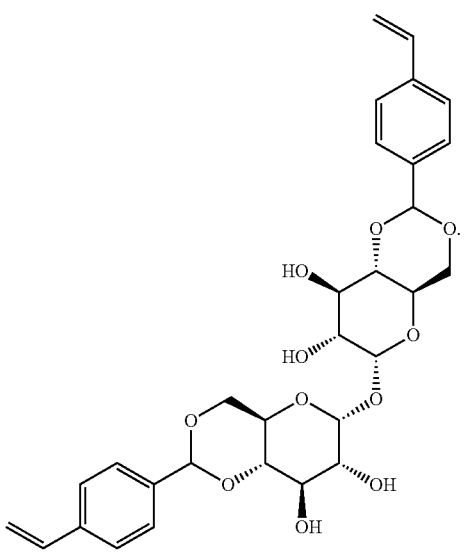

In one embodiment, the trehalose-based monomer has the structure

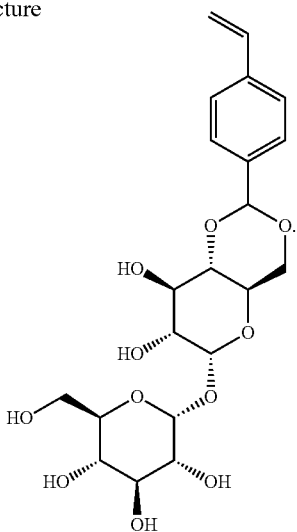

In one embodiment, the trehalose cross-linker comprises the structure

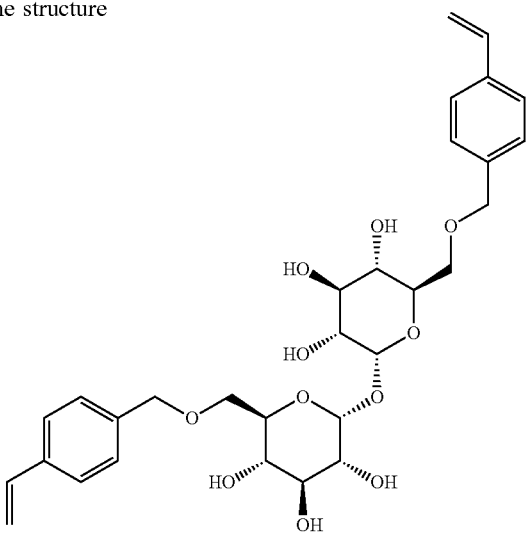

In one embodiment, the trehalose-based monomer has the structure

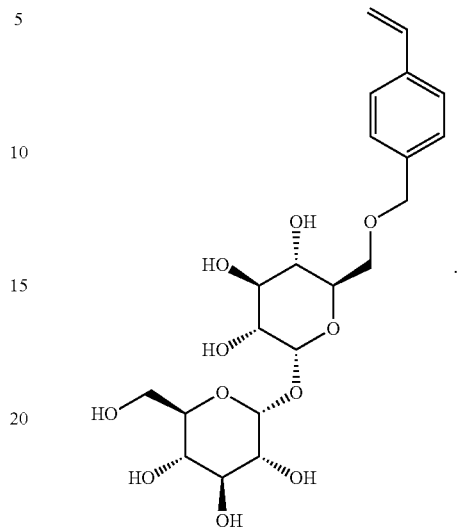

In one embodiment, no HPLC purification process to purify the trehalose-based monomer is needed.

In one aspect, the present invention relates to a method of stabilizing a protein, comprising the steps of a) preparing a trehalose-based hydrogel according to any method from claims 13-21; and b) adding a protein into the trehalose-based hydrogel either at the time of hydrogel formation or after the formation to form a complex of the protein and the trehalose-based hydrogel; wherein the protein is stabilized.

In one embodiment, the protein is an enzyme.

In one embodiment, the protein is stabilized when exposed to heat.

In one embodiment, the protein is stabilized above 4° C.

In one embodiment, the protein is stabilized at 70-90° C.

In one embodiment, the protein is released from the complex of the protein and the trehalose-based hydrogel by diluting with water or lowering the pH.

BRIEF DESCRIPTION OF THE DRAWINGS

FIG. 2 (a and b) is a set of photographs showing (a) photograph of the formed trehalose-boronic acid hydrogel and (b) photograph of trehalose-boronic acid hydrogel loaded with FITC-labeled insulin in pH 7.4 D-PBS.

DETAILED DESCRIPTION OF THE INVENTION

In General

Figure 1:
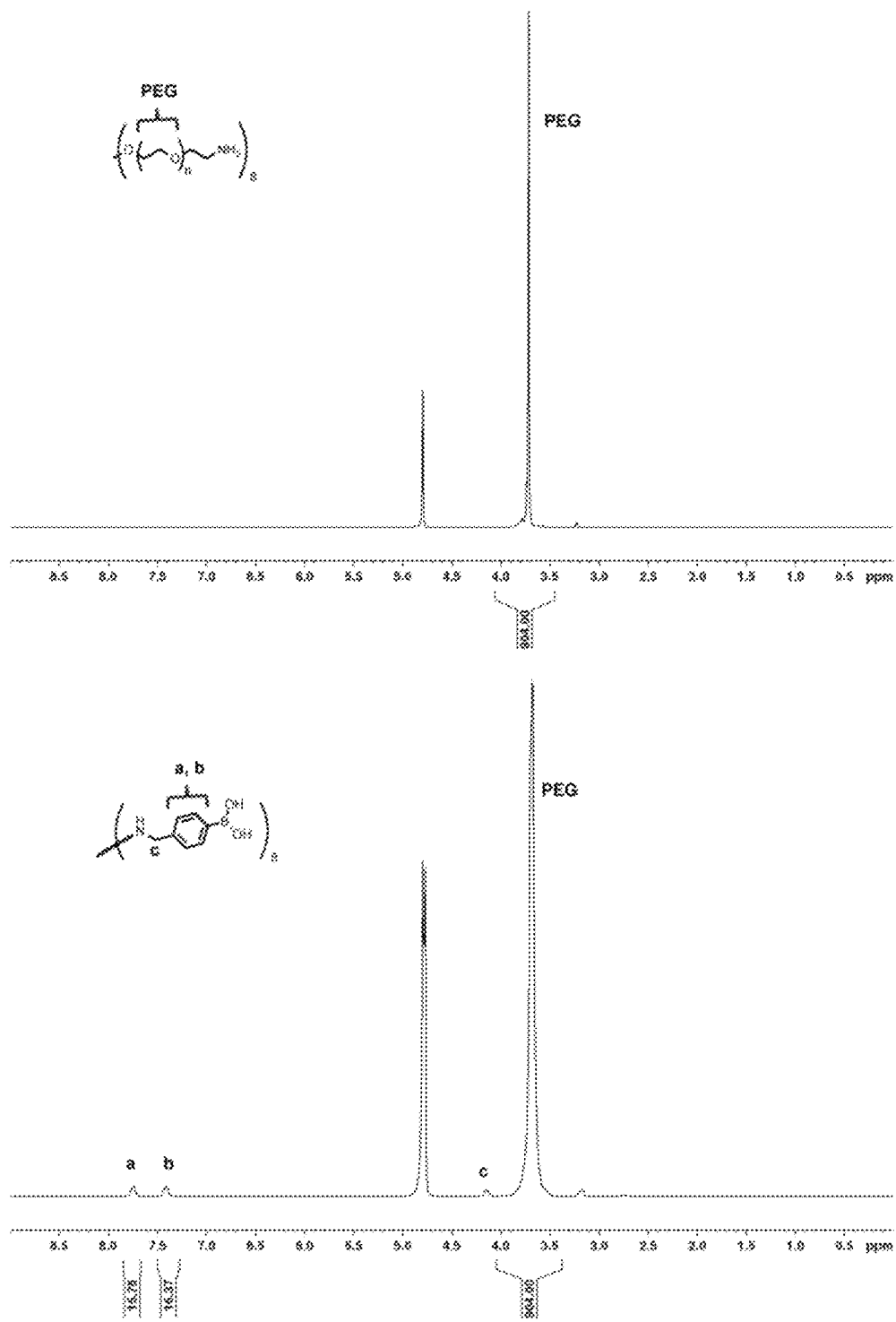
FIG. 1 is a set of graphs showing $^1$H NMR spectra of 8arm PEG amine (top) and 8arm PEG boronic acid (bottom) (in $D_2O$).

Before the present materials and methods are described, it is understood that this invention is not limited to the particular methodology, protocols, materials, and reagents described, as these may vary. It is also to be understood that the terminology used herein is for the purpose of describing particular embodiments only and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Definitions

Before the composition and related methods are described, it is to be understood that this invention is not limited to the particular methodology, protocols, materials, and reagents described, as these may vary. The terminology used herein is for the purpose of describing particular embodiments only, and is not intended to limit the scope of the present invention which will be limited only by any later-filed non-provisional applications.

The invention described herein provides trehalose-based hydrogels for stabilization and delivery of proteins.

According to one embodiment of the invention, a trehalose-based hydrogel is used to stabilize protein against aggregation, conformational changes and/or degradation, such as denaturation of native protein or renaturation of denatured (unfolded or partially folded) protein, helping to maintain the protein in the desired configuration in a hostile or stressful environment, and intended function is maintained to be at least equal to the protein in its natural states or is enhanced over a reduced activity that the protein would have in the stressful environment. A trehalose-based hydrogel will act to stabilize proteins against degradation, e.g. by heat, electromagnetic radiation, shear stress, proteolysis, or by chemical modification such as reduction, oxidation, or carbamylation. A trehalose-based hydrogel may be used to stabilize a protein in aqueous solution, or in dry form, e.g. produced by desiccation, dehydration, evaporation or lyophilisation (freeze drying) of an aqueous solution.

One method of producing trehalose-based hydrogels may comprise the step of reacting a trehalose homopolymer or co-polymer with a pre-synthesized cross-linker to form the trehalose-based hydrogel.

Another method of producing trehalose-based hydrogels may comprise the step of co-polymerizing a trehalose crosslinker with a trehalose-based monomer to form the trehalose-based hydrogel.

The term "aryl" refers to a carbocyclic (non-heterocyclic or heterocyclic) aromatic ring or mono-, bi- or tri-cyclic ring system. The aromatic ring or ring system is generally composed of 6 to 10 carbon atoms. Examples of aryl groups include but are not limited to phenyl, biphenyl, naphthyl and tetrahydronaphthyl. 6-membered aryls such as phenyl are preferred.

The term "alkyl" refers to optionally substituted straight chain or branched chain hydrocarbon groups. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "alkyl" also encompasses alkyl groups containing one less hydrogen atom such that the group is attached via two positions, i.e., divalent. "$C_{1-4}$alkyl" and "$C_{1-3}$alkyl" including methyl, ethyl, propyl, isopropyl, n-butyl, iso-butyl, sec-butyl and tert-butyl are preferred with methyl being particularly preferred.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are difluoromethyl, trifluoromethyl, and the like. "Halogens" are elements including chlorine, bromine, fluorine, and iodine.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

The term "stressful environment," as used herein, means an environment which will reduce a functional property or activity of a biomolecule. For example, the environment may reduce a functional property or activity of a protein over a native protein or that which the protein has in its natural state. A stressful environment may include temperatures which create adverse thermal environments which could be elevated or reduced temperatures, solvents such as an organic solvent, the presence of proteases, pH and/or lack of buffer.

The term "biomolecule" as used herein refers, but is not limited to proteins, enzymes, antibodies, DNA, siRNA, and pharmaceutical compositions. Such biomolecules are subject to environmental stresses which include but are not limited to heat, desiccation, light, storage, exposure to enzymes, endo- and exo-nucleases and pH variation.

The term "protein" used herein refers to any compound of two or more individual amino acids (whether or not naturally occurring) linked via peptide bonds, as occur when the carboxyl carbon atom of the carboxylic acid group bonded to the α-carbon of one amino acid (or amino acid residue) becomes covalently bound to the amino nitrogen atom of the amino group bonded to the α-carbon of an adjacent amino acid. These peptide bond linkages, and the atoms comprising them (i.e., α-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide." Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As may be appreciated, a "fragment" of a protein may be a form of the protein truncated at the amino terminus, the carboxyl terminus, and/or internally (such as by natural splicing), and may also be variant and/or derivative. A "domain" of a protein is also a fragment, and comprises the amino acid residues of the protein required to confer biochemical activity corresponding to naturally occurring protein. The term "protein" used herein also include "protein conjugate" which refers to a compound complex comprising a "protein" which is interlinked to one another molecule or subject. The term "complex" is used herein to mean those compounds comprising at least two components. The protein may be naturally occurring and isolated from its source. The protein may be produced using DNA recombination or mutation techniques. The protein may be produced in vivo in a whole animal, or in a eukaryotic or prokaryotic cell; alternatively, the protein may be generated using an in vitro method such as cell-free in vitro translation, e.g., using E. coli lysate, wheat germ extract, or rabbit reticulocyte. Cell free in vitro translation methods can be employed following in vitro transcription, e.g., following phage or ribosome display.

Examples of proteins include, without limitation, Lysozyme, Adenosine deaminase, L-Asparaginase, Mammalian urate oxidase, Interferons, Anti-TNF α Fab, granulocyte colony stimulated factor (G-CSF), Continuous erythropoietin receptor activator, hGH antagonist B2036, Insulin, Insulin human inhalation, Insulin aspart, Insulin glulisine, Insulin lispro, Isophane insulin, Insulin detemir, Insulin glargine, Insulin zinc extended, Pramlintide acetate, Growth hormone (GH), Somatotropin, Mecasermin, Mecasermin rinfabate, Factor VIII. Factor IX, Antithrombin III (AT-iii), fibroblast growth factor (FGF), basic fibroblast growth factor (bFGF), vascular endothelial growth factor (VEGF), platelet derived growth factor (PDGF), Protein C concentrate, β-Gluco-cerebrosidase, Alglucosidase-α, Laronidase (α-L-iduronidase), Idursulphase (iduronate-2-sulphatase), Galsulphase, Agalsidase-β (human α-galactosidase A), α-1-

Proteinase inhibitor, Lactase, Pancreatic enzymes, lipase, amylase, protease, Adenosine deaminase, Pooled immunoglobulins, Human albumin, Erythropoietin, Epoetin-α, Darbepoetin-α, Sargramostim (granulocytemacrophage colony stimulating factor; GM-CSF), Oprelvekin (interleukin 11; IL11) Human follicle-stimulating hormone (FSH), Human chorionic gonadotropin (HCG), Lutropin-α, Type I alpha-interferon, interferon alfacon 1, consensus interferon, Aldesleukin (interleukin 2 (IL2), epidermal thymocyte activating factor (ETAF), Alteolase (tissue plasminogen activator: tPA), Reteplase (deletion mutein of tPA), Tenecteplase, Urokinase, Factor VIIa, Drotrecogin-α (activated protein C), Salmon calcitonin, Teriparatide (human parathyroid hormone residues 1-34), Exenatide, Octreotide, Dibotermin-α (recombinant human bone morphogenic protein 2; rhBMP2), Recombinant human bone morphogenic protein 7 (rhBMP7), Histrelin acetate (gonadotropin releasing hormone; GnrH), Palifermin (keratinocyte growth factor; KGF), Becaplermin (platelet-derived growth factor, PDGF), Trypsin, Nesiritide, Botulinum toxin type A, Botulinum toxin type B, Collages, Collagenase, Human deoxyribonuclease I, dornase-α, Hyaluronidase (bovine, ovine), Hyaluronidase (recombinant human), Papain, L-Asparaginase, Rasburicase, Lepirudin, Bivalirudin, Streptokinase, Anistreplase (anisoylated plasminogen streptokinase activator complex; APSAC), Bevacizumab, Cetuximab, Panitumumab, Alemtuzumab, Rituximab, Trastuzumab, Abatacept Anakinra, Adalimumab, Etanercept, Infliximab, Alefacept, Efalizumab, Natalizumab, Eculizumab, Antithymocyte globulin (rabbit), Basiliximab, Daclizumab, Muromonab-CD3, Omalizumab, Palivizumab, Enfuvirtide, Abciximab, Crotalidae polyvalent immune Fab (ovine), Digoxin immune serum Fab (ovine), Ranibizumab, Denileukin diftitox, Ibritumomab tiuxetan, Gemtuzumab ozogamicin, Tositumomab, and itositumomab.

A denatured protein can be fully denatured, or partially denatured or renatured such that the protein is in non-native form as unfolded protein and/or partially folded refolding intermediate(s). An aqueous solution or dried sample comprising denatured protein may contain one or more of these forms. A native protein is in a folded, functional conformation. Some protein may also be present in aqueous solution, or in a dried sample, in the form of contaminating aggregates and/or inclusion bodies.

The term "stability" refers to the maintenance of a protein or other biomolecule's native bioactivity function after storage. The present invention will provide stability of at least 70%, and preferably at least 80%, of the protein's function as compared to storage without a trehalose stabilizing agent under identical environmental conditions. It is envisioned that, for example, when a protein like insulin is conjugated with a trehalose-based polymer or copolymer as described here, the insulin protein retains at least 70%, 75%, 80%, 85%, 90% or greater percentage of its native bioactivity compared to insulin by itself, which may retain only 20% of its original bioactivity at best. Those skilled in the art appreciate that the percent of bioactivity that is retained is protein and stress dependent. Furthermore, the length of time that a conjugated protein is able to maintain its bioactivity or function compared to a naked/unmodified protein varies depending on the environmental stressors it is subjected to. It is envisioned the conjugated proteins as described here can retain bioactivity for at least 5, 10, 20, 30, 40, 50, 60, 70, 80, 90, or 100 times longer than an unconjugated native protein under identical environmental conditions.

The term "antibody" or "antibody molecule" as used herein refers to immunoglobulin molecules or other molecules which comprise an antigen binding domain. The term "antibody" or "antibody molecule" as used herein is thus intended to include whole antibodies (e.g., IgG, IgA, IgE, IgM, or IgD), monoclonal antibodies, polyclonal antibodies, and chimeric antibodies.

The terms "monoclonal antibody" or "monoclonal antibody composition" as used herein refer to a preparation of antibody molecules of a single amino acid composition. The monoclonal antibody also includes "human monoclonal antibody" which refers to antibodies displaying a single binding specificity which have variable and constant regions derived from human germline immunoglobulin sequences. The human monoclonal antibodies can be produced by a hybridoma which includes a B cell obtained from a transgenic nonhuman animal, for example, a transgenic mouse, having a genome comprising a human heavy chain trans gene and a light human chain transgene fused to an immortalized cell.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies can also comprise a murine variable region and a human constant region. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art.

The term "antibody" also shall include humanized antibody, human antibody and recombinant human antibody. The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." Particularly preferred CDRs correspond to those representing sequences recognizing the antigens noted above for chimeric and bifunctional antibodies.

The term "human antibody" includes antibodies having variable and constant regions derived from human germline immunoglobulin sequences. The variable heavy chain is preferably derived from germline sequence DP-50 and the variable light chain is derived from germline sequence L6. The constant regions of the antibody are constant regions of human IgG 1 type.

The term "recombinant human antibody" includes all human antibodies that are prepared, expressed, created or isolated by recombinant means, such as antibodies isolated from a host cell such as an SP2-0, NSO or CHO cell (like CHO Kl) or from an animal (e.g., a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form.

The term "antibody" also includes "antibody fragments" or "antibody-derived fragments" which comprise an antigen binding domain are also included. The term "antibody fragment" as used herein is intended to include any appropriate antibody fragment that displays antigen binding function, for example, Fab, Fab', F(ab')2, scFv, Fv, dsFv, ds-scFv, Fd, dAbs, TandAbs dimers, mini bodies, monobodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

The antibodies or antibody fragments can be produced naturally or can be wholly or partially synthetically produced. Thus the antibody may be from any appropriate source, for example recombinant sources and/or produced in transgenic animals or transgenic plants. Thus, the antibody molecules can be produced in vitro or in vivo. Preferably the antibody or antibody fragment comprises an antibody light chain variable region ($V_L$) and an antibody heavy chain variable region ($V_H$) which generally comprise the antigen binding site. The antibody or antibody fragment can comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region. Furthermore, the antibody or antibody fragment can comprise all or a portion of a kappa light chain constant region or a lambda light chain constant region. All or part of such constant regions may be produced naturally or may be wholly or partially synthetic. Appropriate sequences for such constant regions are well known and documented in the art.

The term "fragment" as used herein refers to fragments of biological relevance (functional fragment), e.g., fragments which can contribute to or enable antigen binding, e.g., form part or all of the antigen binding site, or can contribute to the inhibition or reduction in function of the antigen or can contribute to the prevention of the antigen interacting with its natural ligands. Fragments thus comprise a heavy chain variable region ($V_H$ domain) and/or a light chain variable region ($V_L$ domain) of the antibodies of the invention. Fragments may also comprise one or more of the heavy chain complementarity determining regions (CDRs) of the antibodies or of the $V_H$ domains, or one or more of the light chain complementarity determining regions (CDRs) of the antibodies, or of the $V_L$ domains.

The term "sugar polymer" as used herein encompasses polymeric and oligomeric saccharide molecules comprising three or more mono-, di- or tri-saccharide units. The sugar polymer can be a linear or non-linear amphipathic sugar polymer derivative. Specifically, sugar polymers comprise one or more sugar(s) including, without limitation, trehalose, erythrose, threose, ribose, arabinose, xylose, lyxose, allose, altrose, glucose, mannose, gulose, idose, galactose, talose, psicose, fructose, sorbose, tagatose, xylulose and ribulose. The sugar polymers can be a dextran, cellulose, amylose, starch, pullulan, mannan, chitin, chitosan, inulin, levan, xylan, cyclodextrin (provided that it is not an alpha, beta or gamma cyclodextrin), cycloamylose or a derivative thereof.

Sugar polymers, specifically trehalose-based homopolymer or copolymers suitable for use in the invention are those which, at an appropriate concentration and in appropriate conditions, can (1) maintain a native biomolecule in its native state to retain a functional property of the native biomolecule in a stressful environment or (2) maintain a denatured biomolecule in a non-native state as desired by the researcher. Suitable trehalose-based homopolymer or copolymers are those which are capable of shielding hydrophobic amino acid side chains or modifying the net biomolecule charge or hydrogen bonding characteristics. Suitable trehalose-based homopolymer or copolymers may also comprise those capable of water entrapment, or those having hydrogen bonding characteristics.

The term "hydrogel," as used herein, refers to a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content.

Hydrogels are three-dimensional networks made of hydrophilic polymers or polymers containing hydrophilic co-polymers. Hydrogel networks are formed by the cross-linking of polymer chains via covalent bonds, hydrogen bonds, or ionic interactions, or via physical entanglement. Hydrogels can be prepared with biocompatible synthetic materials to achieve specific properties at the micro- or nano-scale level. The manipulation of the molecular weight or molecular weight distribution can be used to modulate the mechanical strength of hydrogels to satisfy different requirements. Hydrogels can be designed to modulate the porosity of the network, which can be advantageously used to control the release rate. Hydrogels can be designed in a wide variety of shapes as desired. Depending on the requirements, hydrogels can be prepared in different format of geometry such as particles, films, coatings, cylinders and slabs for in vitro and/or in vivo uses.

Hydrogels can be formed from a wide variety of biocompatible polymeric materials, including, but not limited to, polyurethane, silicone, copolymers of silicone and polyurethane, polyolefins such as polyisobutylene and polyisoprene, nitrile, neoprene, collagen, alginate and the like. For example, suitable hydrogels can be formed from polyvinyl alcohol, acrylamides such as polyacrylic acid and poly(acrylonitrile-acrylic acid), polyurethanes, polyethylene glycol, poly(N-vinyl-2-pyrrolidone), acrylates such as poly(-hydroxy ethyl methacrylate) and copolymers of acrylates with N-vinyl pyrrolidone, N-vinyl lactams, a poly(lactide-co-glycolide), acrylamide, polyurethanes, polyacrylonitrile, poloxamer, N-Isopropylacrylamide copolymers, poly(N-isopropylacrylamide), poly(vinyl methyl ether), poly(NIPAAm-co-PEG) and the like.

Suitable hydrogels can be formed from ABA triblock containing hydrophobic polyester (A-block) and hydrophilic polyether, triblock copolymer of poly(D,L-lactide-block-ethylene oxide-block-D,L-lactide) PLA-PEO-PLA, triblock copolymer of poly(L-lactide-block-ethylene oxide-block-L-lactide) PLLA-PEO-PLLA, triblock copolymer of poly[(D,L-lactide-coglycolide)-block-ethylene oxide-block-(D,L-lactide-co-glycolide)] PLGA-PEO-PLGA, triblock copolymer of poly[(L-lactide-coglycolide)-block-ethylene oxide-block-(L-lactide-co-glycolide)] PLLGA-PEO-PLLGA, triblock copolymer of poly[(D,L-lactide-coglycolide)-block-ethylene oxide-block-(D,L-lactide-co-glycolide)] PLGA-PEO-PLGA, triblock copolymer of poly(ε-caprolactone-block-ethylene oxide-block-ε-caprolactone)

PCL-PEO-PCL, triblock copolymer of poly[(D,L-lactide-co-ε-caprolactone)-block-ethylene oxide-block-(D,L-lactide-co-ε-caprolactone)] PLC-PEO-PLC. Applicants envision that any other triblock copolymer as appreciated by one skilled in the art may also be used for the present invention.

Hydrogels can be prepared with natural biomolecules. For example, suitable natural hydrogels can be formed from gelatin, agarose, amylase, amylopectin, cellulose derivatives such as methylcellulose, hyaluronan, chitosan, carrangenans, collagen, Gellan®, alginate and other naturally derived polymers. For example, collagen can be used to form hydrogel. Collagen can be used to create an artificial extracellular matrix that can be used as cell infiltration scaffolds for inducing tissue regeneration and remodeling. Suitable natural hydrogels also include alginate. Alginate is natural polysaccharide extracted from algae or produced by bacteria. Alginate can be a linear anionic polymer composed of 1,4-linked β-D-mannuronic acid and α-L-guluronic acid residues. In one embodiment, biocompatible alginate form hydrogels in the presence of divalent cations (e.g., $Ca^{2+}$). Accordingly, the synthesis of alginate hydrogels can be carried out in a physiological condition where the proteins whose release is to be controlled retain their natural function. Alginate hydrogels can be used for encapsulation of functionalized aptamer-coated beads and to be used in controlled release of the protein for tissue regeneration, and protein delivery in vitro and in vivo. In another embodiment, agarose can be used to form a hydrogel.

Hydrogels have been extensively used as drug delivery vehicles with biomedical applications (Roy, I.; Gupta, M. N. Chem. Biol. 2003, 10, 1161-1171). "Smart hydrogels", which respond to specific triggers, can be synthesized to deliver and release guest drugs into a specifically targeted site (Bajpai, A. K.; Shukla, S. K.; Bhanu, S.; Kankane, S. Prog. Polym. Sci. 2008, 33, 1088-1118; Gupta, P.; Vermani, K.; Garg, S. Drug Discov. Today 2002, 7, 569-579; Qiu, Y.; Park, K. Adv. Drug Delivery Rev. 2001, 53, 321-339; Kiyonaka, S.; Sugiyasu, K.; Shinkai, S.; Hamachi, I. J. Am. Chem. Soc. 2002, 124, 10954-10955; Mano, J. F. Advanced Engineering Materials 2008, 10, 515-527). In particular, pH responsive hydrogels are frequently used in drug delivery because different cell types and compartments of cells have discrete pHs, which allows for site specific release of a payload. For example, the pH of the extracelluar matrix (ECM) is typically around 7.4, while the cytosol has a lower pH and cancer cells are also more acidic than normal cells (Ingber, D. E.; Prusty, D.; Frangioni, J. V.; Cragoe, E. J.; Lechene, C.; Schwartz, M. A. J. Cell Biol. 1990, 110, 1803-1811; Wei, F.; Zhuyuan, W.; Shenfei, Z.; Hui, C.; Dan, Z.; Yuan, Z.; Yiping, C. Biosens. Bioelectron. 2014, 57, 10-15). Moreover, the pH in the stomach is between pH 2 and 4 depending on whether the stomach is empty or food has been injested (Qiu, Y.; Park, K. Adv. Drug Delivery Rev. 2001, 53, 321-339). Therefore research on pH responsive hydrogels is an important field of interest. Significant research has been reported toward the oral administration of therapeutics using pH responsive hydrogels. These hydrogels target the stomach for site-specific delivery of antibiotic, therapeutic proteins, and peptides (Lowman, A. M.; Morishita, M.; Kajita, M.; Nagai, T.; Peppas, N. A. J. Pharm. Sci. 1999, 88, 933-937; Patel, V.; Amiji, M. Pharm. Res. 1996, 13, 588-593; Besheer, A.; Wood, K. M.; Peppas, N. A.; Mader, K. J. Control. Release 2006, 111, 73-80; Guo, B.-L.; Gao, Q.-Y. Carbohydr. Res. 2007, 342, 2416-2422; Nho, Y. C.; Park, S. E.; Kim, H. I.; Hwang, T. S. Nuclear Instruments & Methods in Physics Research Section B-Beam Interactions with Materials and Atoms 2005, 236, 283-288. Sajeesh, S.; Sharma, C. P. Journal of Biomedical Materials Research Part B-Applied Biomaterials 2006, 76B, 298-305; Shantha, K. L.; Harding, D. R. K. Int. J. Pharm. 2000, 207, 65-70). Because the target site is the stomach, the hydrogels must only release their therapeutics in conditions more acidic than pH 3. This release occurs by changing the degree of swelling in the hydrogel or by cleaving the cross-linker.

A hydrogel may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and that a substantial fraction of these pores are of dimensions between 1 nm and 10 µm.

The term "crosslink" or "cross-linker," as used herein, refers to a molecule that is capable of linking at least one second molecule to at least one third molecule through either covalent bonds or ionic bonds. In one embodiment, at least one of the second or the third molecule is a polymer. In one embodiment, the cross-linker is an armed PEG or a star PEG.

The term "trehalose cross-linker," as used herein, refers to a cross-linker comprising at least one trehalose group.

The term "boronic acid-based cross-linker," as used herein, refers to a compound or cross-linker, which is produced from the reaction of a boronic acid with another compound. The other compound generally has a typical structure for cross-linking, e.g., multi-armed PEG structures.

The term "polyethylene glycol" or "PEG," as used herein refers to a polyether compound with many applications from industrial manufacturing to medicine. The structure of PEG is: $H-(O-CH_2-CH_2)_n-OH$.

The term "armed PEGs" or "branched PEGs," or "multi-armed PEGs" as used herein, refers to PEGs that have three to ten PEG chains emanating from a central core group. The term "star PEGs" refers to PEGs that have 10 to 100 PEG chains emanating from a central core group.

The term "trehalose-based monomer," as used herein, refers to a monomer including at least one trehalose which is covalently bound to the side chain of the monomer. The controlled in vivo delivery of biomolecules while maintaining stability is critical for their efficient therapeutic use. Interest in boronic acid containing hydrogels for applications in a wide variety of biomedical fields is growing (Cambre, J. N.; Sumerlin, B. S. Polymer 2011, 52, 4631-4643; Guan, Y.; Zhang, Y. Chem. Soc. Rev. 2013, 42, 8106-8121; Ravaine, V.; Ancla, C.; Catargi, B. J. Control. Release 2008, 132, 2-11). Because boronic acids form reversible covalent complexes with 1,2- or 1,3-diols their incorporation into hydrogels results in glucose-responsive materials (Kuivila, H. G.; Keough, A. H.; Soboczenski, E. J. J. Org. Chem. 1954, 19, 780-783; Springsteen, G.; Wang, B. H. Tetrahedron 2002, 58, 5291-5300; Yan, J.; Springsteen, G.; Deeter, S.; Wang, B. Tetrahedron 2004, 60, 11205-11209; Barker, S. A.; Chopra, A. K.; Hatt, B. W.; Somers, P. J. Carbohydr. Res. 1973, 26, 33-40). Due to this glucose-responsive moiety, these hydrogels are commonly used as devices for insulin delivery (Matsumoto, A.; Yamamoto, K.; Yoshida, R.; Kataoka, K.; Aoyagi, T.; Miyahara, Y. Chem. Commun. 2010, 46, 2203-2205; Wang, D.; Liu, T.; Yin, J.; Liu, S. Macromolecules 2011, 44, 2282-2290; Ancla, C.; Lapeyre, V.; Gosse, I.; Catargi, B.; Ravaine, V. Langmuir 2011, 27, 12693-12701; Matsumoto, A.; Ishii, T.; Nishida, J.; Matsumoto, H.; Kataoka, K.; Miyahara, Y. *Angewandte Chemie-International Edition* 2012, 51, 2124-2128; Zhang, C.; Losego, M. D.; Braun, P. V. *Chem. Mater.* 2013, 25, 3239-3250; Yuan, W.; Shen, T.; Wang, J.; Zou, H. *Polymer Chemistry* 2014, 5, 3968-3971; Yang, T.; Ji, R.; Deng, X.-X.; Du, F.-S.; Li, Z.-C. *Soft Matter* 2014, 10, 2671-2678). The majority of these insulin delivery boronic acid hydrogels were prepared by co-polymerizing boronic acid and cross-linkable monomers to form a hydrogel that swells in the presence of glucose, thereby releasing insulin.

The term "one-pot synthesis," as used herein, refers to a strategy to improve the efficiency of a chemical reaction whereby a reactant is subjected to successive chemical reactions in just one reactor. This is much desired by chemists because avoiding a lengthy separation process and purification of the intermediate chemical compounds would save time and resources while increasing chemical yield and reducing waste.

THE INVENTION

The present invention discloses novel biocompatible affinity porous matrix compositions, formulations and methods for controlling release of biomolecules (e.g., peptides or proteins) suitable for a wide range of medical, pharmaceutical and agricultural applications. The present invention generally relates to a technology that provides easy-to-manufacture and reproducible compositions and formulations for peptide or protein release. In one embodiment, the novel biocompatible affinity porous matrix composition is a hydrogel.

Specifically, the present invention relates to hydrogels, in particular trehalose-based hydrogels. In one embodiment, the present invention relates to hydrogels for protecting and controlled releasing a peptide or protein. In one specific embodiment, the peptide or protein is an insulin.

In view of the fact that exposure of insulin to changes in temperature during storage may lead to inactivation of the protein resulting in health complications, the present invention discloses hydrogels and methods of using hydrogels for stabilizing insulins under enhanced temperatures. Specifically, the present invention discloses hydrogels and methods of using hydrogels to enhance thermal and mechanical stability of insulin. At the same time, the present invention also discloses hydrogels and methods of using hydrogels to controlled release insulins.

For example, the present invention discloses methods of making trehalose-based hydrogels for stabilizing insulin molecules, wherein the insulin molecules may be covalently or non-covalently attached to the hydrogels. Such hydrogels are responsive to the surrounded environments, e.g., the presence of glucose. Thus, by controlling the surrounded environments, e.g., glucose concentration, insulin may be released in a controlled manner from the present hydrogels.

In another embodiment, the peptide or protein is a feed enzyme such as phytase.

In view of the fact that the conversion of phytic acid is essential for simple-stomached species such as swine, poultry, and fish to utilize this storage form of phosphate present in common feed grains such as corn, soy, and wheat, the present invention discloses hydrogels and methods of using hydrogels for stabilization of enzymes (e.g., phytase) under elevated temperatures (e.g., higher than room temperature).

In one specific embodiment, the present invention relates to a trehalose-based hydrogel that can be synthesized in two steps from commercial starting materials with minimal purification procedures. In one embodiment, mono- and multi-functional trehalose monomers may be cross-linked by redox-initiated radical polymerization to form a hydrogel. In one specific embodiment, phytase, an important enzyme utilized in animal feedstock, may be used to show the effectiveness of the trehalose hydrogel to stabilize proteins against heat.

For example, addition of the phytase solution to the hydrogel resulted in enzyme internalization as confirmed by confocal microscopy. The phytase in the hydrogel retained 100% activity upon heating at 90° C. compared to 39% when the hydrogel was absent. The enzyme could also be recovered from the hydrogel. Applicants envision that the trehalose hydrogel synthesis reported herein should be readily scalable for thermal stabilization of a wide variety of enzymes.

Specifically, as described below, Applicants found that phytase retains 100% activity when heated to 90° C. in the presence of trehalose hydrogels. Example 3 show the detail experiments of hydrogels for protecting and controlled releasing a peptide or protein, e.g., phytase.

In one aspect, the present invention discloses a method for creating a trehalose-based hydrogel. Such trehalose-based hydrogels may be used to stabilize and deliver a protein. In one specific embodiment, the protein is an insulin. In one embodiment, the protein (e.g., insulin) may be added before the preparation of trehalose-based hydrogels. In one embodiment, the protein (e.g., insulin) may be added during the preparation of trehalose-based hydrogels. In one embodiment, the protein (e.g., insulin) may be added after the preparation of trehalose-based hydrogels.

In one specific embodiment, the protein is a feed enzyme such as phytase. In one embodiment, the enzyme (e.g., phytase) may be added before the preparation of trehalose-based hydrogels. In one embodiment, the enzyme (e.g., phytase) may be added during the preparation of trehalose-based hydrogels. In one embodiment, the enzyme (e.g., phytase) may be added after the preparation of trehalose-based hydrogels.

In one embodiment, a method of creating a trehalose-based hydrogel, comprising the steps of (a) forming a trehalose homopolymer or co-polymer, (b) preparing a cross-linker; and (c) reacting the trehalose homopolymer or co-polymer with the cross-linker to form the trehalose-based hydrogel.

In one embodiment of the present method, a trehalose-based hydrogel is used for stabilizing and delivering a protein. In one embodiment, the protein may be added before the preparation of trehalose-based hydrogels. In one embodiment, the protein may be added during the preparation of trehalose-based hydrogels. In one embodiment, the protein may be added after the preparation of trehalose-based hydrogels.

In one embodiment, the trehalose homopolymers or co-polymers have the general structures of $R_5-[R_1R_2C-CR_3R_4]_n-R_6$, wherein $R_1$-$R_4$ are independently selected from hydrogen or a side chain comprising at least one carbon atom, and wherein at least one of $R_1$-$R_4$ is a side chain comprising -L-trehalose, wherein L is a linker molecule that links trehalose to the monomer through at least one of the trehalose hydroxyl groups (—OH), and wherein $R_5$ and $R_6$ are independently selected from the group consisting of -Alkyl, -Alkenyl, -Alkynyl, -aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), and biomolecules.

Applicants' previous patent application WO 2013/112897 disclosed methods of making trehalose homopolymers or co-polymers. Applicants envision that other trehalose homopolymers or co-polymers may also be suitable for the present invention.

In one embodiment, the cross-linkers are either polyethylene glycols or polyethylene glycol (PEG) derivatives. Preferably, the cross-linkers are polyethylene glycol (PEG) derivatives with multiple arms. One exemplary polyethylene glycol (PEG) derivative is shown in Scheme 1.

In one embodiment, the cross-linker in the present invention is a boronic acid-based compound. Boronic acid is biocompatible and can reversibly bind to glucose, making it a promising moiety for insulin delivery. Boronic acid binding to diol is pH dependent, with the boronate form mainly responsible for binding to sugars. A cross-linker based on boronic acid is able to bind to the diols in the trehalose polymer. Upon addition of glucose, the glucose can displace trehalose polymer due to its higher binding affinity with the borate.

In one embodiment, the boronic acid that is suitable for the present invention has a structure of R—B(OH)$_2$, wherein R=aryl, alkyl or alkenyl. In one preferred embodiment, R=aryl. Applicants envision that any structurally similar compounds including the heteroaryl counterparts may also be used for the present invention.

In one specific embodiment, the boronic acid-based cross-linker is a poly(ethylene glycol) (PEG)-boronic acid cross-linker.

For example, 8-arm PEG amine may be functionalized with boronic acid via reductive amination. Scheme 1 outlines the reaction of 8-arm PEG amine with boronic acid to form one exemplary boronic acid-based cross-linker. Example 1 includes the detail materials and synthetic procedures for the reactions in Scheme 1.

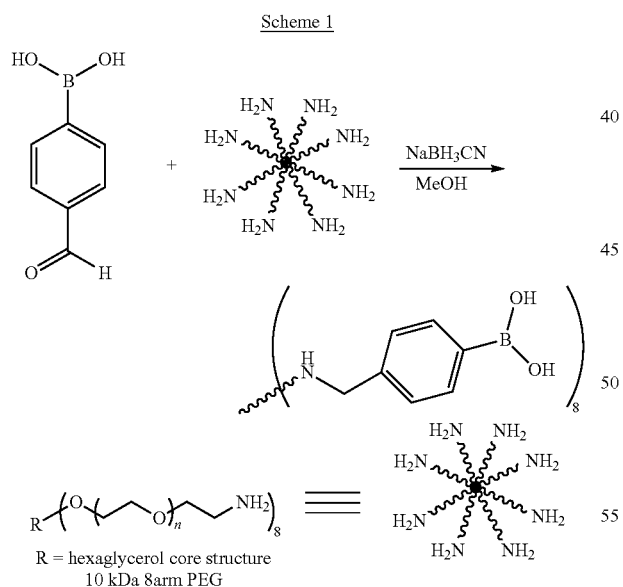

Applicants envision that other PEG compounds with similar structures to 8-arm PEG amine may be used to produce suitable boronic acid-based cross-linkers. For example, any armed PEG (e.g., 2, 3, 4, 5, 6, 7, 9, or 10-arm PEG) may be used for the present invention. For example, any star PEG (e.g., 10-1000, preferably 10-500, more preferably 10-100 arm PEG) may also be used for the present invention.

In one embodiment, the present trehalose-based hydrogel may be produced by a reaction of any trehalose homopolymer or co-polymer with a boronic acid-based cross-linker. Any trehalose homopolymer or co-polymer such as those described in WO 2013/112897 may be suitable for the present invention. Any boronic acid-based cross-linker that can be similarly synthesized as Scheme 1 may be suitable for the present invention.

A trehalose homopolymer or co-polymer that can be used for the present invention may include any trehalose-based polymeric compound. In one embodiment, the trehalose homopolymer or co-polymer may be a PEG-based polymer or a polystyrenyl backbone polymer or polymethacrylate-based polymer or poly(N-isopropylacrylamide)-based polymer.

Scheme 2 shows the reaction of one exemplary trehalose homopolymer or co-polymer, poly(styrenyl ether trehalose) (poly(SET) with one exemplary boronic acid-based cross-linker, 8 Arm PEG Boronic Acid, to form poly(SET)-boronic acid hydrogel. Example 1 includes the detail materials and synthetic procedures for the reactions in Scheme 2.

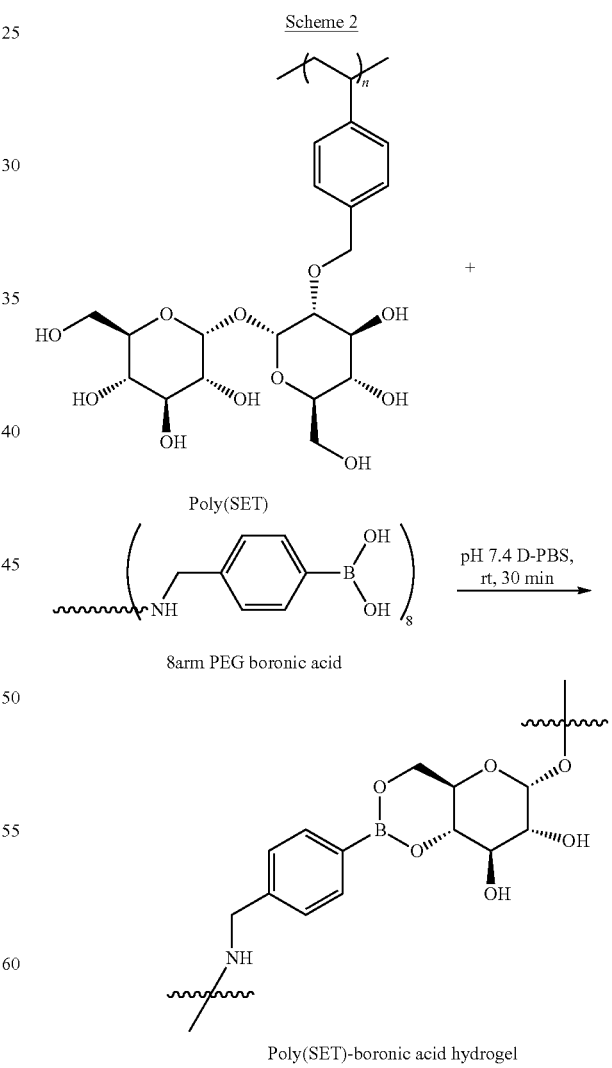

In one embodiment, the present trehalose-based hydrogel may be synthesized under physiological conditions. For example, the reaction between a trehalose homopolymer or co-polymer (e.g., poly(styrenyl ether trehalose) (poly(SET)) and a boronic acid-based cross-linker may occur under the conditions of neutral pHs (e.g., pH 7.4) and room temperature. In one embodiment, the reaction occurs rapidly, e.g., within minutes.

In one embodiment, the ratio of a trehalose homopolymer or co-polymer to a boronic acid-based cross-linker in the reaction is about 1:1.

In one embodiment, present trehalose-based hydrogel may be responsive to the surrounded environments, e.g., the presence of glucose.

Figure 3:
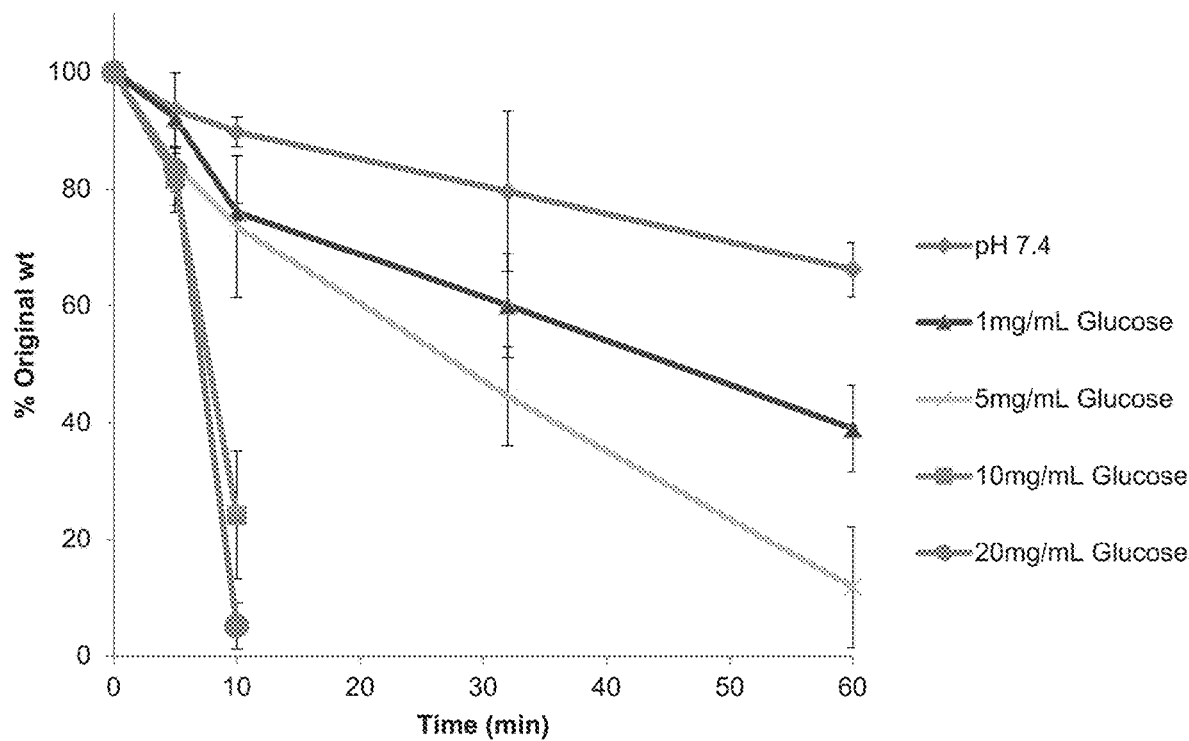
FIG. 3 is a graph showing dissolution kinetics of Poly-SET-boronic acid hydrogels after immersing into D-PBS containing 0, 1, 5, 10, and 20 mg/mL glucose (n=3 per group).

As shown in Example 1, Applicants demonstrate that the poly(SET)-boronic acid hydrogel is responsive for glucose. FIG. 3 shows that the addition of glucose led to de-cross-linking of the boronic ester bond between trehalose (polymer) and boronic acid (cross-linker) by competitive replacement of glucose-boronic acid complex due to the higher binding affinity of glucose to phenylboronic acid.

Figure 4:
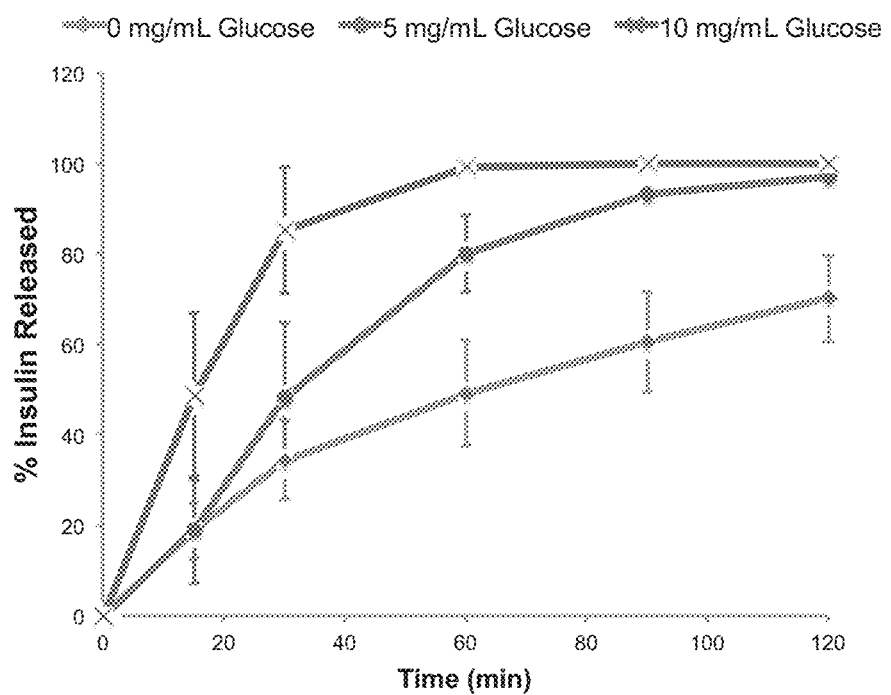
FIG. 4 is a graph showing insulin released in D-PBS, pH 7.4, containing 0, 5, and 10 mg/mL glucose (n=6 per group).

FIG. 4 shows that in the presence of glucose the hydrogel released insulin more rapidly. For example, After one hour, the hydrogel in 10 mg/mL glucose solution was completely dissolved to yield 100% insulin release, while over the same time period 80% and 49% insulin were released in 5 mg/mL and 0 mg/mL glucose solution, respectively. As such, Applicants demonstrate that these gels can be utilized for insulin delivery applications.

Figure 5:
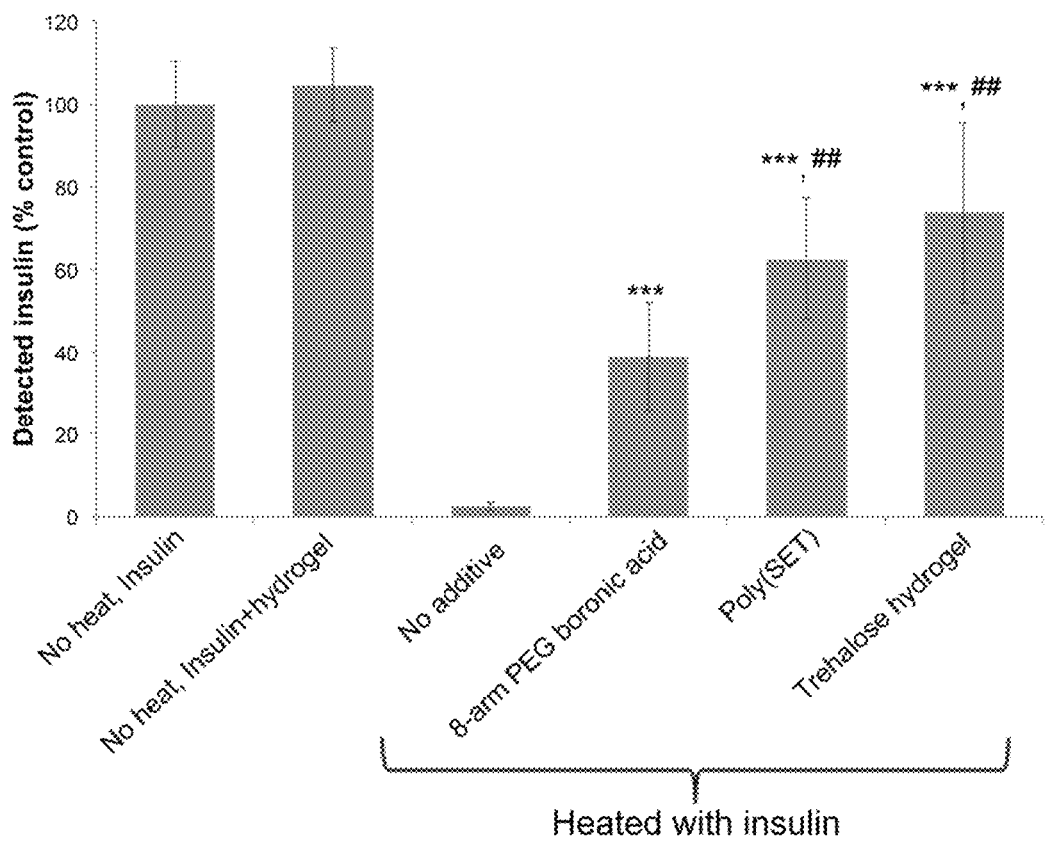
FIG. 5 is a graph showing ELISA results of insulin (no heat control), insulin with hydrogel (no heat control), insulin with no additive (heated), insulin with 8-arm PEG boronic acid (heated), insulin with trehalose polymer (heated), and insulin with hydrogel (heated). Heating condition was 90° C. for 30 min. *** is p<0.001 relative to no additive, ## is p<0.01 relative to 8-arm PEG boronic acid (n=6).

FIG. 5 shows that the glucose-responsive trehalose hydrogel is effective at stabilizing insulin against heating stress. For example, Applicants demonstrate that the trehalose-based hydrogels remarkably stabilized insulin and 63% of the original protein was detected after heating to 90° C. for 30 min. Insulin was also partially stabilized in the presence of the 8-arm PEG boronic acid alone (39% signal). As such, Applicants also showed that the trehalose-based hydrogels can be utilized to stabilize insulin.

In one aspect, the present invention discloses methods of stabilizing and delivering a protein (e.g., an insulin or an animal feed stabilizer) by using the trehalose-based hydrogels as discussed above.

In one embodiment, a method of stabilizing and delivering a protein, comprising the steps of a) preparing a trehalose-based hydrogel according to any method as disclosed herein; b) adding a protein into the trehalose-based hydrogel either at the time of hydrogel formation or after the formation to form a complex of the protein and the trehalose-based hydrogel; and c) adding a sugar solution into the complex of the protein and the trehalose-based hydrogel or lowering the pH of the solution to release the protein from the complex.

In one embodiment, the present invention relates to a composition and a method of applications of a trehalose-based hydrogel as discussed herein that remarkably stabilizes biomolecules to environmental stressors by mixing a suitable amount of a trehalose-based hydrogel with the biomolecule. In this embodiment, the formation of chemical bonds between the trehalose-based hydrogel and the biomolecule are not necessary. The trehalose-based hydrogels are not covalently attached to the biomolecule, but added as an excipient.

A suitable concentration of the trehalose-based hydrogel may be 50 μg/mL, 75 μg/mL, 100 μg/mL, 200 μg/mL, 300 μg/mL, 400 μg/mL, 500 μg/mL, 700 μg/mL, 900 μg/mL, 1 mg/mL, or 5 mg/mL, preferably 100 μg/mL. A suitable ratio of the polymers or co-polymers to biomolecule may be 1:1, 10:1, 20:1, 50:1, 100:1, or 200:1, and preferable 50:1 or 100:1. In one embodiment, the preferred ratio of the polymers or co-polymers to biomolecule may be 1:1.

In another aspect, the present invention discloses methods of making pH responsive trehalose hydrogels. Such trehalose hydrogels may be used for "Smart hydrogels", which respond to specific triggers, can be synthesized to deliver and release guest drugs into a specifically targeted site. In one embodiment, the trehalose hydrogels are not only delivery vehicles but also stabilizers against environmental stressors during storage and transportation.

In one embodiment, the present pH responsive trehalose hydrogels may be produced by polymerization of a trehalose-based monomer in the presence of a trehalose-based cross-linker. In one embodiment, the polymerization reaction is either a Free Radical Polymerization or a Redox-Initiated Polymerization.

In one embodiment, a method of creating a pH responsive trehalose-based hydrogel, comprising the steps of a) preparing a trehalose cross-linker; b) preparing a trehalose-based monomer; and c) reacting the trehalose cross-linker with one trehalose-based monomer to form the trehalose -based hydrogel.

In one embodiment, the trehalose cross-linker is synthesized using similar methods as is used to prepare a trehalose-based monomer. Applicants' previous patent application WO 2013/112897 disclosed many trehalose-based monomers which can be used for the present invention.

Scheme 3 shows an exemplary reaction. Applicants envision that many ratios between acetal monomer and trehalose may be used to produce the trehalose cross-linker. In one specific embodiment, to increase the yield for the bis-functionalized crosslinker over the monomer, the molar ratio between acetal and trehalose is larger than one. For example, 2.2 molar equiv of 4-vinylbenzaldehyde diethyl acetal was added to the trehalose (Scheme 3). The bis-SAT crosslinker was prepared through transacetalization in a high yield (between 55% and 72%).

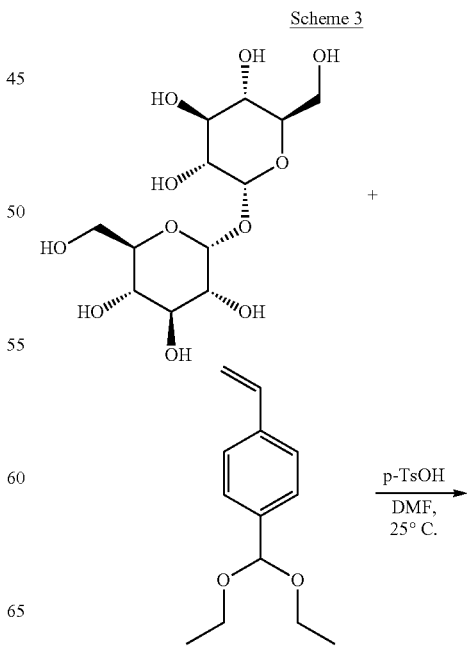

Scheme 3

-continued

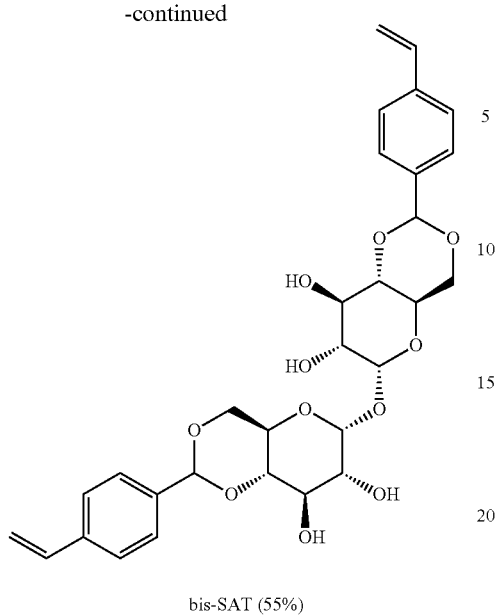

bis-SAT (55%)

Scheme 4

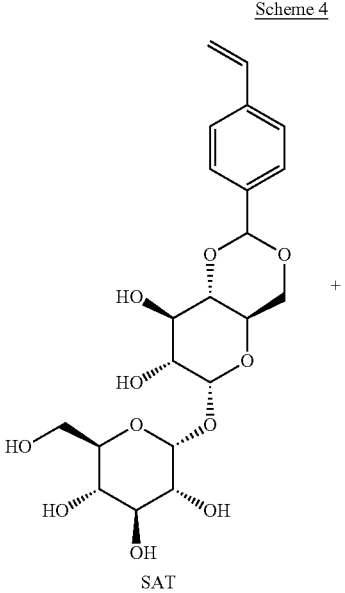

SAT

In one embodiment, a trehalose-based monomer is prepared. Applicants' previous patent application WO 2013/112897 disclosed many trehalose-based monomers which can be used for the present invention.

In one specific embodiment, the trehalose cross-linker is synthesized using an identical chemistry as that is used to prepare the trehalose-based monomer. For example, styrenyl acetal trehalose monomer (SAT) and styrenyl ether trehalose monomer (SET) may be used to prepare the pH responsive trehalose-based hydrogel.

In one embodiment, the trehalose cross-linker and the trehalose-based monomer may be co-polymerized under any suitable polymerization as appreciate by one skilled in the art. In one embodiment, the trehalose cross-linker and the trehalose-based monomer may be co-polymerized through a free radical polymerization. The free radical polymerization may be initiated by many ways including heat, redox, light, etc.

In one specific embodiment, the trehalose cross-linker and the trehalose-based monomer may be co-polymerized through either a heat initiated free radical polymerization or a redox-initiated free radical polymerization or photo-initiated free radical polymerization.

For example, as shown in Schemes 4 and 5, the bis-SAT crosslinker may be co-polymerized to form both SAT and SET hydrogels through heat initiated or redox initiated free radical polymerization. Example 2 outlines the detail synthetic procedures of the reactions.

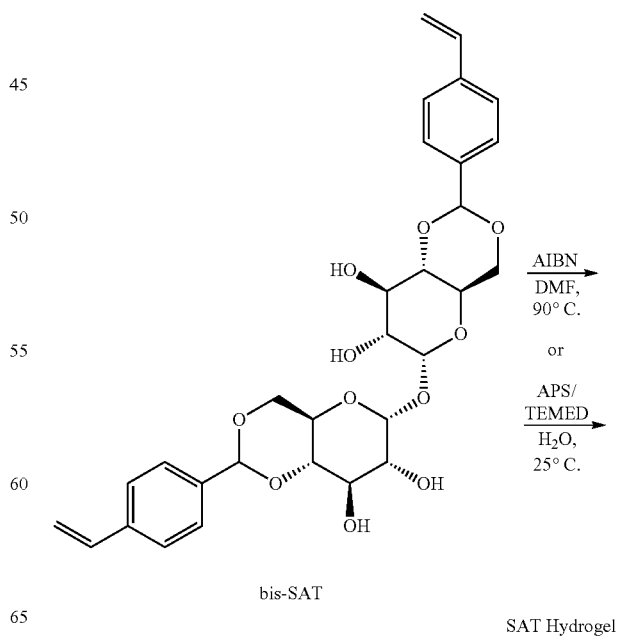

bis-SAT

SAT Hydrogel

-continued
Scheme 5

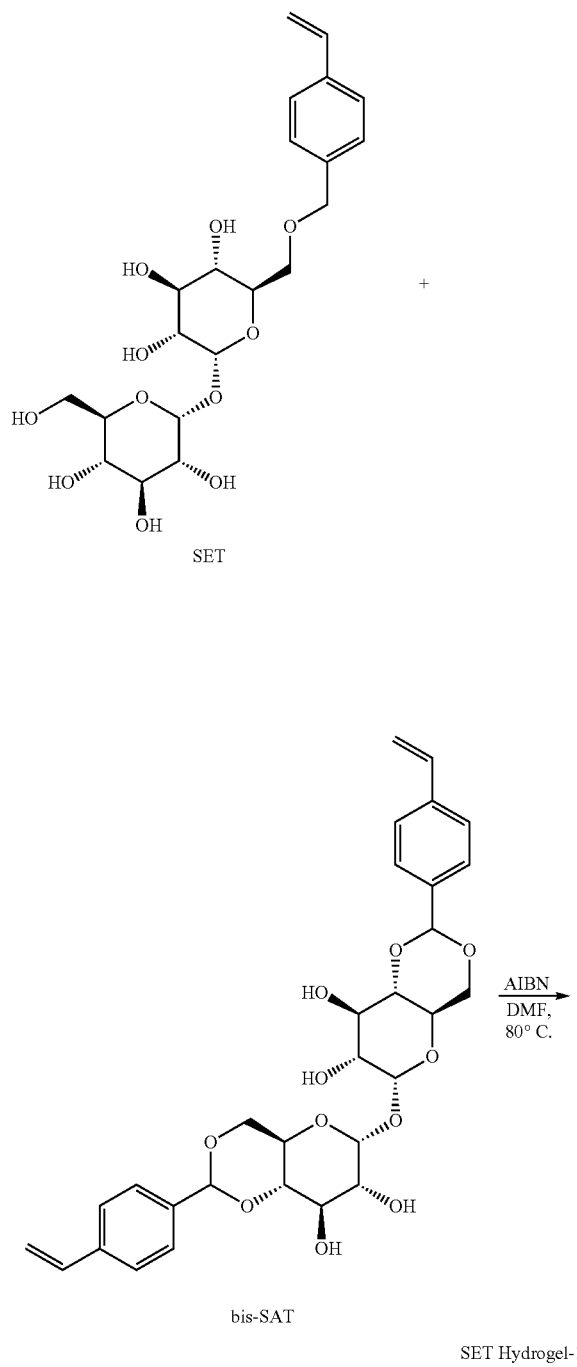

SET bis-SAT

SET Hydrogel-1

In one embodiment, the pH responsive trehalose hydrogels may be both protein delivery vehicles and protein stabilizers, e.g., against environmental stressors during storage and transportation.

In one specific embodiment, the pH responsive trehalose hydrogels may remain gelled in solutions when pH is greater than 5. In another embodiment, the pH responsive trehalose hydrogels dissolves in the solution when pH is smaller than 5.

Figure 9:
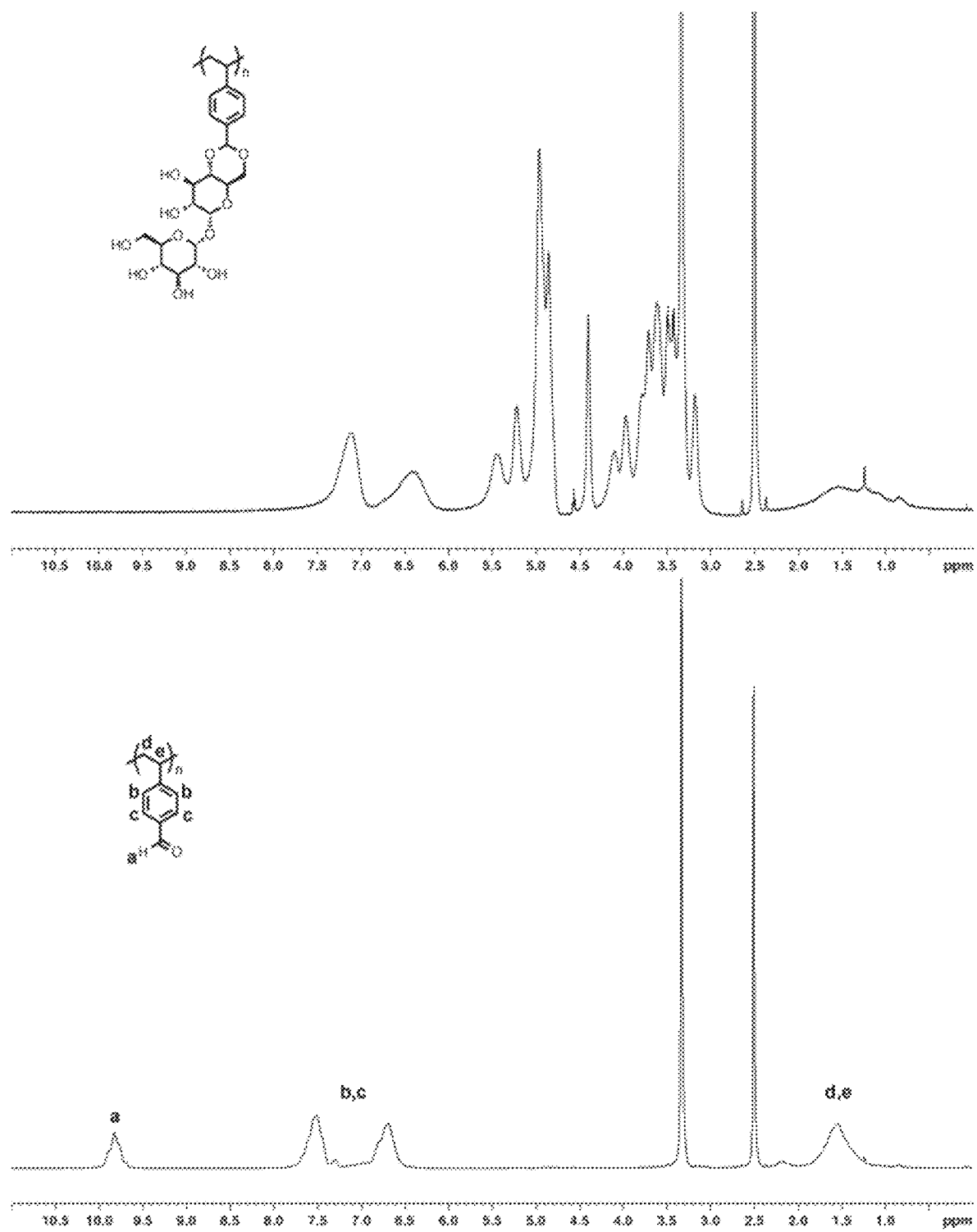
FIG. 9 is a set of graphs showing $^1$H NMR spectroscopy of poly(SAT) before (top) and after (bottom) treatment with 10% TFA aqueous solution (in $D_6DMSO$).

Example 2 shows exemplary pH responsive trehalose hydrogels and their properties. For example, FIG. 9 shows that poly(SAT) as an exemplary pH responsive trehalose hydrogel. As shown in FIG. 9, Poly(SAT) was dissolved in a series of acidic pHs to induce hydrolysis of the acetal linkage between trehalose and the pendant moiety in the polymer backbone. When the polymer was treated with 10% TFA, the $^1$H NMR peaks corresponding to the trehalose protons (FIG. 9; top; 3.0-5.5 ppm) disappeared and an aldehyde peak became visible. The $^1$H NMR spectrum of the resulting polymer appeared identical to the trace expected for a 4-benzaldehyde polymer (FIG. 9; bottom).

Figure 10:
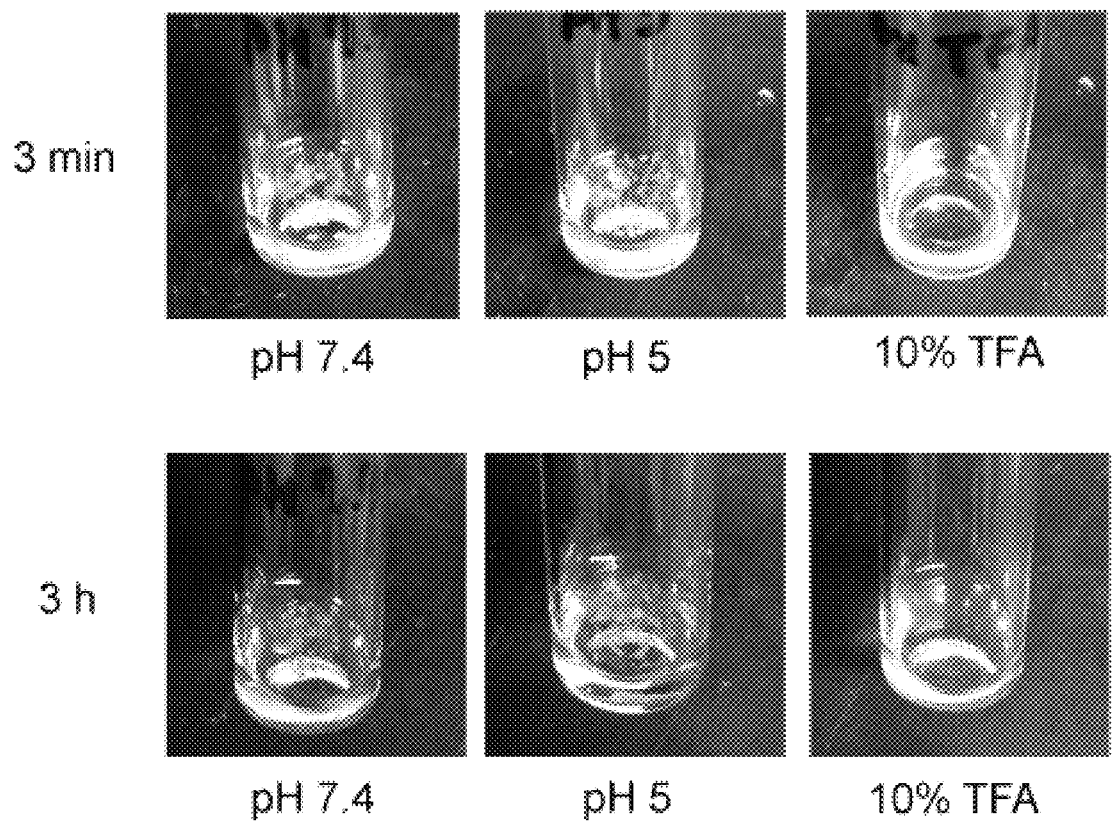
FIG. 10 is a set of photographs showing the stability studies of SET hydrogel-1 in pH 7.4 D-PBS, pH 5 PBS, and 10% TFA after 3 min (top) and 3 h incubation (bottom) at 25° C.

FIG. 10 shows another exemplary pH responsive trehalose hydrogel of SET hydrogel-1 and its property. While the hydrogel of poly(SAT) would not dissolve in aqueous buffer. the SET hydrogel-1 in 10% TFA dissolved completely within 3 min. The gel remained at both pH 7.4 and pH 5 even after 48 h incubation at 25° C. suggesting a low pH is required to reverse the acetal crosslinker linkage.

In one embodiment, the present pH responsive trehalose hydrogel may be used as vehicles for delivery of protein or peptide therapeutics to the stomach or stabilizers for enzymes used in acid triggered chemical synthesis and water purification.

In one embodiment, the protein may be added before the preparation of trehalose-based hydrogels. In one embodiment, the protein may be added during the preparation of trehalose-based hydrogels. In one embodiment, the protein may be added after the preparation of trehalose-based hydrogels.

In one embodiment, the protein may be an enzyme.

In one embodiment, the protein is stabilized when it is exposed to heat. In one embodiment, the protein is stabilized above 4° C. In one preferred embodiment, the protein is stabilized at 70-90° C.

In one aspect, the present invention relates to a hydrogel system based on the natural disaccharide trehalose as an efficient excipient to enhance the thermostability of proteins. In one embodiment, the trehalose hydrogel may be prepared in only two steps from trehalose using simple purification steps, which can be directly applied industrially for stabilization of proteins.

In one embodiment, a method of creating a trehalose-based hydrogel, comprising the steps of a) preparing trehalose cross-linkers and a trehalose-based monomer; and b) reacting the trehalose cross-linker with the trehalose-based monomer to form the trehalose-based hydrogel.

In one embodiment, trehalose cross-linkers and a trehalose-based monomer are produced through the same reaction. In one embodiment, trehalose cross-linkers may include di-substitutions and any other compounds that have degree of substitution (DS) over two.

In one embodiment, the trehalose cross-linkers and a trehalose-based monomer produced from the same reaction may not be purified. The reaction mixture including the trehalose cross-linkers and a trehalose-based monomer may be directly used for gelation.

In one embodiment, a trehalose-based hydrogel may include an one-pot synthesis. Specifically, the trehalose cross-linkers and a trehalose-based monomer may be produced from an one-pot reaction.

Scheme 6

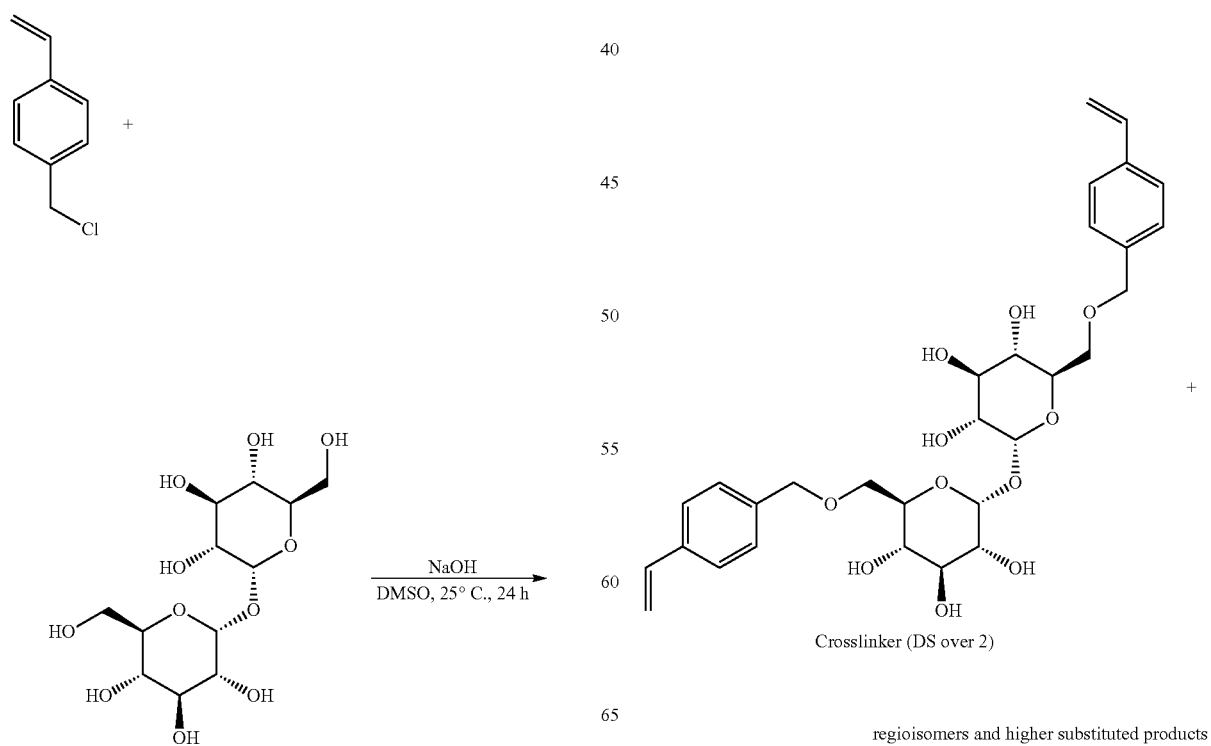

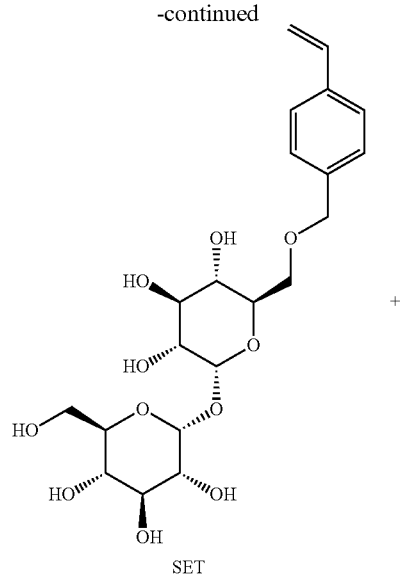

SET

Crosslinker (DS over 2)

regioisomers and higher substituted products

Scheme 7

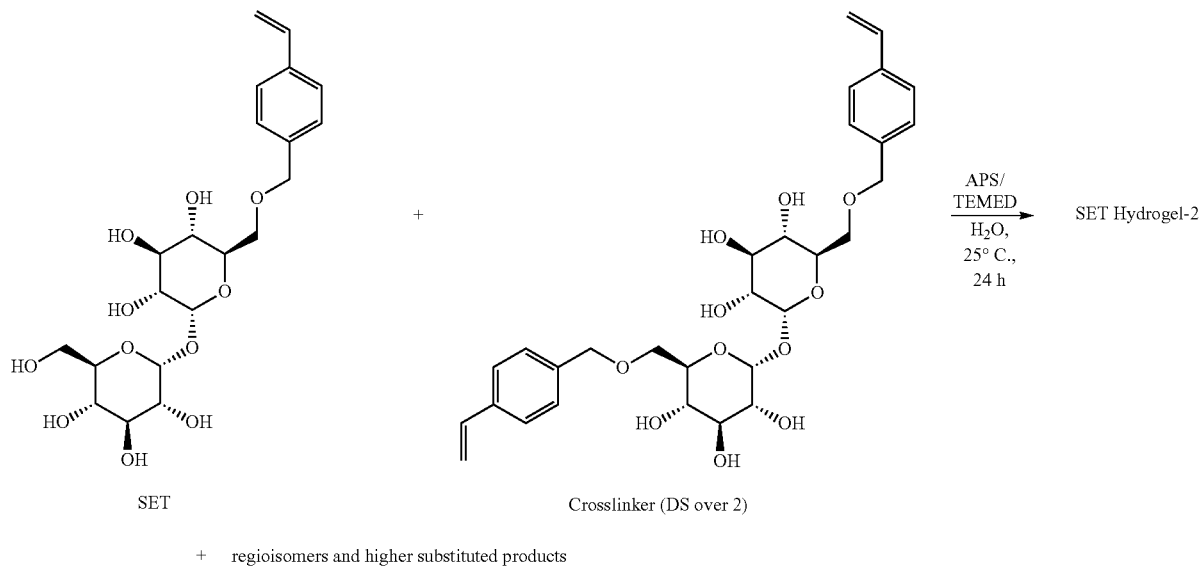

+ regioisomers and higher substituted products

Schemes 6 and 7 show one exemplary reaction for making trehalose-based hydrogels through an one-pot synthesis. Example 3 shows the detail synthetic procedure for producing trehalose-based hydrogels. Although a styrene-based monomer was used as an example, the present invention is applicable to other monomers as appreciated by one skilled in the art. For example, methacrylates may also be used in the present invention.

As shown in Scheme 6, both a trehalose-based monomer (e.g., SET) and trehalose cross-linkers can be produced from an one-pot reaction. In one embodiment, the resulting crude mixture of a trehalose-based monomer (e.g., SET) and trehalose cross-linkers may be precipitated into dichloromethane (DCM) and filtered to remove DMSO and trehalose with a high DS.

In one embodiment, the crude product of mixture may contain several regioisomers (e.g., trehalose with styrene at the $2^{nd}$, $3^{rd}$, $4^{th}$ and $6^{th}$ position), bis-functionalized and trifunctionalized trehalose, as well as unmodified trehalose. The crude SET may be then directly used for gelation.

In one embodiment, the trehalose-based hydrogels show substantial fraction of the pores that are of dimensions between 1 nm and 10 µm, preferably, 1-5 µm.

Figure 17:
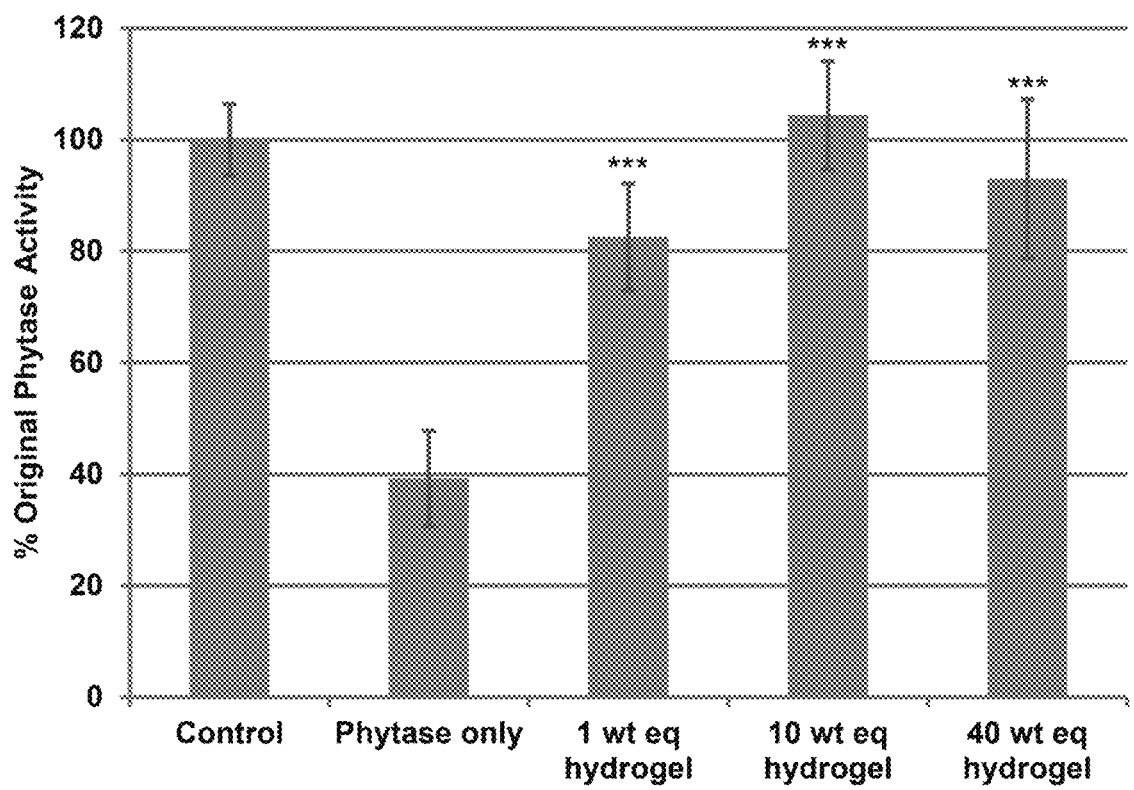
FIG. 17 is a graph showing activity of phytase after heating with different weight equivalents of trehalose hydrogel. All the samples except the control were heated for 1 min at 90° C. with 53 wt % of water (n=3). ***=$p<0.005$ relative to phytase only.
Figure 18:
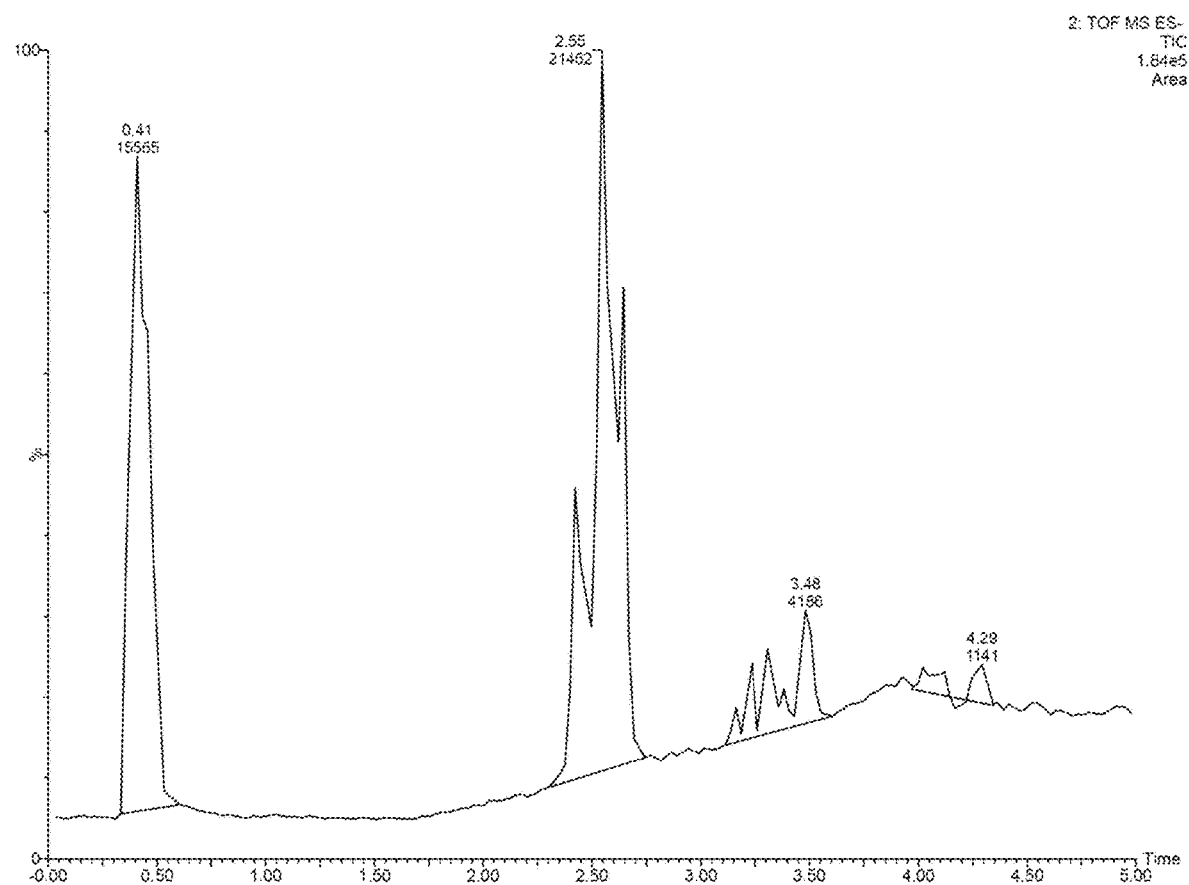
FIG. 18 a graph showing LC-MS chromatogram of crude styrenyl ether trehalose mixture after precipitation in DCM.

In one embodiment, the trehalose-based hydrogels can stabilize biomolecules (e.g., enzyme or phytase) against extreme heat conditions. As shown in FIG. 17, the results show that synthesis of a trehalose hydrogel for industrial-scale stabilization of proteins. The trehalose-based hydrogel may be prepared via simple synthesis and purification steps, which is a important consideration in industrial processes.

In one embodiment, the trehalose-based hydrogels may be used for stabilizing various enzymes or proteins against the pelleting procedure or other high-temperature processes.

In one embodiment, the present invention relates to a method of stabilizing a protein, comprising the steps of a) preparing a trehalose-based hydrogel according to any method as discussed above; and b) adding a protein into the trehalose-based hydrogel either at the time of hydrogel formation or after the formation to form a complex of the protein and the trehalose-based hydrogel, wherein the protein is stabilized.

In one embodiment, the protein is an enzyme.

In one embodiment, the protein is stabilized in the presence of heat. The present method can stabilize a protein when it is exposed to heat.

In one embodiment, the protein is stabilized above 4° C. In one embodiment, the protein is stabilized at 70-90° C.

In one embodiment, the protein is released from the complex of the protein and the trehalose-based hydrogel by diluting with water. In one embodiment, the protein is released from the complex of the protein and the trehalose-based hydrogel by lowering the pH value of the solution.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

EXAMPLES

Example 1

Trehalose Hydrogels for Stabilization and Delivery of Proteins

Materials

All chemicals were purchased from Sigma-Aldrich and Fisher Scientific. 8arm PEG amine was purchased from Jenkem Technology (Allen, Tex.). Trehalose was purchased from The Healthy Essential Management Corporation (Houston, Tex.), dried with ethanol and kept under vacuum before use. Azobisisobutyronitrile (AIBN) was recrystallized from acetone before use. Styrenyl ether trehalose monomer (SET) was prepared using previously reported procedures (Lee et al., 2013).

Analytical Techniques

NMR spectra were obtained on Bruker DRX 500 MHz spectrometers. $^1$H NMR spectra were acquired with a relaxation delay of 30 s for polymers.

NMR spectra were recorded on a Bruker DRX 500 MHz spectrometer. Gel permeation chromatography (GPC) was conducted on a Shimadzu HPLC system equipped with a refractive index detector RID-10A and two Polymer Laboratories PLgel 5 µm mixed D columns (with guard column). Lithium bromide (0.1 M) in N,N-dimethylformamide (DMF) at 40° C. was used as the solvent (flow rate: 0.6 mL/min). Near-monodisperse poly(methyl methacrylate) standards (Polymer Laboratories) were employed for calibration. Infrared spectra were obtained with a Perkin-Elmer Spectrum One instrument equipped with a universal ATR accessory. Preparatory reverse phase HPLC was carried out on a Shimadzu HPLC system equipped with a UV detector using a Luna 5 µm C18 100A column (preparatory: 5 µm, 250×21.2 mm) with monitoring at λ=215 nm and 254 nm. Isocratic solvent system (water:methanol=50:50) was used as the mobile phase at a flow rate of 10 mL/min. Fluorescence measurement was made on a FlexStation II (Molecular Devices). UV-Vis absorbance was measured using a microplate reader ELx800 (BioTek Instruments, Winooski, Vt.).

Methods

Synthesis of the Trehalose Polymer.

AIBN (5.28 mg, 3.22×10−2 mmol) and styrenyl ether trehalose monomer (634 mg, 1.38 mmol) were dissolved in a mixture of DMF (2.31 mL) and H2O (4.61 mL). Oxygen was removed by three cycles of freeze-pump-thaw and polymerization was initiated at 75° C. The polymerization was stopped after 8.5 h by immersing the reaction into liquid nitrogen. The polymer was purified by dialysis against H2O (MWCO 3,500) resulting in a polymer with Mn=7.0 kDa and Ð=1.28 (for hydrogel dissolution experiment) and Mn=7.6 kDa and Ð=1.33 (for all other experiments). 1H NMR (500 MHz in D2O) δ: 7.01, 6.45, 5.05, 3.81, 3.71, 3.59, 3.48, 3.36, 1.50.

Synthesis of Poly(Styrenyl Ether Trehalose) (Poly(SET)).

AIBN (5.28 mg, 3.22×10$^{-2}$ mmol) and SET (634 mg, 1.38 mmol) were dissolved in a mixture of DMF (2.31 mL) and H$_2$O (4.61 mL). Oxygen was removed by three cycles of freeze-pump-thaw and polymerization was initiated at 75° C. The polymerization was stopped after 8.5 h by immersing the reaction into liquid nitrogen. The polymer was purified by dialysis against H$_2$O (MWCO 3,500) resulting in a polymer with $M_n$ of 7.0 kDa and PDI of 1.28. $^1$H NMR (500 MHz in D$_2$O) δ: 7.01, 6.45, 5.05, 3.81, 3.71, 3.59, 3.48, 3.36, 1.50.

Synthesis of 8-Arm PEG Boronic Acid.

8-arm-PEG amine (400 mg, 10 kDa, 4×10$^2$ mmol) and 4-formyl boronic acid (96 mg, 6.40×10$^{-1}$ mmol) were dissolved in 2.8 mL of MeOH. NaBH$_3$CN (18.85 mg, 3.00× 10$^{-1}$ mmol) was added and the reaction was stirred at 25° C. After 5 days the reaction solution was purified by dialysis against MeOH for 2 days and H$_2$O for 2 days. The sample was lyophilized and $^1$H-NMR analysis showed 100% modification of amine end-groups in the PEG. $^1$H NMR (500 MHz in D$_2$O) δ: 7.75 (16H), 7.41 (16H), 4.14, 3.69, 3.18 (908H). IR: δ=3390, 2869, 1699, 1456, 1410, 1348, 1297, 1247, 1079, 1041, 986, 947, 839 cm$^{-1}$.

Synthesis of Poly(SET)-Boronic Acid Hydrogel.

Poly(SET) and 8 arm PEG boronic acid (10 kDa) were dissolved in pH 7.4 D-PBS buffer to concentrations of 500 mg/mL and 200 mg/mL respectively. 3 µL of poly(SET) solution and 20.5 µL of 8arm PEG amine solution were mixed (1:1=trehalose unit:boronic acid unit) to result in the hydrogel.

Glucose-Responsiveness Study. Fifteen separately prepared poly(SET)-boronic acid hydrogels were immersed into 150 µL of pH 7.4 D-PBS buffer for 1 h. The hydrogels were air-dried for 15 min and their weights were measured. Each of the hydrogels were then immersed into 150 µL of either pH 7.4 D-PBS buffer, 1 mg/mL, 5 mg/mL, 10 mg/mL, or 20 mg/mL glucose solution in pH 7.4 D-PBS buffer (three hydrogels per condition). Each time point was collected by air-drying hydrogels for 15 min and weighing the dried hydrogels.

Hydrogel Dissolution Kinetics.

The trehalose polymer (500 mg/mL) and the PEG cross-linker (200 mg/mL) stock solutions were prepared in D-PBS, pH 7.4. The gels were prepared by adding 3 µL of the trehalose polymer stock solution and 20.5 µL of the PEG cross-linker stock solution and incubating at room temperature for 30 min. The gels were hydrated in D-PBS for 1 h, and then transferred to 5 mL D-PBS containing 0, 1, 5, 10, or 20 mg/mL glucose. At each time point, gels were weighed and then replaced into respective buffers.

FITC Labeling of Insulin.

Insulin was labeled with fluorescein isothiocyanate isomer I (FITC) by dissolving insulin (0.65 mg, 0.112 µmol) and FITC (3.48 mg, 8.94 µmol) in 0.33 mL of 1 M sodium bicarbonate buffer, pH 8.3. The mixture was stirred for two hours, and free FITC was removed by repeated centrifugation through a membrane using Centriprep™ tubes with molecular weight cut-off (MWCO) of 3,000 Da. Typical degree of labeling was approximately 0.7 FITC per insulin as determined by UV absorbance (Schreiber and Haimovich, 1983).

Preparation of Boronic Acid Crosslinker and Trehalose Hydrogels

The boronic acid crosslinker was synthesized through reductive amination, using 4-formyl boronic acid and 8arm PEG amine as starting materials (Scheme 1). Complete modification of 8arm PEG amines with phenylboronic acid was confirmed by $^1$H NMR spectroscopy (FIG. 1).

The synthesized 8arm PEG boronic acid was then mixed with poly(SET) in a ratio of boronic acid to trehalose unit 1:1 (Scheme 2). The gelation occurred rapidly within 3 min (FIG. 2).

FITC-Labeled Insulin Release from Trehalose Hydrogel.

FITC-labeled insulin (13.22 mg/mL in Dulbecco's phosphate-buffered saline (D-PBS, pH 7.4 or pH 8) was added to the trehalose polymer to make a polymer concentration of 500 mg/mL. The PEG cross-linker was dissolved in D-PBS at 200 mg/mL concentration. Next, 1 µL of the trehalose polymer and FITC-labeled insulin stock solution and 6.84 µL of the PEG cross-linker stock solution were added to an Eppendorf Lo-Bind® centrifuge tube. The tube was agitated on a ThermoShaker (Allsheng Instruments, China) at 1,500 rpm at 21° C. for 1 h. The gels were transferred into a 24-well plate filled with 1 mL D-PBS and left to hydrate for 30 min. Next, the gels were transferred to a 96-well plate that had been blocked with 1% wt/vol bovine serum albumin (BSA) in D-PBS to prevent protein adsorption and filled with 0.3 mL of D-PBS containing 0, 5, or 10 mg/mL glucose. At each time point, all the solution was aliquoted and the wells containing the gels were immediately refilled with 0.3 mL of the same buffer. After the last time point, the wells were treated with 0.3 mL of D-PBS containing 100 mg/mL glucose and incubated at 37° C. for 5 min to completely dissolve the gels. All the solution was then transferred for measurement, and fluorescence of the time point aliquots and the residual insulin solutions recovered after gel dissolution was measured.

Trehalose Hydrogel Heating Assay.

Stock insulin solution was prepared by first dissolving insulin in D-PBS, pH 7.4 at 1 mg/mL concentration, and then concentrated by centrifugation through a membrane using Centriprep™ tubes with molecular weight cut-off (MWCO) of 3000 Da. The protein concentration was quantified by UV absorbance at 280 nm, and the solution was diluted to 3.93 mg/mL such that the final insulin concentration in the samples was 0.5 mg/mL. Trehalose polymer stock solution was prepared by dissolving the trehalose polymer in the insulin stock solution at a 500 mg/mL concentration. The PEG cross-linker was dissolved in D-PBS at 200 mg/mL concentration. The gels were prepared by adding 1 µL of insulin or trehalose polymer stock solution and 6.84 µL of PEG cross-linker stock solution or D-PBS to an Eppendorf Lo-Bind® centrifuge tube, and agitating the tube on a ThermoShaker at 1,500 rpm at 21° C. for 1 h to aid in mixing. The samples were heated at 90° C. for 30 min and the controls were kept at 4° C. All samples were treated with 1 mL of 100 mg/mL glucose in order to dissolve the hydrogel. The amount of insulin was assayed by ELISA, which was conducted according to manufacturer's instructions. Briefly, 25 µL of the diluted samples were added to the wells pre-coated with the capture antibody. Buffer containing detection antibody was added (100 µL), and the plate was incubated on a rocker at room temperature for 1 h. To prevent residual boronic acid binding to the sugar moieties on horseradish peroxidase used for ELISA, 3-4 the wells were washed with 350 µL of deionized water acidified with HCl (pH=3.5) five times after the incubation, and then six times with 350 µL of the wash buffer. These additional washing steps do not affect the ELISA results as confirmed by the controls. 3,3',5,5'-Tetramethylbenzidine (TMB) solution was added (200 µL), and the plate was incubated at room temperature for 15 min before the addition of 50 µL stop solution. The amount of insulin detected was quantified by absorbance at 450 nm relative to the standards supplied by the manufacturer.

Statistical Analysis.

One-tailed Student's t-test assuming unequal sample variance was used to test the difference between experimental groups. Results were considered significantly different if $p<0.05$.

Glucose-Responsiveness Study of the Poly(SET)-Boronic Acid Hydrogel

The prepared poly(SET)-boronic acid hydrogel was then tested for glucose-responsiveness. Since the boronic ester bond from the trehalose-boronic acid complex is expected to have a significantly weaker binding affinity than that of glucose-boronic acid (Nagai et al., 1993; Vandenberg et al., 1994), glucose should replace the boronic ester bond between the trehalose polymer and the boronic acid cross-linker. This would de-crosslink the polymer chains and the boronic acid crosslinker reversing the hydrogel. As the polymer and the crosslinker are all water soluble and can therefore diffuse into the buffer, the hydrogel should loose weight during this process. As shown in FIG. 3, the hydrogel lost 34% of its original weight after immersing the gel into pH 7.4 D-PBS buffer. This may due to the diffusion of uncrosslinked polymer or crosslinker from the hydrogel. However, when the hydrogels were placed into the buffer with glucose, their weight loss was clearly faster. There was a clear trend that higher concentration glucose solutions de-crosslinked the hydrogel more rapidly. The weights of the hydrogels immersed in 10 mg/mL and 20 mg/mL glucose solutions were unable to be measured after 10 minutes because they had dissolved into the solution, whereas hydrogels in 1 mg/mL and 5 mg/mL glucose solutions were still gels at 10 minutes.

Discussion.

To date, hydrogels using trehalose and boronic acid binding have not yet been reported. The above data suggest that hydrogels can be prepared by utilizing a boronic ester bond between our previously reported trehalose polymers and a phenylboronic acid functionalized multi-arm PEG. The gelation was fast in physiological conditions (pH 7.4). Moreover, the resulting hydrogel was glucose-responsive. The addition of glucose led to de-crosslinking of the boronic ester bond between trehalose (polymer) and boronic acid (crosslinker) by competitive replacement of glucose-boronic acid complex due to the higher binding affinity of glucose to phenylboronic acid. As expected, higher glucose concentration buffers increased the rate of dissolution of the hydrogel. This suggests that these gels could be utilized for insulin delivery applications. Indeed, future work will involve studies of stabilization and release of insulin from these gels.

Conclusion.

Herein, we have described the preparation of a hydrogel using a trehalose side chain polymer and 8arm boronic acid-functionalized PEG. In 1:1 ratio of trehalose unit to boronic acid unit, the hydrogel was formed within 3 min. By measuring the weight loss of the hydrogels after incubation in various conditions, deformation of the hydrogel was observed as expected. The higher the concentration of glucose, the faster the hydrogel dissolved. We expect that this trehalose-based hydrogel can be used for effective in vivo glucose-responsive insulin delivery, with the advantage of using trehalose polymer as an insulin stabilizer during storage before use.

Glucose-Responsive Trehalose Hydrogel for Insulin Stabilization and Delivery

Our group has previously shown that trehalose glycopolymers are effective stabilizers for proteins against lyophilization and heat either as conjugates or as excipients (Lee et al., 2013; Mancini et al., 2012). We hypothesized that the trehalose glycopolymer, named PolyProtek™, could be used to entrap insulin by complexing with a boronic acid cross-linker and that the resulting hydrogel would also stabilize insulin against environmental stressors. To test this hypothesis, a boronic acid cross-linker was synthesized through reductive amination, using 4-formylphenylboronic acid and 8-arm PEG amine as starting materials (Scheme 1). Complete modification of the amine end-groups with phenylboronic acid was confirmed by $^1$H NMR spectroscopy (FIG. 1; bottom). Next, the trehalose hydrogel was prepared by mixing the 8-arm PEG boronic acid with poly(styrenyl ether trehalose) (PolySET) at 1:1 molar ratio of boronic acid to trehalose units (Scheme 2) in Dulbecco phosphate buffered saline (D-PBS). The gelation occurred instantaneously after mixing the solutions of the two components (FIG. 2 for images of the hydrogels).

The prepared PolySET boronic ester hydrogel was then tested for glucose responsiveness. There are some reports that trehalose does not complex with boronic acids (Nagai et al., 1993; Stones et al., 2004). However, trehalose-boronic acid binding has been observed for multivalent boronic acid-DNA conjugates (Hargrove et al., 2011), and the association constant of boric acid with trehalose was measured to be smaller than glucose (Van den Berg et al., 1994). Although the weak association of trehalose with boronic acid has generally limited its usefulness in sugar sensing applications (James et al., 1996), we envisioned that the weak affinity may be used advantageously for rapid displacement of trehalose polymer by glucose to dissolve the hydrogel and release insulin. To test this, the kinetics of hydrogel dissolution were monitored by measuring hydrogel weight upon addition of glucose.

As shown in FIG. 3, when the hydrogels were placed into the buffer containing glucose, the rate of percent weight loss was significantly faster with increasing glucose concentration. The weights of the hydrogels immersed in 10 and 20 mg/mL glucose solutions were unable to be measured after 10 minutes because the hydrogels had completely dissolved and were undetectable in the solution, while hydrogels in 1 mg/mL and 5 mg/mL glucose solutions were still intact after 60 min. Approximately 34% weight loss was observed after immersing the gel in D-PBS without any glucose for 60 minutes. Since the boronate ester bond is in dynamic equilibrium and the bond to trehalose is weak (Van den Berg et al., 1994), the trehalose polymer may slowly diffuse out from the hydrogel surface even in the absence of glucose. Yet with addition of glucose, the weight loss was remarkably accelerated, demonstrating the glucose-responsiveness of the gels.

Figure 6:
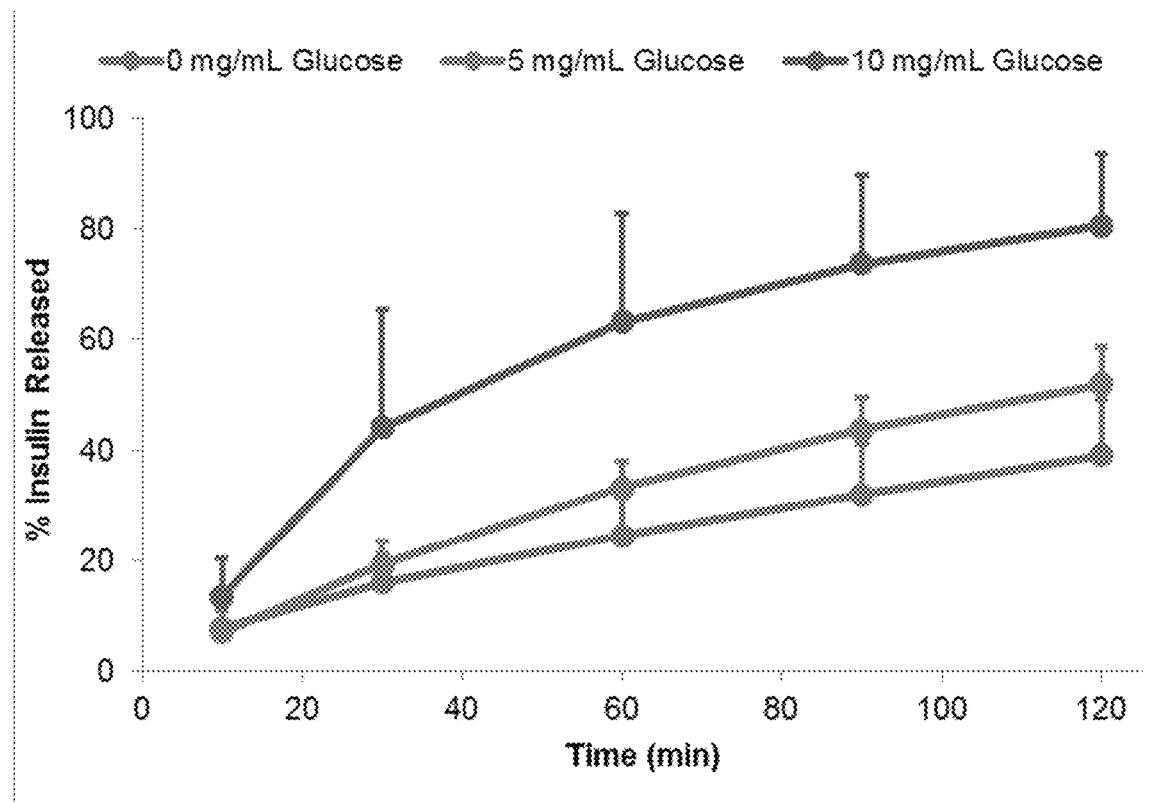
FIG. 6 is a graph showing insulin released in D-PBS, pH 8.0, containing 0, 5, and 10 mg/mL glucose (n=3 per group).
Figure 7:
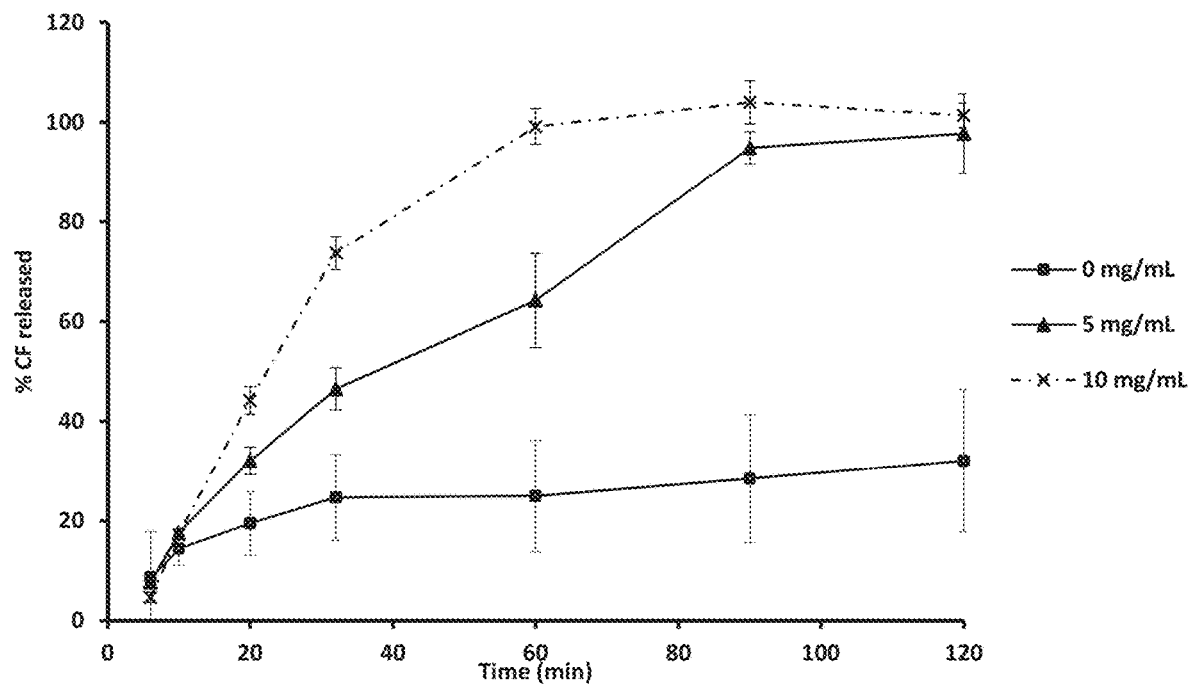
FIG. 7 is a graph showing kinetic studies of trehalose hydrogel releasing fluorophore of carboxyfluorescein release in D-PBS buffer, pH 7.4 (n=3) upon addition of glucose.

To test insulin release upon addition of glucose, the PolySET boronic acid hydrogels were prepared in the presence of FITC-labeled insulin (FIG. 2b). 8-arm PEG boronic acid was dissolved in a buffer containing FITC-labeled insulin and mixed with the PolySET to prepare insulin, and these hydrogels were added into D-PBS containing 0, 5, and 10 mg/mL glucose at a physiological pH (pH 7.4). Aliquots were taken from the solutions at each time point and insulin released was quantified (FIG. 4). As with the gel dissolution experiment, in the presence of glucose the hydrogel released insulin more rapidly. After one hour, the hydrogel in 10 mg/mL glucose solution was completely dissolved to yield 100% insulin release, while over the same time period 80% and 49% insulin were released in 5 mg/mL and 0 mg/mL glucose solution, respectively. Also, insulin release in basic buffer (pH 8.0) was slower for all conditions (FIG. 6), suggesting that pKa of boronic acid may be tailored as desired for more rapid or delayed insulin delivery. This has been exploited in other system (Matsumoto et al., 2012; Roy et al., 2009).

Next, we tested the ability of the trehalose hydrogel to stabilize insulin against heating. Insulin solutions were separately prepared without any additive, with PolySET, with 8-arm PEG boronic acid, and with the trehalose hydrogel. The samples were heated for 30 min at 90° C. to accelerate degradation and then tested with insulin ELISA to confirm the structural integrity of insulin. A control group with insulin and the trehalose hydrogel stored at 4° C. demonstrated that the hydrogel did not affect the ELISA results (FIG. 5).

The data shows that the glucose-responsive trehalose hydrogel is effective at stabilizing insulin against heating stress (FIG. 5). Insulin without any additive underwent degradation and no longer bound to the antibody upon heating and showed less than 2% signal by ELISA. Significantly more insulin was detected in the presence of additives. PolySET remarkably stabilized insulin and 63% of the original protein was detected after heating to 90° C. for 30 min. Insulin was also partially stabilized in the presence of the 8-arm PEG boronic acid alone (39% signal). The literature is divided on the effect of PEG on protein stability; it has been suggested that PEG may accelerate protein denaturation at higher temperatures due to the interaction of hydrophobic PEG with the denatured state of protein (Lee and Lee, 1987; Senske et al., 2014). However, the specific architecture of PEG polymer may dictate whether PEG stabilizes or destabilizes proteins. For example, Amirgoulova et al. have reported that linear PEG interacts with the denatured state of a protein to favor unfolding, and used star-shaped PEG instead for their surface coating applications (Amirgoulova et al., 2004). The combination of both poly(SET) and branched PEG as a hydrogel resulted in 74% stabilization, significantly better than the 8-arm PEG boronic acid (p<0.01) and similar to poly(SET) alone. These results suggest that even though the poly(SET) is partially bound to the 8-arm PEG boronic acid in the gel, the stabilizing properties are maintained.

In summary, we have synthesized a glucose-responsive hydrogel based on a trehalose glycopolymer for insulin delivery. The results demonstrate that hydrogels can be readily prepared from trehalose polymers and boronic acid cross linkers. The gelation occurred under physiological conditions pH, and the resulting hydrogel was capable of releasing insulin in a glucose-responsive manner. The addition of glucose led to breaking of the boronate ester bond between the trehalose polymer and the boronic acid crosslinker through competitive displacement by glucose, which has a higher binding affinity to boronic acid (Van den Berg et al., 1994). As expected, higher glucose concentration in the buffer increased the rate of dissolution of the hydrogel and resulted in faster release of loaded insulin. Additionally, the trehalose hydrogel can effectively protect insulin against extreme heat stress. Since most of the protein drugs must be stored under regulated temperature to maintain their activities, trehalose hydrogels in general may be used to enhance the quality of life of patients by not requiring specialized refrigeration. In addition, as boronic acid has been used to create pH-responsive materials (Roy et al., 2009), the trehalose boronic-acid hydrogels may have potential applications as anti-cancer drug delivery agent to release the drug at acidic extracellular pH near tumors (Lee et al., 2008).

Example 2 pH Responsive Trehalose Hydrogels

Applicants propose a unique pH responsive hydrogel based on trehalose. To our knowledge no pH responsive hydrogel based on trehalose have been reported. The trehalose is generally regarded as safe by US Federal Drug Administration (FDA) and act as a natural stabilizer for cells and proteins in organisms, which makes it to be a perfect candidate for synthesis of hydrogel for biomedical use (Teramoto et al., 2008). We have already reported that trehalose side chain glypolymers help maintaining protein activity against heat and lyophilization (Mancini et al., 2012; Lee et al., 2013). Therefore, we expect trehalose hydrogels to act not only as a delivery vehicle but also as stabilizers against environmental stressors during storage and transportation. For hydrogel synthesis, a crosslinker was synthesized by bis-functionalizing trehalose with a polymerizable styrenyl group with an acid cleavable acetal linkage. Trehalose-based hydrogels were prepared using both free radical and redox polymerization. The solubility of the hydrogel was tested in different pH aqueous solutions. The hydrogel remained gelled in solutions greater than pH 5 and dissolved in 10% TFA.

Materials

All the chemicals were purchased from Sigma-Aldrich and Fisher Scientific and were used without purification unless noted otherwise. Trehalose was purchased from The Healthy Essential Management Corporation (Houston, Tex.), dried with ethanol and kept under vacuum before use. Azobisisobutyronitrile (AIBN) was recrystallized from acetone before use. 4-vinylbenzaldehyde diethyl acetal, styrenyl acetal trehalose monomer (SAT), styrenyl ether trehalose monomer (SET), and poly(SAT) were prepared using the previously reported procedures as discussed above (Mancini et al., 2012; Lee et al., 2013).

Analytical Techniques

NMR spectra were obtained on Bruker AV 500 and DRX 500 MHz spectrometers. $^1$H NMR spectra were acquired with a relaxation delay of 2 s for small molecules and 30 s for polymers. Infrared absorption spectra were recorded using a PerkinElmer FT-IR equipped with an ATR accessory. ESI-MS data were gathered on a Waters LCT premier with ACQUITY LC.

Synthesis of Bis-Styrenyl Acetal Trehalose Crosslinker (Bis-SAT).

To the flame-dried reaction flask, trehalose (398 mg, 1.16 mmol) and DMF (4 mL) were added. p-TsOH (7.08 mg, $3.72 \times 10^{-2}$ mmol) was added and the reaction was stirred for 10 min immersed in a 100° C. oil bath. To the reaction 4-vinylbenzaldehyde diethyl acetal (600 mg, 2.91 mmol) was slowly added and the reaction was stirred at 100° C. for 2 h. After the reaction was complete, 80% of DMF was removed in vacuo and the remaining solution precipitated in benzene. The precipitate was filtered with saturated NaHCO$_3$ and washed with H$_2$O extensively. The filter cake was collected and recrystallized in EtOH:H$_2$O=2:1 resulting in 478.5 mg white powder with 72% yield. $^1$H NMR (500 MHz in D$_6$DMSO) δ: 7.48-7.44 (m, 8H), 6.80-6.74 (m, 2H), 5.84-5.81 (d, J=18.15 Hz, 2H), 5.56 (s, 2H), 5.29-5.27 (d, J=10.37 Hz, 2H), 5.10-5.09 (m, 2H), 4.19-4.16 (m, 2H), 4.00-3.97 (m, 2H), 3.93-3.89 (m, 2H), 3.72-3.68 (t, J=10.81 Hz, 2H), 3.58-3.53 (m, 2H), 3.47-3.44 (m, 4H), 3.32-3.30 (m, 2H). ESI-MS (±1.0) observed (predicted): H$^+$ 571.22 (571.22).

Preparation of SAT Hydrogel Through Free Radical Polymerization.

SAT (200 mg, $4.38 \times 10^{-1}$ mmol), bis-SAT (13.16 mg, $2.31 \times 10^{-2}$ mmol), and AIBN (0.72 mg, $4.38 \times 10^{-3}$ mmol) were dissolved into 1 mL of DMF. Oxygen was removed by three freeze-pump-thaw cycles and polymerization was initiated by immersing the reaction flask into a 90° C. oil bath. Within 30 min the gel began to form and the reaction was stopped after 6 h by immersing the reaction flask into liquid nitrogen. The gel was washed with H$_2$O and MeOH to remove unreacted monomer and crosslinker.

Preparation of SAT Hydrogel Through Redox Polymerization.

SAT (20 mg, $4.38 \times 10^{-2}$ mmol) and bis-SAT (0.5 mg, $8.76 \times 10^{-4}$ mmol) were separately dissolved in H$_2$O (150 μL) and DMF (50 μL), respectively. To the solution, TEMED ($2.25 \times 10^{-1}$ μL, $1.5 \times 10^{-3}$ mmol) and APS (50 μL in $2.28 \times 10^{-3}$ mg/mL, $5.00 \times 10^{-4}$ mmol) were added to start the gelation. A hydrogel was formed in 2 hours, and the resulting gel was purified by washing with H$_2$O and MeOH.

Preparation of SET Hydrogel Through Free Radical Polymerization.

SET (40.49 mg, $8.82 \times 10^{-2}$ mmol), bis-SAT (5 mg, $8.76 \times 10^{-3}$ mmol) and AIBN (0.29 mg, $1.77 \times 10^{-3}$ mmol) were dissolved in 0.11 mL DMF and 0.22 mL of H$_2$O. After three cycles of freeze-pump-thaw, the gelation was started at 80° C. and stopped after 4 h by cooling with liquid nitrogen. The resulting gel was washed with H$_2$O and MeOH to purify.

Hydrolysis Study of Poly(SAT).

50 mg of poly(SAT) (33,700 g/mol, $1.48 \times 10^{-3}$ mmol) was dissolved in pH 3, pH 4, pH 5, and 10% TFA aqueous solution. The reaction was stirred at 25° C. and dialyzed against H$_2$O (MWCO 3,500 g/mol) for three days and lyophilized.

Hydrolysis Study of SET Hydrogel.

To the three SET hydrogels (0.3 mg each) 500 μL of pH 7.4 D-PBS, pH 5 PBS, and 10% TFA solution was added. The solubility of each sample was monitored through the time.

Preparation of Trehalose Crosslinker and Trehalose Hydrogels

Figure 8:
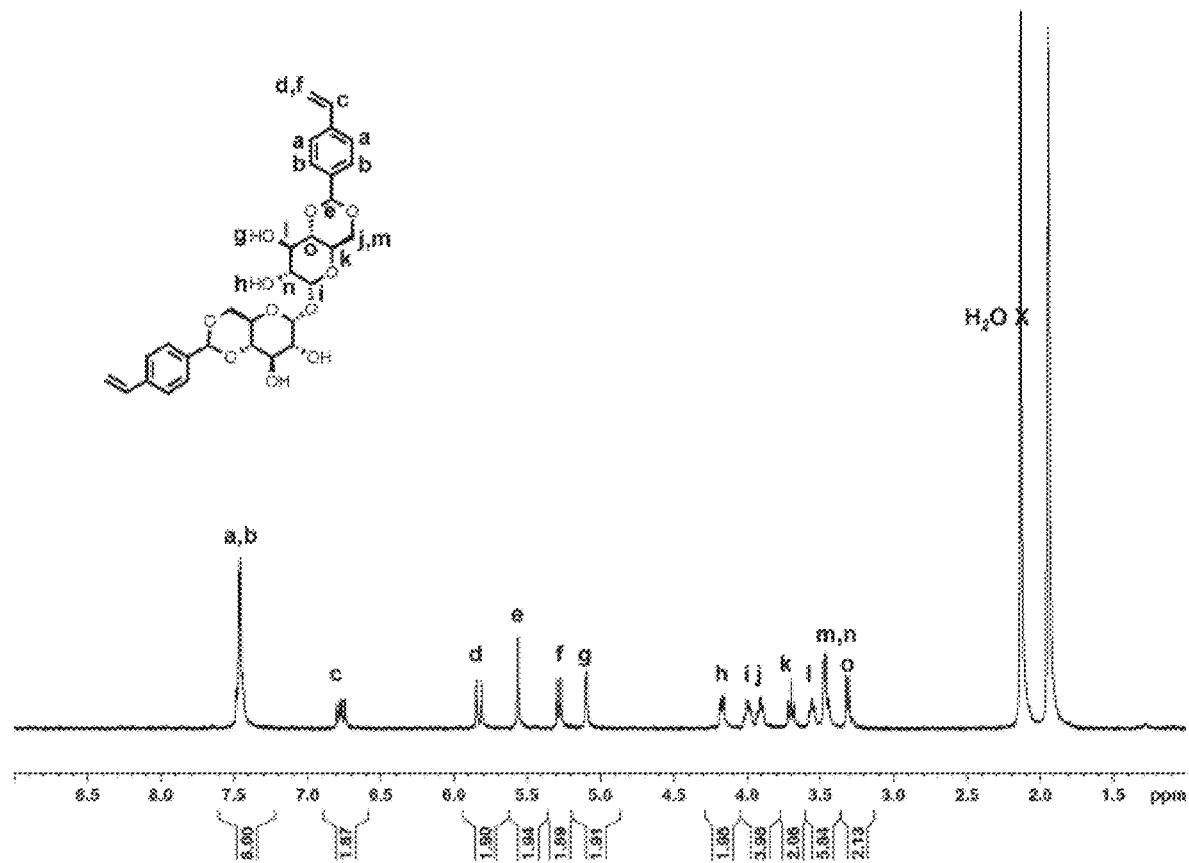
FIG. 8 is a graph showing $^1$H NMR spectroscopy of bis-SAT Crosslinker (in $CD_3CN$).

To synthesize a trehalose crosslinker, we used the method previously reported for the synthesis of trehalose monomer (Mancini et al., 2012). To increase the yield for the bis-functionalized crosslinker over the monomer, 2.2 molar equiv of 4-vinylbenzaldehyde diethyl acetal was added to the trehalose (Scheme 3). The bis-SAT crosslinker was prepared through transacetalization (FIG. 8) in 72% yield.

This bis-SAT crosslinker was copolymerized to form both SAT and SET hydrogels through heat initiated free radical polymerization and redox polymerization (Scheme 4 and Scheme 5). For the SAT hydrogel, both synthetic routes resulted in hydrogels. During the AIBN-mediated free radical polymerization, the hydrogel formation was observed within 30 min at 90° C., whereas redox polymerization required 2 h to gel at 25° C. In contrast, the SET hydrogel could only be obtained through free radical polymerization. During the free radical crosslinking in H$_2$O/DMF (=2/1) co-solvent, the SET monomer was observed to precipitate out of the solution. All hydrogels were purified by washing with H$_2$O and MeOH to remove unreacted starting materials or uncrosslinked polymer chains.

To study acetal cleavage in the hydrogels, linear poly (SAT) was used as a model system. Poly(SAT) was dissolved in a series of acidic pHs to induce hydrolysis of the acetal linkage between trehalose and the pendant moiety in the polymer backbone. The resulting aldehyde was observed by $^1$H NMR spectroscopy. In pH 3-5, all the trehalose peaks remained constant and no aldehyde peak was observed (data not shown). However, when the polymer was treated with 10% TFA, the $^1$H NMR peaks corresponding to the trehalose protons (FIG. 9; top, 3.0-5.5 ppm) disappeared and an aldehyde peak became visible. The $^1$H NMR spectrum of the resulting polymer appeared identical to the trace expected for a 4-benzaldehyde polymer (FIG. 9; bottom).

Next, the SET hydrogel-1, where the polymer contains stable ether linkages and only the cross-linker has a reversible bond was treated with D-PBS, pH 7.4, PBS, pH 5, and 10% TFA aqueous solution. Because of the crosslinking, the hydrogel would not dissolve in aqueous buffer. Yet similar to the poly(SAT) hydrolysis study, the SET hydrogel-1 in 10% TFA dissolved completely within 3 min. The gel remained at both pH 7.4 and pH 5 even after 48 h incubation at 25° C. suggesting a low pH is required to reverse the acetal crosslinker linkage (FIG. 10).

Discussion

Together, the above data describe the development of acid-responsive trehalose-based hydrogels. First, a trehalose crosslinker was synthesized using identical chemistry as was used to prepare the SAT monomer. This resulted in a hydrogel containing trehalose moieties in the crosslinker as well as the backbone, which may increase the stabilization effect for encapsulated therapeutic proteins. Although SAT could form a hydrogel with bis-SAT using both free radical polymerization and redox chemistry, SET was not able to form a hydrogel with the same crosslinker. This is likely due to the differential solubility of SET and bis-SAT in 25° C., H$_2$O and DMF respectively. A higher temperature is required to solubilize the monomer and cross-linker. A noticeable observation was that the acetal bond of bis-SAT (or SAT) could not be hydrolyzed even in pH 3. Only when 10% TFA was added was the acetal bond hydrolyzed to the aldehyde. This acid-stability was unexpected, since acetal bonds had previously been used as pH responsive crosslinkers in hydrogels (Bachelder et al., 2008; Li et al., 2006; Murthy et al., 2002; Chen et al., 2010). The surprising acid stability could be due to the polymer backbone, which is in the para position of the benzaldehyde acetal. The substituent in the para position is known to be important in influencing the acid lability of the acetal bond (Murthy et al., 2002; Fife and Jao, 1965). In addition, the hydrophobic backbone may prevent water from reaching the acetal bond thereby preventing hydrolysis. When a 10% TFA solution was added to linear poly(SAT), all the side chains were hydrolyzed releasing the trehalose; only the polybenzaldehyde backbone was left after purification. However, there were no difference in $^1$H NMR specta when the pH 3 to pH 5 aqueous solution was added. Also, when the SET hydrogel-1 was treated with a 10% TFA solution, the gel solubilized suggesting that the bis-SAT hydrolyzed.

Conclusion

In this chapter, we have described the synthesis of various trehalose hydrogels using a bis-styrenyl acetal functionalized trehalose crosslinker. Two different trehalose monomers formed gels with this crosslinker through AIBN-mediated free radical polymerization. Hydrolysis of the acetal linkage was not detected until it added into a 10% TFA solution. We expect these acid cleavable trehalose hydrogels could be used as vehicles for delivery of protein or peptide therapeutics to the stomach or stabilizers for enzymes used in acid triggered chemical synthesis and water purification.

Example 3

Trehalose Hydrogels for Stabilization of Enzymes

Introduction

The application relates to a hydrogel system based on the natural disaccharide trehalose as an efficient excipient to enhance the thermostability of proteins. This trehalose hydrogel can be prepared in only two steps from trehalose using simple purification steps, which can be directly applied industrially for stabilization of proteins.

Applicants chose to study stabilization of phytase because of its importance in the animal feed industry. Phytase is a phosphohydrolytic enzyme that catalyzes the conversion of phosphate in indigestible phytic acid to a highly digestible form (Lei et al., 2013; Kuhn and Partanen, 2012; Nahm, 2002; Silversides, et al., 2004). The conversion of phytic acid is essential for simple-stomached species such as swine, poultry, and fish to utilize this storage form of phosphate present in common feed grains such as corn, soy, and wheat (Lei et al., 2013). In 2011, phytase accounted for approximately 60% of the $550 million global feed enzyme market (Adeola and Cowieson, 2011). Yet, the biggest challenge in the use of phytase in animal feeds is its low thermostability during steam heating of the pelleting process, during which the temperature between 70-90° C. is reached (Lei et al., 2013; Slominski et al., 2007). Despite previous efforts to enhance its heat stability (Lei et al., 2013; Slominski et al., 2007; Hughes and Soares, 1998; Cao et al., 2007), a simple and cost-effective method is still of great interest. As described below, Applicants found that phytase retains 100% activity when heated to 90° C. in the presence of trehalose hydrogels.

Materials

All the chemicals were purchased from Sigma-Aldrich, Thermo Scientific, and Fisher Scientific and were used without purification unless noted otherwise. Trehalose was purchased from The Endowment for Medical Research (Houston, Tex.) and dried with ethanol and kept under vacuum before use. Alexa Fluor® 488 microscale protein labeling kit (A30006) was purchase from life technologies. All solvents for liquid chromatography mass spectrometry (LCMS) were purchased from VWR or Fisher Scientific in LCMS grade. Trehalose was purchased from The Healthy Essential Management Corporation (Houston, Tex.), and was azeotropically dried with ethanol and kept under vacuum until use. Phytase was provided by Phytex, LLC.

Analytical Techniques

UV-Vis spectra were obtained using a Thermo Scientific Nanodrop 2000 Spectrophotometer. Confocal microscopy images were obtained from a Leical SP2 1P-FCS confocal microscope with axial resolution of 25 μm. LCMS experiments were carried out on a Waters Acquity UPLC connected to a Waters LCT-Premier XE Time of Flight Instrument controlled by MassLynx 4.1 software. The mass spectrometer was equipped with a Multi-Mode Source operated in the electrospray mode. Trehalose samples were separated using an Acquity BEH C18 1.7 um column (2.1×50 mm) and were eluted with a gradient of 5-50% solvent B over 6 min (solvent A: water, solvent B: acetonitrile, both with 0.2% formic acid (vol/vol)). Mass spectra were recorded in the negative ion mode in the m/z range of 70-2000 with leucine enkephalin (Sigma L9133) as the lock mass standard. Preparatory reverse phase HPLC was carried out on a Shimadzu HPLC system equipped with a UV detector using a Luna 5 m C18 100A column (preparatory: 5 μm, 250×21.2 mm) with monitoring at λ=215 nm and 254 nm. A linear gradient solvent system ($H_2O$: methanol=70:30 to 50:50) was used as the mobile phase at a flow rate of 10 mL/min. Scanning electron microscopy (SEM) images were acquired on a FEI Nova Nano 230 SEM in the UCLA Molecular and Nano Archaeology (MNA) facility under a low vacuum of 50 Pa and high voltage of 5 or 2.5 kV with a spot size of 3.0. Fluorescence images of the hydrogels were acquired using a confocal laser scanning microscope (Leica SP2 1P-FCS, Leica) at the CNSI Advanced Light Microscopy/Spectroscopy Shared Resource Facility at UCLA. Diameter of phytase (PDB: 1DKL) (Lim et al., 2000) was measured using Swiss-PdbViewer (Swiss Institute of Bioinformatics) (Guex and Peitsch, 1997). Fluorescence measurements were made on a FlexStation II (Molecular Devices). Light absorbance for phytase activity assay was measured using a Biotek EPOCH microtiter plate reader.

One Pot Reaction for Synthesis of Trehalose Monomers and Cross-Linkers (Crude SET).

The one pot reaction for the monomers and cross-linkers was performed by modifying a previously reported literature procedure (Teramoto and Shibata, 2004). Sodium hydroxide (NaOH, 4.44 g, $1.11 \times 10^{-1}$ mol) was added to dimethyl sulfoxide (DMSO, 96 mL). After stirring for 5 min, trehalose (4.86 g, $1.42 \times 10^{-2}$ mol) was added to the reaction. After all the trehalose was dissolved, 4-vinylbenzyl chloride (0.4 mL, $2.84 \times 10^{-3}$ mol) was slowly added to the reaction and was stirred for 24 h at 25° C. The crude product was then precipitated into 2 L of DCM to remove highly modified trehalose. The resulting solid was dried in vacuo and used for gelation without further purification.

Preparation of Phytase-Loaded Trehalose Hydrogel.

The crude mixture (3.23 g) from the previous Williamson etherification was dissolved in $H_2O$ (3.23 mL) and then treated with tetramethylethylenediamine (TEMED, 16 µL, $1.07 \times 10^{-4}$ mol). Next, 807 µL of 10 mg/mL aqueous stock solution of ammonium persulfate (APS, 8.07 mg, $3.54 \times 10^{-5}$ mol) was added to initiate the gelation. The solution started gelling within 10 min at 25° C. LCMS was used to quantify the extent of conversion, by comparing the relative amount of mono-substituted trehalose compared to unmodified trehalose before and after gelation. LCMS analysis showed that all cross-linkers had reacted after 24 h. After the gelation, the gel was washed with a Soxhlet extractor for 3 days with $H_2O$ to remove unreacted monomers. The hydrogel was lyophilized and then grinded into fine powder. 10 µL of phytase solutions of different concentrations were added to each dried gel to make phytase:hydrogel ratios of 1:1, 1:10, and 1:40 weight equivalents. The gels were incubated at 4° C. with the phytase solution for 24 h and lyophilized to yield a white powder for testing in the heat burden study.

Fluorescein Isothiocyanate (FITC) Labeling of Phytase.

Phytase (2 mg, $3.57 \times 10^{-2}$ µmol) and FITC (0.3 mg, $7.71 \times 10^{-1}$ µmol) were dissolved in 50 mM borate buffer, pH 8.5 (1 mL). The mixture was magnetically stirred at room temperature for an hour. Excess FITC was removed by repeated centrifugation through a 3,000 Da MWCO membrane using 0.5 mL centrifugal filtration tubes until no FITC was detected by UV-Vis in filtrate. Degree of labeling was 0.28 FITC per phytase as determined by UV absorbance (Schreiber and Haimovich, 1983).

Release of Phytase from Trehalose Hydrogel.

FITC-labeled phytase (74 mg/mL) in 0.1 M sodium acetate buffer (pH 5.0, 10 µL) was added to 4 mg of trehalose hydrogel. The mixture was incubated at 4° C. for 24 h, and then lyophilized. To the gel was added 1000 µL buffer to initiate the passive diffusion of the phytase from the hydrogel. Aliquots (200 µL) were taken at respective time points and the samples were immediately replenished with fresh buffer. The concentrations of the time point aliquots were calculated from the fluorescence measured on a spectrofluorometer using a FITC-labeled phytase calibration curve.

Heat Burden Studies of HRP and SET Hydrogel.

Horseradish peroxidase (HRP) stock solution was prepared in 75 µg/mL concentration in $H_2O$. The stock solution (66.6 µL) was added to the dried styrenyl ether trehalose hydrogel (SET hydrogel) to make 1:10 or 1:50 of HRP:SET hydrogel weight equivalent samples. Nonheated control samples without the hydrogel were stored at 4° C. until the activity assay. The HRP-hydrogel mixture was incubated at 4° C. for about 2 hours for the hydrogel to become fully hydrated. The hydrogel was heated at 70° C. at 500 rpm shaking for 30 min in a MSC-100 Thermo-shaker (Hangzhou Allsheng Instruments, Co., Ltd., China). The samples were then immediately cooled and incubated overnight in a 4° C. refrigerator. For the activity assay, 3,3',5,5'-tetramethylbenzidine (TMB) was used as the substrate and 1 M $H_2SO_4$ solution was used as the stop solution. Activity was measured from the absorbance at 450 nm. The study was conducted in total 12 times (n=12).

Preparation of HRP-AF488 for Confocal Microscope.

To the 100 µL horseradish peroxidase (HRP) solution (1 mg/mL) in pH 7.4 D-PBS, alexa Fluor® 488 TFP ester (AF488, 10 µL in 1 M sodium bicarbonate solution) was added. The reaction was incubated at 25° C. for 30 min and purified using centriprep tube (MWCO, 3,000 g/mol). The degree of labeling of HRP-AF488 after purification was 5.24. The prepared SET hydrogel from above was immersed into 100 µL HRP-AF488 at 4° C. for 12 h and after short wash with $H_2O$, confocal microscope image was taken.

Heat Burden Studies of Phytase.

To the dried hydrogel and phytase mixture, 53 wt % of $H_2O$ with respect to the phytase was added. The hydrogel was incubated at 4° C. for 24 h with gentle rocking to evenly distribute the solution. The hydrogel was then heated at 90° C. for 1 min, and diluted with 0.1 M sodium acetate buffer, pH 5, and incubated for at least 24 h prior to the activity assay.

Phytase Activity Assay.

The control and heat treated hydrogels (10 uL) were first diluted in 10 mL of 0.2 M sodium citrate pH 5.5 buffer, and 0.5 mL aliquots of diluted sample were transferred to each of four reaction tubes (1 blank and 3 sample). To all sample tubes, 0.5 mL of 1% phytic acid solution (0.2 M sodium citrate buffer, pH 5.5) was added and the tubes were incubated at 37° C. for 15 minutes. The reactions were then quenched by the addition of 1.0 ml of 15% trichloroacetic acid, and 0.5 mL of phytic acid was added to the blank tubes. Samples (30 uL) were diluted ten-fold with distilled water, and the diluted solutions (150 uL) were treated with 150 uL of 1:3:1 solution of 2.5% ammonium molybdate:10% sulfuric acid:10% ascorbic acid in a microtiter plate. The plate was incubated in a 50° C. water bath for 15 minutes, cooled at 4° C. for 15 minutes, and the 820 nm absorbance of individual wells were measured. Phytase activity (FTU) is defined as the amount of enzyme that catalyzes the release of 1.0 micromole of inorganic phosphate per minute from 1% phytic acid in pH 5.5 buffer at 37° C.

Statistical Analysis.

One-tailed Student's t-test assuming unequal sample variance was used. Results were considered significantly different if $p<0.05$.

Release of Phytase from Hydrogel that had not been Lyophilized.

FITC-labeled phytase (30 mg/mL) in 0.1 M sodium acetate buffer (pH 5.0) was added to 0.5 mg of trehalose hydrogel to fully hydrate the gel (25 µL water per 1 mg of hydrogel). The mixture was incubated at room temperature for 12 h, and then 200 µL buffer was added to initiate the passive diffusion of the phytase from the hydrogel. Half of the solution was removed at various time points and fresh buffer was added. The concentrations of the time point aliquots were calculated from the fluorescence measured on a spectrofluorometer using a FITC-labeled phytase calibration curve.

Synthesis of Trehalose Monomer and Crosslinker

Synthesis of Crude SET

Simple synthesis and purification steps are one of the most important factors in industrial scale reactions. Originally, we purified the trehalose monomers by precipitating the reaction mixture into DCM followed further purification to remove all the side products, some of which have degree of substitution (DS) over two. However, we envisioned synthesis of trehalose-based hydrogel directly using these side products as crosslinkers (Scheme 6). Due to the presence of crosslinker in the monomer, the product in this case would be a hydrogel rather than a linear polymer. In this chapter, we describe hydrogel synthesis using SET monomer, since a crude mixture of monomer and crosslinker could be produced from the starting materials 4-vinylbenzyl chloride and trehalose in one step (Teramoto and Shibata, 2004). First, 4-vinylbenzyl chloride was reacted with excess trehalose under basic conditions. The resulting crude mixture was then precipitated into DCM and filtered to remove DMSO and trehalose with a high DS. The crude product contained several regioisomers (trehalose with styrene at the $2^{nd}$, $4^{th}$ and $6^{th}$ position), bis-functionalized and trifunctionalized trehalose, as well as unmodified trehalose. The crude SET was then directly used for gelation.

Synthesis of SET Hydrogel

Figure 11:
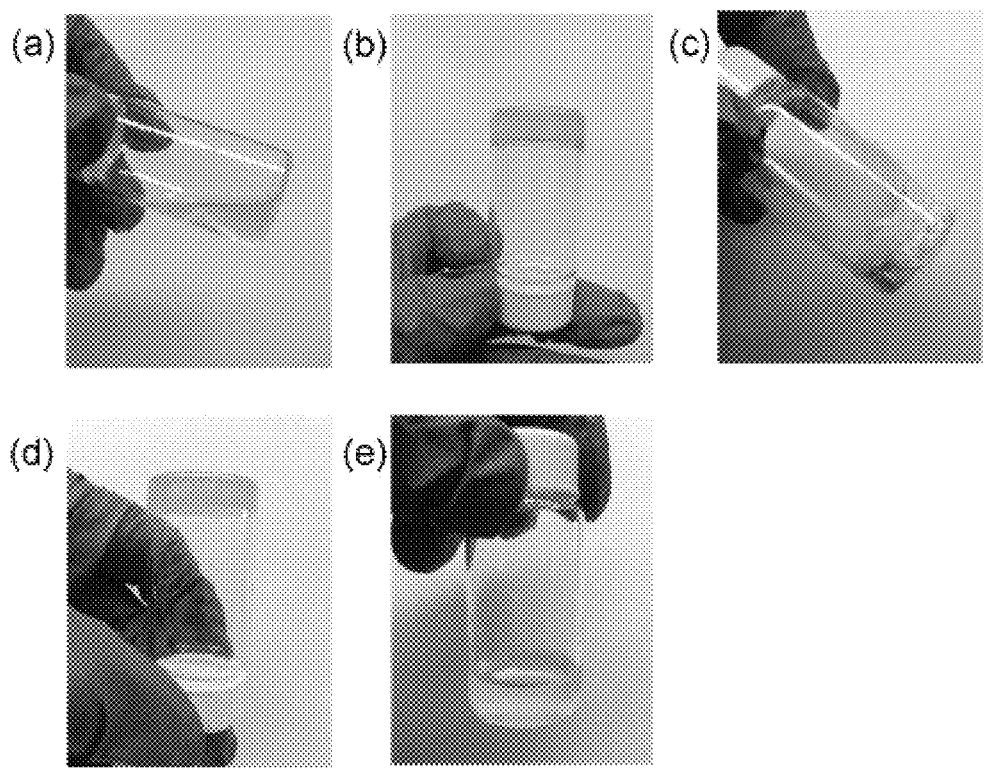
FIG. 11 (a-e) is a set of photographs showing (a) Crude SET and TEMED dissolved in $H_2O$, (b) after adding APS, (c) after lyophilizing the hydrogel, (d) immersing lyophilized gel again into the $H_2O$, and (e) after washing the hydrogel (grounded after lyophilization and immersed in $H_2O$).
Figure 12:
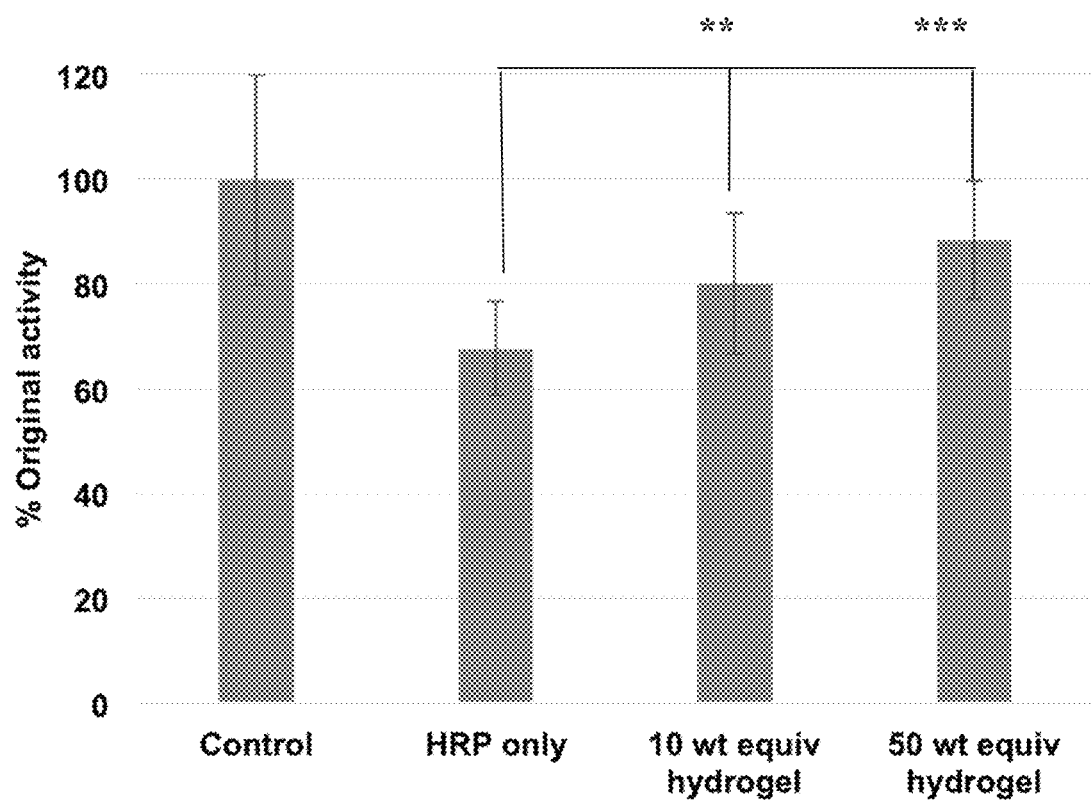
FIG. 12 is a graph showing activity of HRP before heating (control) and after heating at 70° C. for 30 min with no additive, 10 wt equiv, or 50 wt equiv of SET hydrogel to the protein.

Polymerization with ammonium persulfate (APS) and tetramethylenediamine (TEMED) as radical initiators was used to form a SET hydrogel from the crude SET (Scheme 7). The crude SET was dissolved in $H_2O$ at 1 mg/mL concentration and TEMED was added (FIG. 11a). Initially the solution remained in the sol phase. However, after adding APS the solution started gelating within 10 min at 25° C. (FIG. 11b). The resulting hydrogel had the same yellow color as the crude mixture. The hydrogel network remained intact after lyophilization and re-immersion into $H_2O$ (FIGS. 11c and 11d). Extensive washing with $H_2O$ removed the yellow color, resulting in a colorless SET hydrogel (FIG. 11e). Using a mortar, the purified SET hydrogel was then ground into a powder to increase the surface area for protein stabilization and also for ease of handling. HRP was then incubated with the protein at 70 degrees C. for 30 minutes and the activity of the protein was subsequently determined. It was found that the protein was significantly more active in the presence of the hydrogel compared to no additive (FIG. 12).

Discussion

The data demonstrate that the SET hydrogel can stabilize HRP against extreme HRP. The advantage of utilizing the hydrogel is that its synthesis avoids purification of the monomer by HPLC. Another advantage of hydrogel formulation is its ease of removal. Since the hydrogel is not soluble in $H_2O$ or organic solvents it can be separated from the mixture by simple filtration or centrifugation. The SET hydrogel-2 may stabilize a wide range of enzymes and proteins that need to undergo harsh thermal treatment. Since our group has already demonstrated stabilization of various proteins against heating using linear trehalose polymers, the trehalose-based hydrogel described may be readily applicable to thermal stabilization of other industrially important enzymes or proteins (Mancini et al., 2012; Lee et al., 2013).

Figure 13:
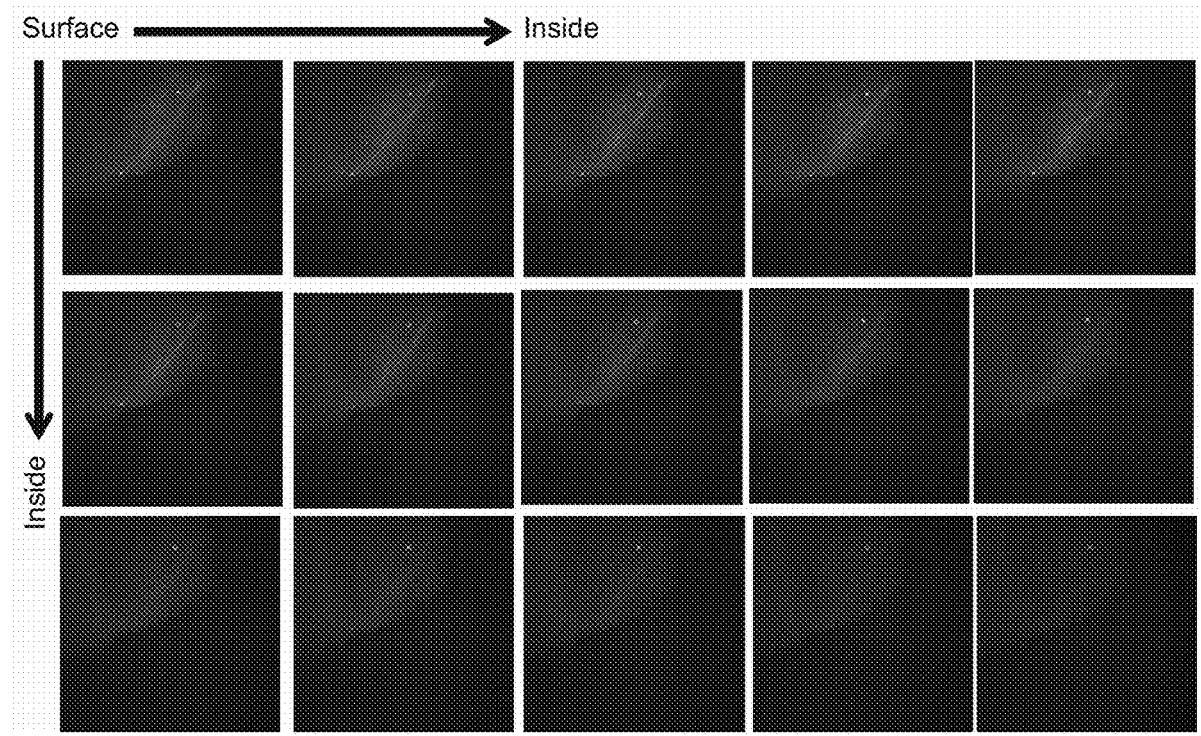
FIG. 13 is a set of photographs showing axial confocal microscopy images (15 scans) of the edge of the SET hydrogel-2 immersed in HRP-AF488 (green) solution (axial resolution of 25 μm) for 24 h and then briefly washed.

Even though we have shown that the SET hydrogel can stabilize phytase against heating, we have yet to confirm whether phytase is located inside the gel or adsorbed on the surface. To begin to determine the location of the protein, we used HRP modified with Alexa Fluor® 488 tetrafluorophenyl ester (AF488) as a model system. The SET hydrogel with HRP-AF488 was prepared in a similar manner to the SET hydrogel that showed 100% stabilization of phytase. As shown in FIG. 13, the preliminary confocal microscopy images indicated that the HRP-AF488 is present inside the hydrogel.

Conclusion

We have detailed the synthesis of a trehalose hydrogel for industrial-scale stabilization of proteins. This hydrogel can be prepared via simple synthesis and purification steps, which is a important consideration in industrial processes. The trehalose hydrogel is a promising system for stabilizing various enzymes or proteins against the pelleting procedure or other high-temperature processes.

Trehalose Hydrogels for Stabilization of Enzymes to Heat

Enzymes can catalyze various reactions with high selectivity and are involved in many important biological processes. However, the general instability of enzymes against high temperature often limits their application. To address this, we synthesized a trehalose-based hydrogel in two steps from commercial starting materials with minimal purification procedures. Mono- and multi-functional trehalose monomers were cross-linked by redox-initiated radical polymerization to form a hydrogel. Phytase, an important enzyme utilized in animal feedstock, was employed to study the effectiveness of the trehalose hydrogel to stabilize proteins against heat. Addition of the phytase solution to the hydrogel resulted in enzyme internalization as confirmed by confocal microscopy. The phytase in the hydrogel retained 100% activity upon heating at 90° C. compared to 39% when the hydrogel was absent. The enzyme could also be recovered from the hydrogel. The trehalose hydrogel synthesis reported herein should be readily scalable for thermal stabilization of a wide variety of enzymes.

Results and Discussion

Figure 20:
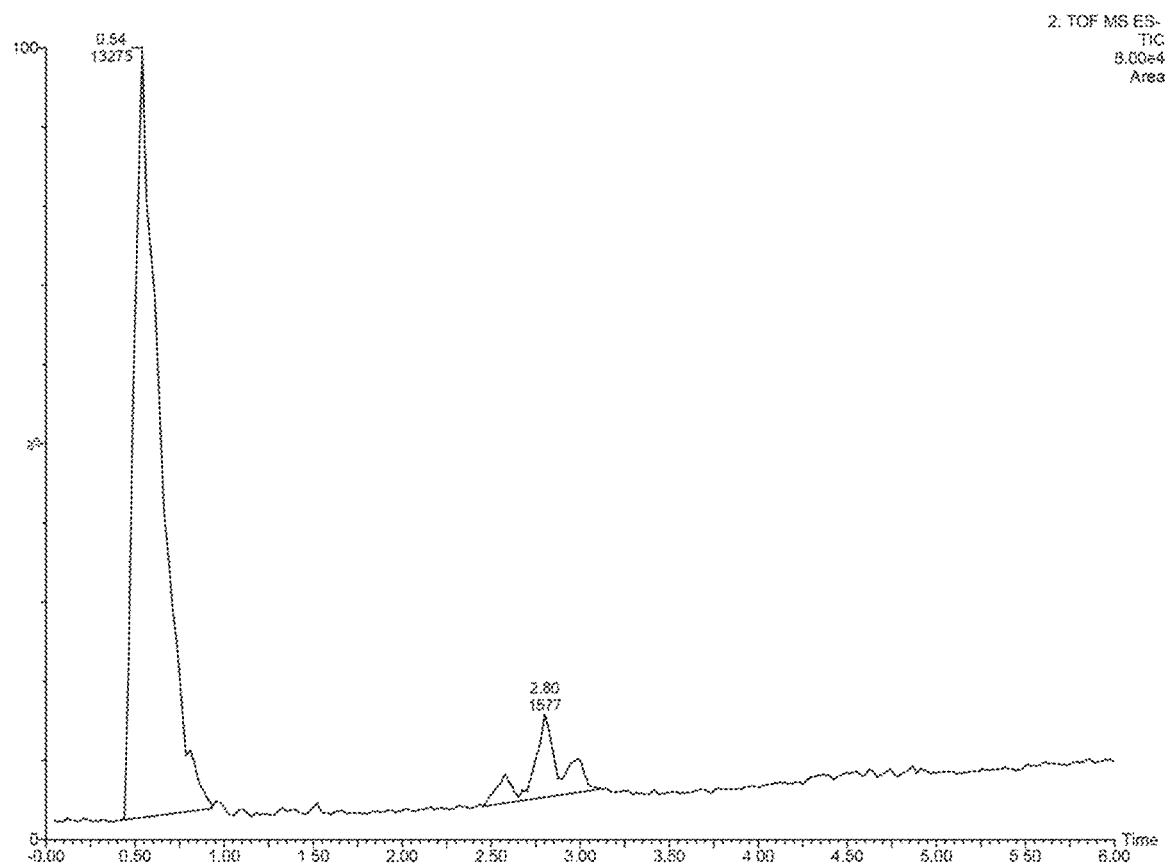
FIG. 20 is a graph showing LC-MS chromatogram of the trehalose hydrogel reaction mixture after 1 day.
Figure 21:
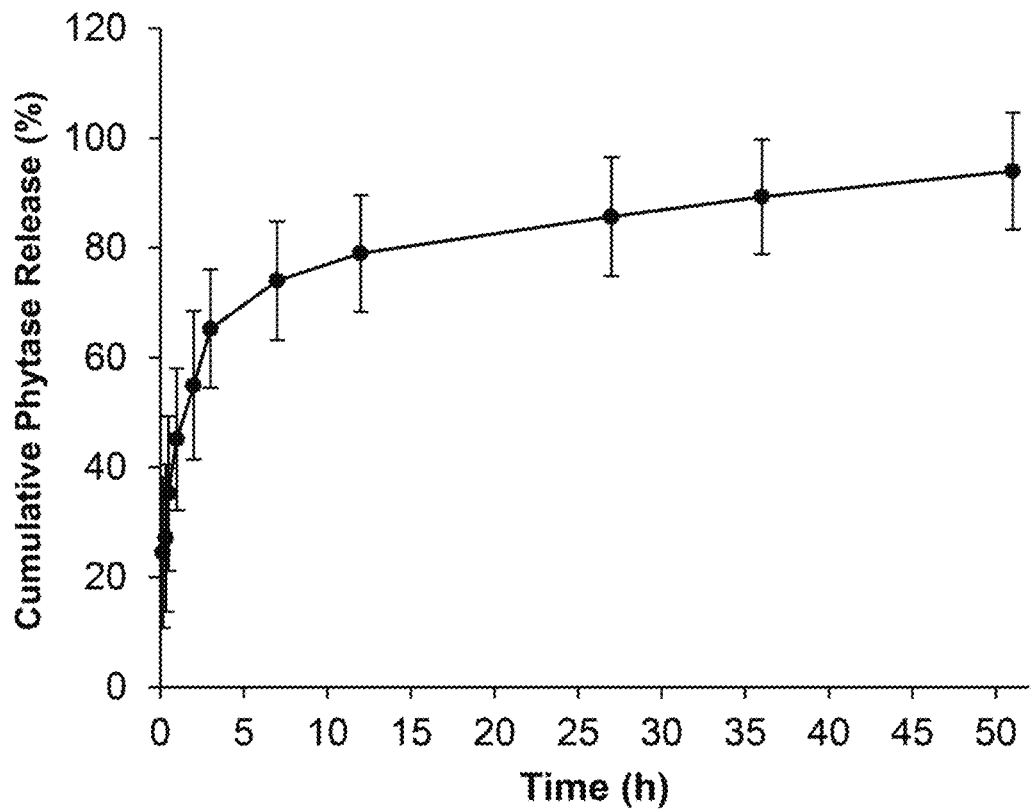
FIG. 21 is a graph showing release profile of FITC-labeled phytase from trehalose hydrogel prior to lyophilization (n=6).
Figure 22:
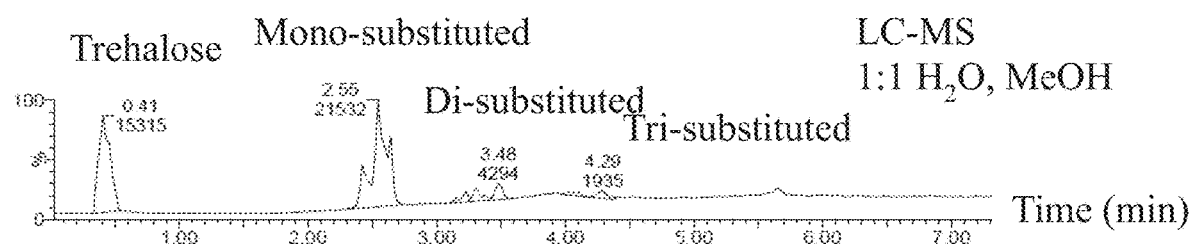
FIG. 22 is a graph showing LC-MS chromatogram of synthesis of the first step monomer synthesis in the trehalose-based hydrogel yielding various regioisomers of mono-, di-, and tri-substituted trehalose.
Figure 23:
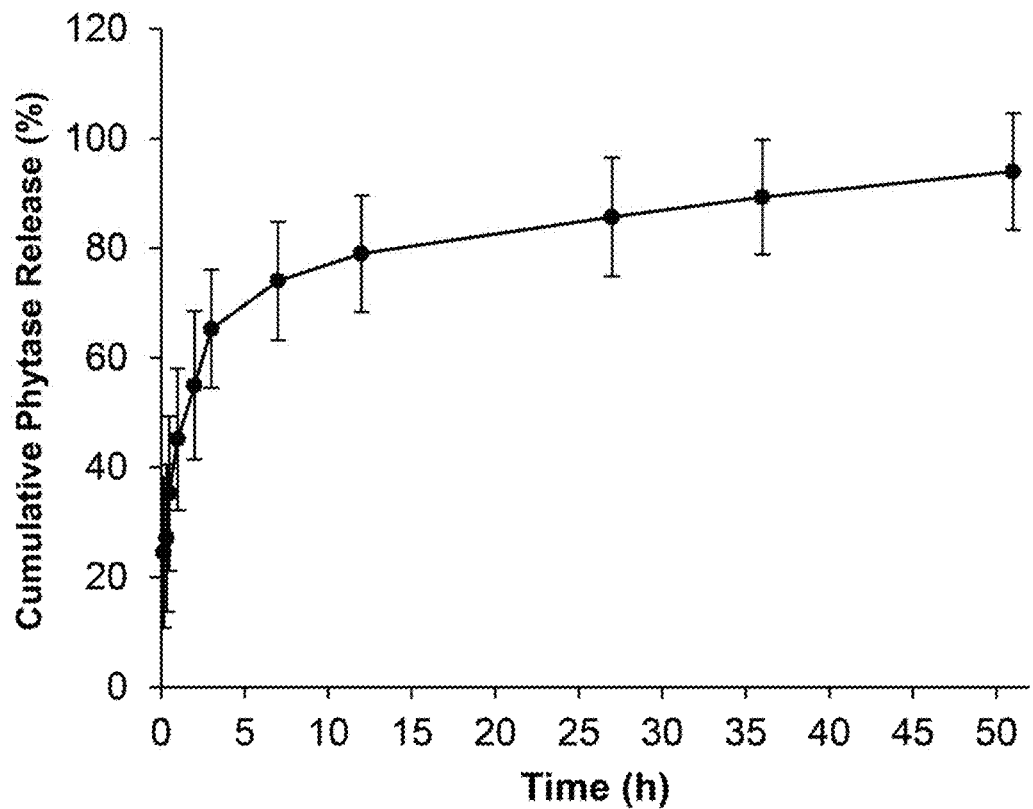
Figure 24:
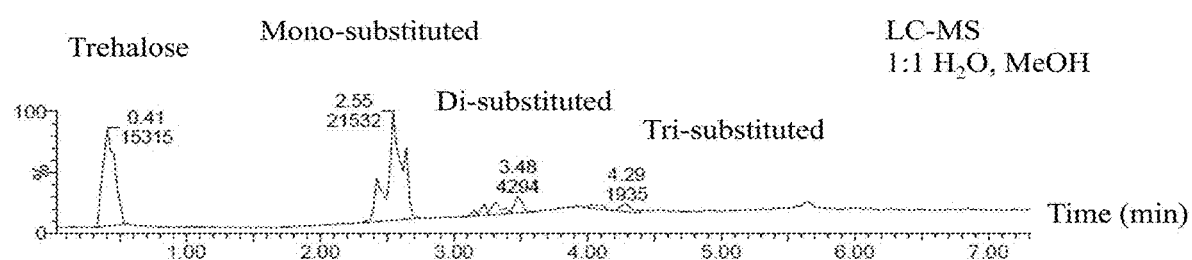

Straightforward synthesis, commercially available starting materials, and simple purification steps are some of the most important factors in industrial-scale reactions (Kuttruff et al., 2014). Thus, the hydrogel was synthesized in only two steps. First, Williamson etherification using 4-vinylbenzyl chloride and trehalose yielded a crude product mixture that was subsequently precipitated into DCM. The DCM wash contained mostly DMSO and some trehalose and mono- and di-substituted products, while the precipitate that was used for gelation consisted of unmodified trehalose and vinyl-substituted products (79% mono-substituted, 16% di-substituted, and 5% tri-substituted) as measured by HPLC and LCMS (FIGS. 20 and 21 and Table 1). We envisioned that the multi-substituted products of the crude monomer reaction mixture could be used as cross-linkers to synthesize a trehalose-based hydrogel directly from the crude reaction mixture (Scheme 6 and Scheme 7). Due to the presence of cross-linkers, polymerization would yield a hydrogel rather than a linear polymer.

The crude mixture was then polymerized by radical polymerization using a redox initiator pair, APS and TEMED. The crude mixture was dissolved in water with TEMED (FIG. 11a). After the addition of APS, the solution started gelling within 10 min at 25° C. (FIG. 11b). The resulting hydrogel had the same yellow color as the crude mixture. The hydrogel network remained intact after lyophilization and rehydration (FIGS. 11c and 11d). After 1 day, all of the di- and tri-substituted trehalose had reacted (FIG. 20). The crude gel was washed with a Soxhlet extractor for 3 days to remove unreacted monomers, residual initiator and trehalose, yielding a colorless hydrogel. The purified trehalose hydrogel was grounded into a powder with a mortar and pestle for ease of handling and to increase the surface area for internalization of phytase (FIG. 11e).

TABLE 1

Figure 19:
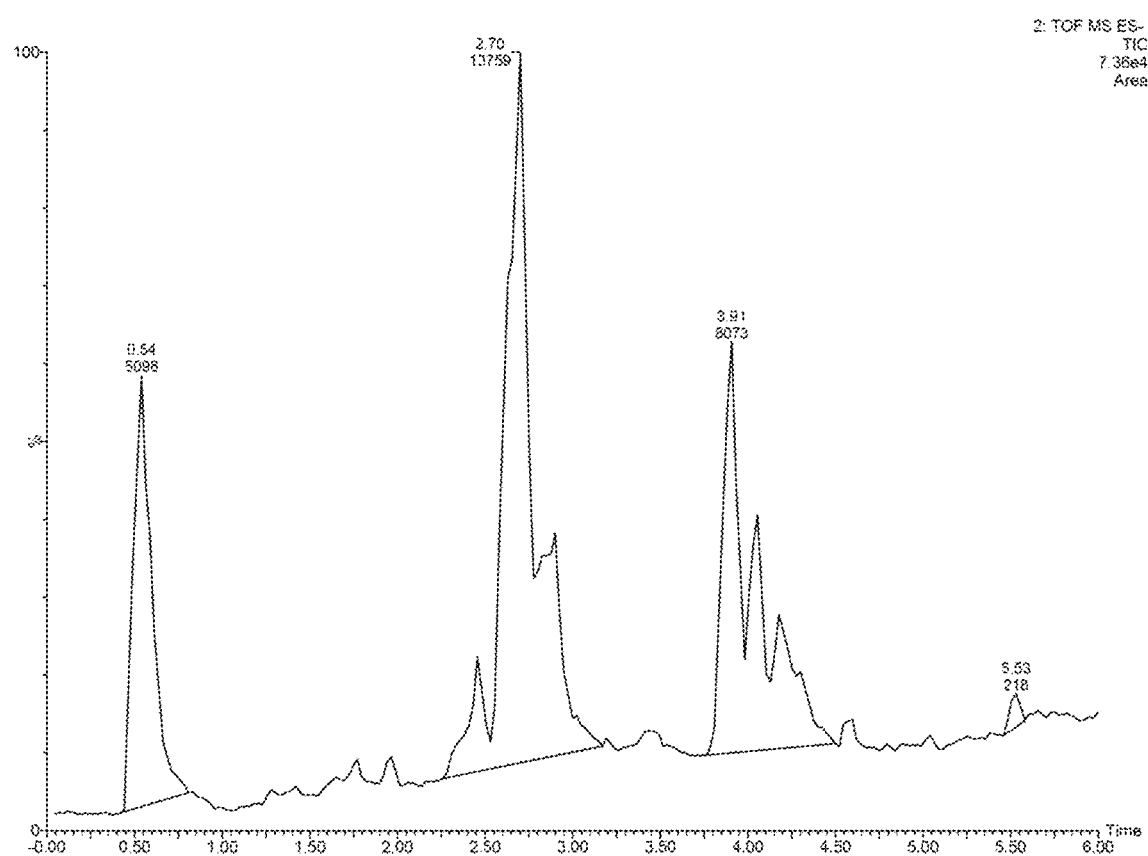
FIG. 19 is a graph showing LC-MS chromatogram of the DCM wash of the crude styrenyl ether trehalose mixture.

Theoretical and observed masses of [M + HCOO]⁻ ion of trehalose and its derivatives from LC-MS chromatogram in FIG. 19

|  | Retention time (min) | Theoretical mass (m/z) | Observed mass (m/z) | Δ m/z (ppm) |
|---|---|---|---|---|
| Trehalose | 0.6 | 387.1139 | 387.1143 | −1.1 |
| Mono- | 2.5 | 503.1765 | 503.1762 | 0.5 |
| substituted | 2.8 | 503.1765 | 503.1720 | 8.9 |
|  | 2.9 | 503.1765 | 503.1765 | −0.1 |
| Di-substituted | 4.4 | 619.2391 | 619.2369 | 3.5 |
| Tri-substituted | 5.5 | 735.3017 | 735.3012 | 0.6 |

Figure 14:
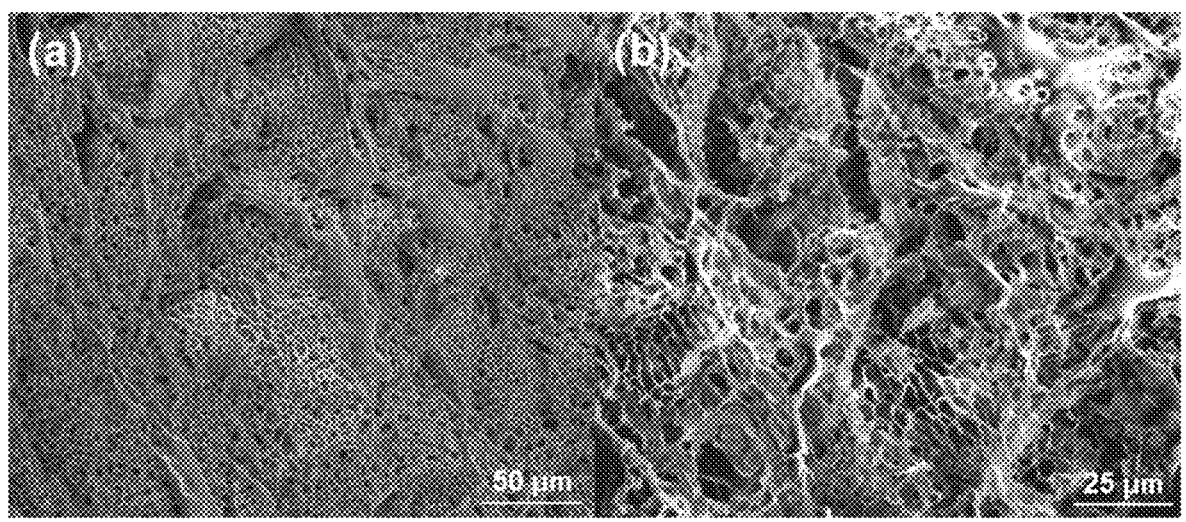
FIG. 14 (a and b) is a set of photographs showing SEM images of trehalose hydrogel. (a) Images at 500× magnification and (b) at 1000× magnification.

The purified hydrogel was characterized by a variable pressure SEM, as shown in FIG. 14. The images revealed hydrogel architecture with micron-sized pores. Since phytase diameter is approximately 11.1 nm along the major axis as measured from the crystal structure (PDB: 1DKL)

Figure 15:
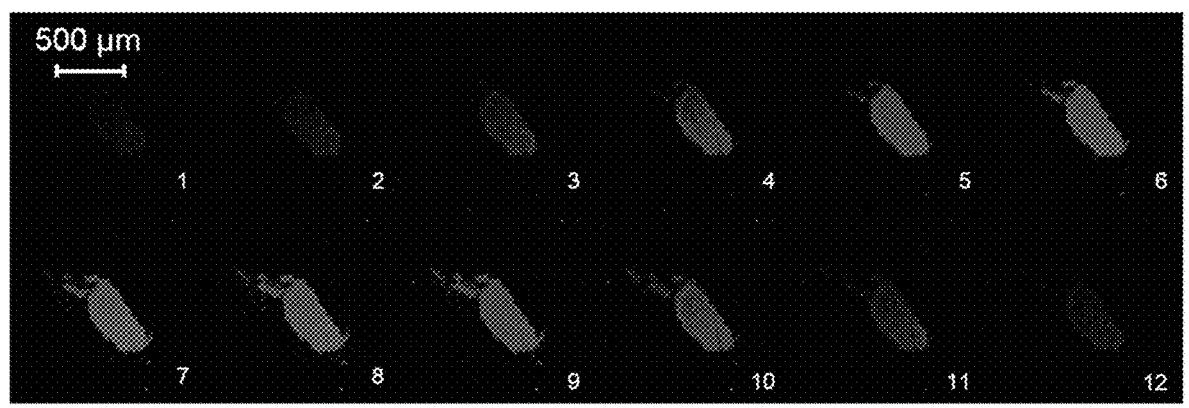
FIG. 15 is a photograph showing confocal images of trehalose hydrogel incubated overnight in a solution containing FITC-labeled phytase and washed with deionized water. Numbers in the lower right corner indicate transaxial slice indices. Axial resolution=2 μm.
Figure 16:
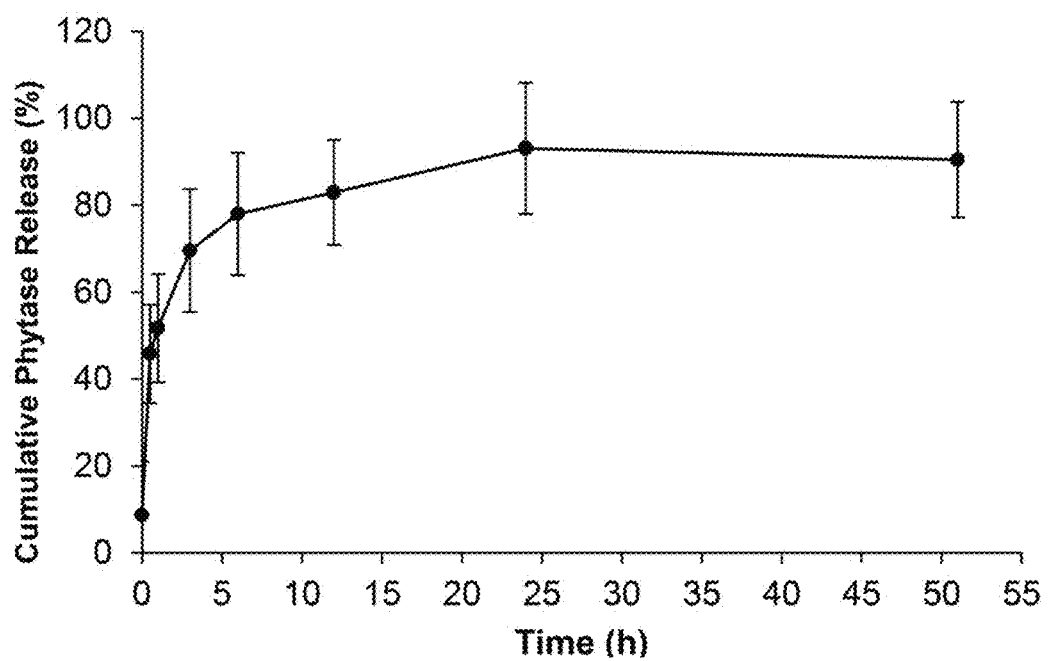
FIG. 16 is a graph showing release profile of FITC-labeled phytase from trehalose hydrogel after loading and lyophilization (n=6).

(Oakley, 2010), phytase was thus expected to be incorporated within the hydrogel. To test this hypothesis, we observed the hydrogel under a confocal microscope after incubation in fluorescein isothiocyanate (FITC)-labeled phytase solution followed by a brief wash in water (FIG. 15). An even distribution of the fluorophore throughout the gel matrix demonstrated that the phytase was fully internalized into the hydrogel and not simply adsorbed on the hydrogel surface. Because of the pore size, we anticipated that the enzyme would be released from the hydrogel when diluted with water. Indeed, the release profile of FITC-labeled phytase from the hydrogel after lyophilization showed that 78% of the phytase was released in 6 hours (FIG. 16). The release profile was similar to gel that has not been lyophilized (FIG. 21). The results providing further evidence that the phytase is internalized inside the hydrogel and also demonstrate that the gel can be used to recover enzyme after loading.

Currently in the animal feed industry, pelleting is the most common process for preparing animal feeds since it improves their efficiency and reduces nutrient excretion compared to mashed forms (Nahm, 2002; Thomas and Van der Poel, 1996). Typically temperatures reach 70-90° C. for a few minutes during pelleting. For phytase in particular, the dry ingredients including phytase are mixed in a pelleting mill conditioner, reaching a temperature of 80-90° C. for 35-45 sec, followed by extrusion to produce the desired pellets. Thus, phytase was loaded into the hydrogel and heated in a condition simulating the steam pelleting process (90° C., 1 min). The phytase solution was added to three different weight equivalents (1, 10, and 40) of lyophilized trehalose hydrogel and incubated for 24 h. The sample was lyophilized again, 53 wt % of water was added to the phytase-loaded trehalose hydrogel, and the gel was incubated for another 24 h to replicate the moisture level of the steam heating process. The water is essential for the pelleting process, but it also expedites denaturation of phytase under the extreme heating (Lee et al., 2013; Slominski et al., 2007). The results showed that phytase heated in the presence of the hydrogel retained significantly higher activity for all weight equivalents tested. Even when only 1 weight equivalent of hydrogel was used, 81% activity was retained compared to the control that had not been heated which was only 39% active, and 10 and 40 wt eq retained 100% enzyme activity (FIG. 17). The average activity indicated that 10 weight equivalent of hydrogel to phytase was the optimal amount to completely retain the original phytase activity, while utilizing the minimal amount of hydrogel.

The results demonstrated that the trehalose hydrogel can stabilize phytase against extreme heat conditions. The trehalose hydrogel may be suitable for industrial-scale applications as the synthesis only requires two steps and involves minimal purification that can be easily adapted to a large scale. Specifically, the proposed method uses chromatography-free purification, easily accessible starting materials, protecting group-free chemistry, and a minimal number of steps (Kuttruff et al., 2014).

Another advantage of hydrogel formulation is its ease of removal. The release results demonstrate that the protein of interest can be removed from the hydrogel. The release occurred over several hours with ~80% release at 6 hours. However, this is with passive diffusion. Since the hydrogel is not soluble in water or organic solvents, it can be separated from the mixture by simple filtration or centrifugation. One can anticipate that by rinsing or pushing water through the system, or with the agitation that occurs in the gastrointestinal track in the case of phytase-loaded hydrogel, the enzyme would be released faster. This is a potential advantage of the system since the hydrogel could be added and then removed from the protein after stress if so desired.

In addition, despite much research on the genetic engineering of enzymes for improving their thermal stability, multiple optimization iterations or enzyme-specific mutation strategies are usually required, accompanied with a higher cost (Himmel et al., 2007). Thus, the strategy described herein may be more flexible and cost effective than genetic engineering techniques. Since our group has already demonstrated that linear trehalose polymers stabilize various proteins against heating (Lee et al., 2013; Mancini et al., 2013), the trehalose-based hydrogel hereby described may be readily applicable to thermal stabilization of a wide variety of industrially important enzymes and proteins.

CONCLUSIONS

We have detailed the synthesis of a trehalose hydrogel for thermal stabilization of phytase as a model enzyme. This hydrogel can be prepared via simple synthesis and purification steps, which are important considerations in industrial processes. The resulting trehalose hydrogel fully preserved the activity of phytase under temperatures relevant in the pelleting procedure for animal feed preparation. Currently, many enzymes in animal feeds lose the majority of their activity during this steam pelleting process. As demonstrated by the stabilization of phytase in this report, the trehalose hydrogel is a promising material for stabilizing various enzymes and proteins against high-temperature processes.

REFERENCES

1. G. N. Somero, *Annu. Rev. Physiol.*, 1995, 57, 43-68.
2. A. J. Rader, B. M. Hespenheide, L. A. Kuhn and M. F. Thorpe, *Proc. Natl. Acad. Sci. U.S.A.*, 2002, 99, 3540-3545.
3. C. Ó. Fágáin, *BBA-Protein Struct. M.*, 1995, 1252, 1-14.
4. V. Ravindran and J.-H. Son, *Recent Pat. Food Nutr. Agric.*, 2011, 3, 102-109.
5. H. Samejima, K. Kimura and Y. Ado, *Biochimie*, 1980, 62, 299-315.
6. A. Schmid, J. S. Dordick, B. Hauer, A. Kiener, M. Wubbolts and B. Witholt, *Nature*, 2001, 409, 258-268.
7. G. DeSantis and J. B. Jones, *Curr. Opin. Biotechnol.*, 1999, 10, 324-330.
8. O. Ryan, M. R. Smyth and C. O. Fagain, *Enzyme Microb. Tech.*, 1994, 16, 501-505.
9. P. Frosst, H. J. Blom, R. Milos, P. Goyette, C. A. Sheppard, R. G. Matthews, G. J. H. Boers, M. Denheijer, L. A. J. Kluijtmans, L. P. Vandenheuvel and R. Rozen, *Nat. Genet.*, 1995, 10, 111-113.
10. B. W. Matthews, H. Nicholson and W. J. Becktel, *Proc. Natl. Acad. Sci. U.S.A.*, 1987, 84, 6663-6667.
11. S. Kumar, C. J. Tsai and R. Nussinov, *Protein Eng.*, 2000, 13, 179-191.
12. T. Imanaka, M. Shibazaki and M. Takagi, *Nature*, 1986, 324, 695-697.
13. H. F. Gaertner and A. J. Puigserver, *Enzyme Microb. Tech.*, 1992, 14, 150-155.
14. M. A. Longo and D. Combes, *J. Chem. Technol. Biot.*, 1999, 74, 25-32.
15. Z. Yang, M. Domach, R. Auger, F. X. Yang and A. J. Russell, *Enzyme Microb. Tech.*, 1996, 18, 82-89.
16. D. Kazan and A. Erarslan, *Appl. Biochem. Biotech.*, 1997, 62, 1-13.

17. S. Tomita, Y. Nagasaki and K. Shiraki, *Biotechnol. Bioeng.*, 2012, 109, 2543-2552.
18. R. A. Sheldon, *Adv. Synth. Catal.*, 2007, 349, 1289-1307.
19. K. Akiyoshi, Y. Sasaki and J. Sunamoto, *Bioconjug. Chem*, 1999, 10, 321-324.
20. Q. Wang, Z. Yang, Y. Gao, W. Ge, L. Wang and B. Xu, *Soft Matter*, 2008, 4, 550-553.
21. K. Lippert and E. Galinski, *Appl. Microbiol. Biotechnol.*, 1992, 37, 61-65.
22. J. K. Kaushik and R. Bhat, *J. Biol. Chem.*, 2003, 278, 26458-26465.
23. R. P. Baptista, S. Pedersen, G. J. Cabrita, D. E. Otzen, J. M. Cabral and E. P. Melo, *Biopolymers*, 2008, 89, 538-547.
24. N. Guo, I. Puhlev, D. R. Brown, J. Mansbridge and F. Levine, *Nat. Biotechnol.*, 2000, 18, 168-171.
25. S. Hengherr, A. G. Heyer, H. R. Kohler and R. O. Schill, *FEBS J.*, 2008, 275, 281-288.
26. J. H. Crowe, L. M. Crowe and D. Chapman, *Science*, 1984, 223, 701-703.
27. G. M. Beattie, J. H. Crowe, A. D. Lopez, V. Cirulli, C. Ricordi and A. Hayek, *Diabetes*, 1997, 46, 519-523.
28. P. Sundaramurthi and R. Suryanarayanan, *J. Phys. Chem. Lett.*, 2009, 1, 510-514.
29. T. Duong, R. Barrangou, W. M. Russell and T. R. Klaenhammer, *Appl. Environ. Microbiol.*, 2006, 72, 1218-1225.
30. P. Westh and H. Ramlev, *J. Exp. Zool.*, 1991, 258, 303-311.
31. K. A. C. Madin and J. H. Crowe, *J. Exp. Zool.*, 1975, 193, 335-342.
32. N. K. Jain and I. Roy, *Protein Sci.*, 2009, 18, 24-36.
33. S. Ohtake and Y. J. Wang, *J. Pharm. Sci.*, 2011, 100, 2020-2053.
34. J. Lee, E. W. Lin, U. Y. Lau, J. L. Hedrick, E. Bat and H. D. Maynard, *Biomacromolecules*, 2013, 14, 2561-2569.
35. X. G. Lei, J. D. Weaver, E. Mullaney, A. H. Ullah and M. J. Azain, *Annu. Rev. Anim. Biosci.*, 2013, 1, 283-309.
36. I. Kuhn and K. Partanen, *J. Anim. Sci.*, 2012, 90, 194-196.
37. K. H. Nahm, *Crit. Rev. Env. Sci. Technol.*, 2002, 32, 1-16.
38. F. G. Silversides, T. A. Scott and M. R. Bedford, *Poult. Sci.*, 2004, 83, 985-989.
39. O. Adeola and A. J. Cowieson, *J. Anim. Sci.*, 2011, 89, 3189-3218.
40. B. A. Slominski, T. Davie, M. C. Nyachoti and O. Jones, *Livestock Sci.*, 2007, 109, 244-246.
41. K. P. Hughes and J. H. Soares, Jr., *Aquacult. Nutr.*, 1998, 4, 133-140.
42. L. Cao, W. Wang, C. Yang, Y. Yang, J. Diana, A. Yakupitiyage, Z. Luo and D. Li, *Enzyme Microb. Technol.*, 2007, 40, 497-507.
43. D. Lim, S. Golovan, C. W. Forsberg and Z. Jia, *Nat. Struct. Biol.*, 2000, 7, 108-113.
44. N. Guex and M. C. Peitsch, Electrophoresis, 1997, 18, 2714-2723.
45. C. A. Kuttruff, M. D. Eastgate and P. S. Baran, *Nat. Prod. Rep.*, 2014, 31, 419-432.
46. A. J. Oakley, *Biochem. Biophys. Res. Commun.*, 2010, 397, 745-749.
47. M. Thomas and A. Van der Poel, *Anim. Feed Sci. Tech.*, 1996, 61, 89-112.
48. M. E. Himmel, S. Y. Ding, D. K. Johnson, W. S. Adney, M. R. Nimlos, J. W. Brady and T. D. Foust, *Science*, 2007, 315, 804-807.
49. Guan, Y.; Zhang, Y. *Chem. Soc. Rev.* 2013, 42, 8106.
50. Ravaine, V.; Ancla, C.; Catargi, B. *J. Control. Release* 2008, 132, 2.
51. Kuivila, H. G.; Keough, A. H.; Soboczenski, E. J. *J. Org. Chem.* 1954, 19, 780.
52. Springsteen, G.; Wang, B. H. *Tetrahedron* 2002, 58, 5291.
53. Yan, J.; Springsteen, G.; Deeter, S.; Wang, B. *Tetrahedron* 2004, 60, 11205.
54. Barker, S. A.; Chopra, A. K.; Hatt, B. W.; Somers, P. J. *Carbohydr. Res.* 1973, 26, 33.
55. Matsumoto, A.; Yamamoto, K.; Yoshida, R.; Kataoka, K.; Aoyagi, T.; Miyahara, Y. *Chem. Commun.* 2010, 46, 2203.
56. Wang, D.; Liu, T.; Yin, J.; Liu, S. *Macromolecules* 2011, 44, 2282.
57. Ancla, C.; Lapeyre, V.; Gosse, I.; Catargi, B.; Ravaine, V. *Langmuir* 2011, 27, 12693.
58. Zhang, C.; Losego, M. D.; Braun, P. V. *Chem. Mater.* 2013, 25, 3239.
59. Yuan, W.; Shen, T.; Wang, J.; Zou, H. *Polymer Chemistry* 2014, 5, 3968.
60. Yang, T.; Ji, R.; Deng, X.-X.; Du, F.-S.; Li, Z.-C. *Soft Matter* 2014, 10, 2671.
61. Vandenberg, R.; Peters, J. A.; Vanbekkum, H. *Carbohydr. Res.* 1994, 253, 1.
62. Roy, I.; Gupta, M. N. *Chem. Biol.* 2003, 10, 1161.
63. Bajpai, A. K.; Shukla, S. K.; Bhanu, S.; Kankane, S. *Prog. Polym. Sci.* 2008, 33, 1088.
64. Gupta, P.; Vermani, K.; Garg, S. *Drug Discov. Today* 2002, 7, 569.
65. Qiu, Y.; Park, K. *Adv. Drug Delivery Rev.* 2001, 53, 321.
66. Kiyonaka, S.; Sugiyasu, K.; Shinkai, S.; Hamachi, I. *J. Am. Chem. Soc.* 2002, 124, 10954.
67. Mano, J. F. *Advanced Engineering Materials* 2008, 10, 515.
68. Ingber, D. E.; Prusty, D.; Frangioni, J. V.; Cragoe, E. J.; Lechene, C.; Schwartz, M. A. *J. Cell Biol.* 1990, 110, 1803.
69. Wei, F.; Zhuyuan, W.; Shenfei, Z.; Hui, C.; Dan, Z.; Yuan, Z.; Yiping, C. Biosens. Bioelectron. 2014, 57, 10.
70. Lowman, A. M.; Morishita, M.; Kajita, M.; Nagai, T.; Peppas, N. A. *J. Pharm. Sci.* 1999, 88, 933.
71. Patel, V.; Amiji, M. *Pharm. Res.* 1996, 13, 588.
72. Besheer, A.; Wood, K. M.; Peppas, N. A.; Mader, K. *J. Control. Release* 2006, 111, 73.
73. Guo, B.-L.; Gao, Q.-Y. *Carbohydr. Res.* 2007, 342, 2416.
74. Nho, Y. C.; Park, S. E.; Kim, H. I.; Hwang, T. S. *Nuclear Instruments & Methods in Physics Research Section B-Beam Interactions with Materials and Atoms* 2005, 236, 283.
75. Sajeesh, S.; Sharma, C. P. *Journal of Biomedical Materials Research Part B-Applied Biomaterials* 2006, 76B, 298.
76. Shantha, K. L.; Harding, D. R. K. *Int. J. Pharm.* 2000, 207, 65.
77. Teramoto, N.; Sachinvala, N. D.; Shibata, M. *Molecules* 2008, 13, 1773.
78. Bachelder, E. M.; Beaudette, T. T.; Broaders, K. E.; Dashe, J.; Fréchet, J. M. J. *J. Am. Chem. Soc.* 2008, 130, 10494.
79. Li, R. C.; Broyer, R. M.; Maynard, H. D. *Journal of Polymer Science Part A: Polymer Chemistry* 2006, 44, 5004.
80. Murthy, N.; Thng, Y. X.; Schuck, S.; Xu, M. C.; Fréchet, J. M. J. *J. Am. Chem. Soc.* 2002, 124, 12398.

81. Chen, W.; Meng, F.; Cheng, R.; Zhong, Z. *J. Control. Release* 2010, 142, 40.
82. Fife, T. H.; Jao, L. K. *The Journal of Organic Chemistry* 1965, 30, 1492.
83. Teramoto, N.; Shibata, M. *J. Appl. Polym. Sci.* 2004, 91, 46.
84. Brown, L. R. *Expert. Opin. Drug. Del* 2005, 2, 29-42.
85. Burdick, J.; Chase, H. P.; Slover, R. H.; Knievel, K.; Scrimgeour, L.; Maniatis, A. K.; Klingensmith, G. J. *Pediatrics* 2004, 113, e221-224.
86. Wu, Q.; Wang, L.; Yu, H.; Wang, J.; Chen, Z. *Chem. Rev.* 2011, 111, 7855-7875.
87. Cambre, J. N.; Sumerlin, B. S. *Polymer* 2011, 52, 4631-4643.
88. Matsumoto, A.; Ishii, T.; Nishida, J.; Matsumoto, H.; Kataoka, K.; Miyahara, Y. *Angew. Chem. Int. Edit.* 2012, 51, 2124-2128.
89. Bapat, A. P.; Roy, D.; Ray, J. G.; Savin, D. A.; Sumerlin, B. S. *J. Am. Chem. Soc.* 2011, 133, 19832-19838.
90. Wang, Y. Chai., Z.; Ma, L.; Shi, C.; Shen, T.; Song, J. *RSC Adv.* 2014, 4, 53877-53884.
91. Pryce, R. *BMJ* 2009, 338:a2218.
92. Weiss, R. C.; van Amerongen, D.; Bazalo, G.; Aagren, M.; Bouchard, J. R. *Managed care* 2011, 20, 42-47.
93. Hinds, K. D.; Kim, S. W. *Adv. Drug Delivery Rev.* 2002, 54, 505-530.
94. Heise, T.; Nosek, L.; Spitzer, H.; Heinemann, L.; Niemoller, E.; Frick, A. D.; Becker, R. H. *Diabetes Obes. Metab.* 2007, 9, 746-753.
95. Leobandung, W.; Ichikawa, H.; Fukumori, Y.; Peppas, N. A. *J. Control. Release* 2002, 80, 357-363.
96. Akiyoshi, K.; Kobayashi, S.; Shichibe, S.; Mix, D.; Baudys, M.; Kim, S. W.; Sunamoto, J. *J. Control. Release* 1998, 54, 313-320.
97. Lee, J.; Lin, E. W.; Lau, U. Y.; Hedrick, J. L.; Bat, E.; Maynard, H. D. *Biomacromolecules* 2013, 14, 2561-2569.
98. Mancini, R. J.; Lee, J.; Maynard, H. D. *J. Am. Chem. Soc.* 2012, 134, 8474-8479.
99. Nagai, Y.; Kobayashi, K.; Toi, H.; Aoyama, Y. B. *Chem. Soc. Jpn.* 1993, 66, 2965-2971.
100. Stones, D.; Manku, S.; Lu, X. S.; Hall, D. G. *Chem-Eur. J.* 2004, 10, 92-100.
101. Hargrove, A. E.; Ellington, A. D.; Anslyn, E. V.; Sessler, J. L. *Bioconjugate chemistry* 2011, 22, 388-396.
102. Van den Berg, R.; Peters, J. A.; Van Bekkum, H. *Carbohyd. Res.* 1994, 253, 1-12.
103. James, T. D.; Sandanayake, K. R. A. S.; Shinkai, S. *Angew. Chem. Int. Edit.* 1996, 35, 1910-1922.
104. Roy, D.; Cambre, J. N.; Sumerlin, B. S. *Chem. Commun.* 2009, 2106-2108.
105. Lee, L. L. Y.; Lee, J. C. *Biochemistry* 1987, 26, 7813-7819.
106. Senske, M.; Tork, L.; Born, B.; Havenith, M.; Herrmann, C.; Ebbinghaus, S. *J. Am. Chem. Soc.* 2014, 136, 9036-9041.
107. Amirgoulova, E. V.; Groll, J.; Heyes, C. D.; Ameringer, T.; Rocker, C.; Moller, M.; Nienhaus, G. U. *Chemphyschem* 2004, 5, 552-555.
108. Lee, E. S.; Gao, Z.; Bae, Y. H. *J. Control. Release* 2008, 132, 164-170.
109. Schreiber, A. B.; Haimovich, *J. Method Enzymol* 1983, 93, 147-155.
110. Ye, J.; Chen, Y.; Liu, Z. *Angew. Chem., Int. Ed.* 2014, 53, 10386-10389.
111. Zhang, W.; Liu, W.; Li, P.; Xiao, H.; Wang, H.; Tang, B. *Angew. Chem., Int. Ed.* 2014, 12697-12701.

I claim:
1. A method of creating a trehalose-based hydrogel, comprising the steps of:
   a) preparing a trehalose cross-linker;
   b) preparing a trehalose-based monomer; and
   c) reacting a mixture comprising the trehalose cross-linker and the trehalose-based monomer to form the trehalose-based hydrogel,
   wherein the trehalose cross-linker is synthesized using identical chemistry as is used to prepare the trehalose-based monomer
   wherein the mixture has a molar ratio of the trehalose-based monomer to the trehalose cross-linker of 18.96-50
   wherein—
   (i) the trehalose cross-linker has the structure

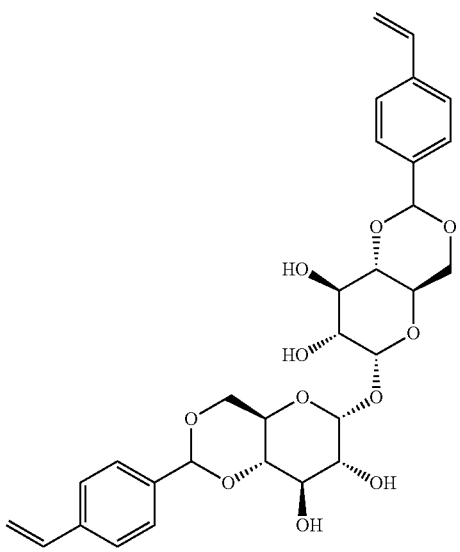

and the trehalose-based monomer has the structure

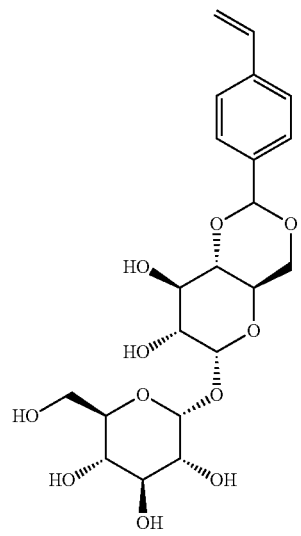

or (ii) the trehalose cross-linker comprises the structure

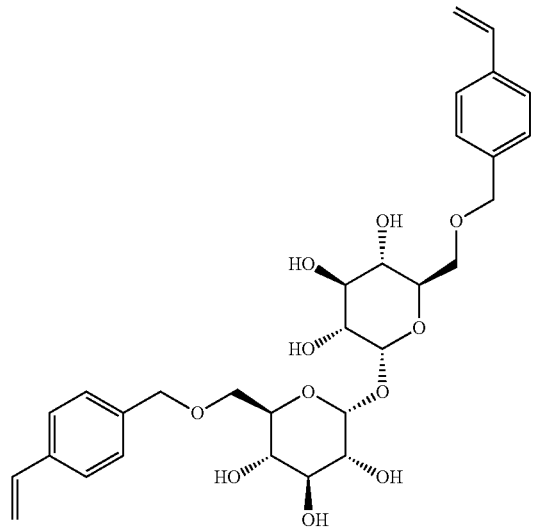 [SMILES: C=Cc1ccc(COC[C@H]2O[C@H](O[C@H]3O[C@H](COCc4ccc(C=C)cc4)[C@@H](O)[C@H](O)[C@H]3O)[C@H](O)[C@@H](O)[C@@H]2O)cc1]

and the trehalose-based monomer has the structure

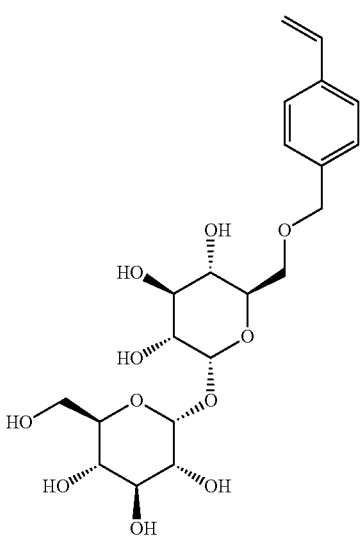 [SMILES: C=Cc1ccc(COC[C@H]2O[C@H](O[C@H]3O[C@H](CO)[C@@H](O)[C@H](O)[C@H]3O)[C@H](O)[C@@H](O)[C@@H]2O)cc1]

2. The method according to claim 1, wherein the trehalose cross-linker is synthesized during the same step as that is used to prepare the trehalose-based monomer.

3. The method according to claim 1, wherein the reaction in step c) is Free Radical Polymerization initiated by a Redox initiator.

4. The method according to claim 1, wherein the trehalose cross-linker has the structure

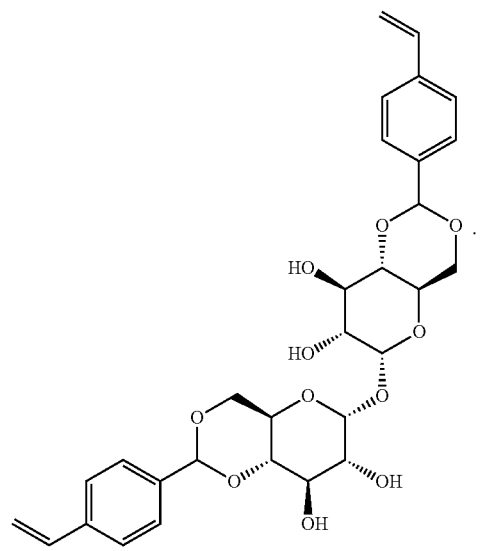

and the trehalose-based monomer has the structure

5. The method according to claim 1, wherein the trehalose cross-linker comprises the structure

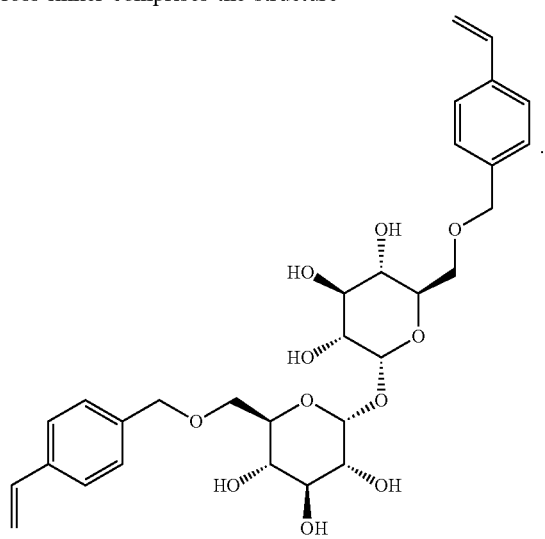

and wherein the trehalose-based monomer has the structure

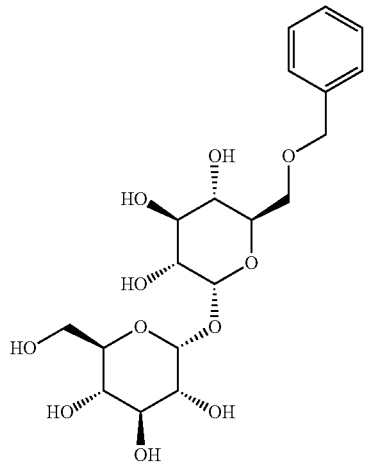 [SMILES: OC[C@H]1O[C@H](O[C@H]2O[C@H](COCc3ccccc3)[C@@H](O)[C@H](O)[C@H]2O)[C@H](O)[C@@H](O)[C@@H]1O]

6. The method according to claim 1, wherein no HPLC purification process to purify the trehalose-based monomer is needed.

7. A method of stabilizing a protein, comprising the steps of:
 a) preparing a trehalose-based hydrogel according to the method from claim 1; and
 b) adding a protein into the trehalose-based hydrogel either at the time of hydrogel formation or after the formation to form a complex of the protein and the trehalose-based hydrogel;
 wherein the protein is stabilized.

8. The method according to claim 7, wherein the protein is an enzyme.

9. The method according to claim 7, wherein the protein is stabilized when exposed to heat.

10. The method according to claim 9, wherein the protein is stabilized above 4° C.

11. The method according to claim 10, wherein the protein is stabilized at 70-90° C.

12. The method according to claim 7, wherein the protein is released from the complex of the protein and the trehalose-based hydrogel by diluting with water or lowering the pH.

* * * * *